United States Patent
Brewster et al.

(10) Patent No.: US 8,895,568 B2
(45) Date of Patent: *Nov. 25, 2014

(54) COMPOSITIONS COMPRISING SUBSTITUTED PTERIDINES AS AGROCHEMICALS

(71) Applicant: Dow AgroSciences LLC, Indianapolis, IN (US)

(72) Inventors: William K. Brewster, Indianapolis, IN (US); David A. Demeter, Fishers, IN (US); W. Randal Erickson, Carmel, IN (US); Christian T. Lowe, Westfield, IN (US); Carla J. R. Klittich, Zionsville, IN (US); Jaime S. Nugent, Brownsburg, IN (US); Brent J. Rieder, Greenfield, IN (US); Thomas L. Siddall, Zionsville, IN (US); Chenglin Yao, Westfield, IN (US); Carla N. Yerkes, Crawfordsville, IN (US); Yuanming Zhu, Carmel, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/898,372

(22) Filed: May 20, 2013

(65) Prior Publication Data

US 2013/0252960 A1    Sep. 26, 2013

Related U.S. Application Data

(62) Division of application No. 12/551,008, filed on Aug. 31, 2009, now Pat. No. 8,461,164.

(51) Int. Cl.
  *A61K 31/519* (2006.01)
  *A01N 43/90* (2006.01)
  *C07D 475/06* (2006.01)

(52) U.S. Cl.
  CPC .............. *A01N 43/90* (2013.01); *C07D 475/06* (2013.01)
  USPC .......................... 514/262.1; 544/257; 546/290

(58) Field of Classification Search
  CPC ..................................................... A61K 31/519
  USPC .......................... 514/262.1; 544/257; 546/290
  See application file for complete search history.

(56) References Cited

U.S. PATENT DOCUMENTS 5,034,393 A * 7/1991 Hackler et al. ............. 514/262.1
5,227,387 A   7/1993 Dreikorn

FOREIGN PATENT DOCUMENTS

EP    0414386 A1    2/1991
WO    WO93/04583    3/1993
WO    WO94/04526    3/1994
WO    WO94/04527    3/1994

OTHER PUBLICATIONS

International Searching Authority, International Search Report for PCT/US2009/055522, dated Mar. 3, 2011.
International Searching Authority, Written Opinion for PCT/US2009/055522, dated Mar. 3, 2011.
International Searching Authority, International Preliminary Report on Patentability for PCT/US2009/055522, dated Mar. 3, 2011.

* cited by examiner

*Primary Examiner* — Douglas M Willis
(74) *Attorney, Agent, or Firm* — C. W. Arnett; Faegre Baker Daniels LLP

(57) ABSTRACT

The present disclosure relates to 1- or 2-(4-(aryloxy)-phenyl) ethylamino-oxy- or sulfanyl) pteridines and 1- or 2-(4 Jheteroaryloxy)-phenyl)ethylamino-, oxy- or sulfanyl)pteridines and their use as agrochemicals and animal health products. The disclosure provides compounds of Formula (I-A) and Formula (I-B).

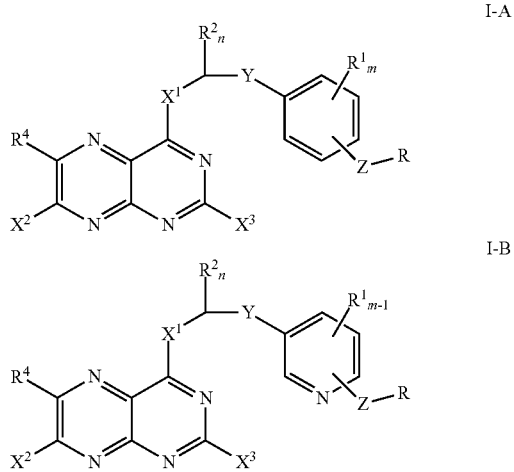

5 Claims, No Drawings

COMPOSITIONS COMPRISING SUBSTITUTED PTERIDINES AS AGROCHEMICALS

PRIORITY CLAIM

This application is a divisional application and claims priority to U.S. patent application Ser. No. 12/551,008, filed on Aug. 31, 2009, which is incorporated herein by reference in its entirety.

FIELD OF THE INVENTION

The present disclosure relates to 1- or 2-(4-(aryloxy)-phenyl)ethylamino-, oxy- or sulfanyl)pteridines and 1- or 2-(4-(heteroaryloxy)-phenyl)ethylamino-, oxy- or sulfanyl)pteridines and their use as agrochemicals and animal health products.

BACKGROUND AND SUMMARY

The present disclosure provides novel organic compounds that may demonstrate activity as pesticides, meaning that they may control fungi, insects, mites, and/or animal parasites. The disclosure also provides novel pesticide methods and compositions utilizing the novel compounds.

More specifically, the invention provides new compounds of the formula (I-A):

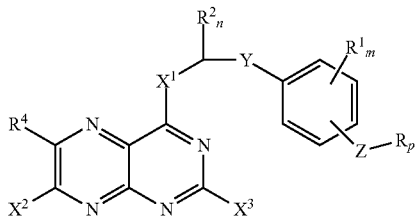

I-A wherein:
R is H, $CH_3$, phenyl, or a heterocycle comprising a 5 or 6 membered single ring or a fused ring system comprising at least one 5 or 6 membered heterocycle optionally substituted with H, halo, lower alkyl, lower alkoxy, benzyloxy, lower alkenyl, lower alkynyl, haloalkyl, haloalkoxy, $NO_2$, CN, lower alkoxycarbonyl, lower alkylcarbonyl, lower alkyl-$SO_q$, and aldoximes and lower alkyloximes, optionally substituted on oxygen by lower alkyl.
Z is H, a C—C single bond, $CH_2$, NH, O, S, CN, $CH_2O$, $OCH_2$, $CH_2CH_2O$, or $OCH_2CH_2$;
m is 4;
p is 0 or 1;
q is an integer from 0 to 2;
$R^1$ is independently H, halo, lower alkyl, lower alkenyl, lower alkynyl, hydroxy, lower alkoxy, haloalkyl, haloalkoxy, $NO_2$, CN, lower alkylcarbonyl, lower alkoxycarbonyl, mercapto, lower alkylthio, aldoximes and lower alkyloximes, optionally substituted on oxygen by lower alkyl;
Y is a C—C single bond, $C(R^5{}_n)O$ or $C(R^5{}_n)$;
n is 2;
alternatively $R^1{}_m$, Z, and $R_p$ may be taken together to form a fused 5 or 6 membered heterocycle optionally substituted with H, halo, lower alkyl, lower alkoxy, benzyloxy, lower alkenyl, lower alkynyl, haloalkyl, haloalkoxy, $NO_2$, CN, lower alkylcarbonyl, lower alkoxycarbonyl and lower alkyl-$SO_q$;
$R^2$ are independently H or lower alkyl;
$R^4$ is H, halogen, lower alkyl, lower alkoxy or lower haloalkyl;
$R^5$ are independently H or lower alkyl;
$X^1$ is $NR^3$, O, and S, where $R^3$ is selected from H, lower alkyl, lower alkylcarbonyl, lower alkoxycarbonyl, hydroxy, lower alkoxy, lower alkyl-$SO_q$, phenyl-$SO_q$ or substituted phenyl-$SO_q$;
$X^2$ is H, halogen or lower alkyl; and
$X^3$ is H, halogen or lower alkyl;
with the proviso that when Y is $C(R^5{}_n)$, $R^2{}_n$ and $R^1{}_m$ may be taken together to form

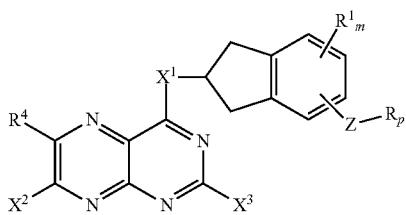

The invention also provides new compounds of formula (I-B):

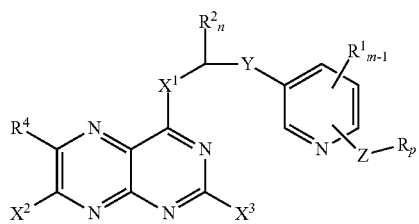

I-B wherein:
R is H, $CH_3$, haloalkyl, phenyl, or a heterocycle comprising a 5 or 6 membered single ring or a fused ring system comprising at least one 5 or 6 membered heterocycle optionally substituted with H, halo, lower alkyl, lower alkoxy, benzyloxy, lower alkenyl, lower alkynyl, haloalkyl, haloalkoxy, $NO_2$, CN, lower alkoxycarbonyl, lower alkylcarbonyl, lower alkyl$SO_q$, aldoximes and lower alkyloximes, optionally substituted on oxygen by lower alkyl;
Z is H, a C—C single bond, $CH_2$, NH, O, S, CN, $CH_2O$, $OCH_2$, $CH_2CH_2O$, or $OCH_2CH_2$;
m is 4;
p is 0 or 1;
q is an integer from 0 to 2;
$R^1$ is independently H, halo, lower alkyl, lower alkenyl, lower alkynyl, hydroxy, lower alkoxy, haloalkyl, haloalkoxy, $NO_2$, CN, lower alkylcarbonyl, lower alkoxycarbonyl, mercapto, lower alkylthio, aldoximes and lower alkyloximes, optionally substituted on oxygen by lower alkyl;
Y is a C—C single bond, $C(R^5{}_n)O$ or $C(R^5{}_n)$;
n is 2;
alternatively $R^1{}_m$, Z, and $R_p$ may be taken together to form a fused 5 or 6 membered heterocycle optionally substituted with H, halo, lower alkyl, lower alkoxy, benzyloxy, lower alkenyl, lower alkynyl, haloalkyl, haloalkoxy, $NO_2$, CN, lower alkylcarbonyl, lower alkoxycarbonyl and lower alkyl-$SO_q$;

$R^2$ are independently H or lower alkyl;

$R^4$ is H, halogen, lower alkyl, lower alkoxy or lower haloalkyl;

$R^5$ are independently H or lower alkyl;

$X^1$ is $NR^3$, O, and S, where $R^3$ is selected from H, lower alkyl, lower alkylcarbonyl, lower alkoxycarbonyl, hydroxy, lower alkoxy, lower alkyl-$SO_q$, phenyl-$SO_q$ or substituted phenyl-$SO_q$;

$X^2$ is H, halogen or lower alkyl; and $X^3$ is H, halogen or lower alkyl;

with the proviso that when Y is $C(R^5{}_n)$, $R^2{}_n$ and $R^1{}_m$ may be taken together to form

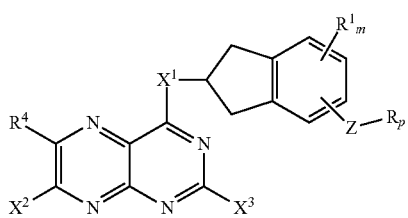

The invention also provides new pesticide methods and compositions utilizing the compounds of formula (I-A) and compounds of formula (I-B).

The invention includes fungicidal, insecticidal, acaricidal, and anti-parasitic compositions comprising an effective amount of a compound of the present invention in a mixture with an agriculturally acceptable or pharmaceutically acceptable adjuvant or carrier. The invention also includes methods of controlling a fungus, insect, mite, or parasite comprising applying an effective amount of a compound of the present invention to the fungus, insect or mite, soil, plant, root, foliage, seed, locus, or animal (for which purpose they may be administered orally, parenterally, percutaneously or topically) in which the infestation is to be prevented or cured.

DETAILED DESCRIPTION OF THE INVENTION

The compounds of the present invention are directed to compounds of formula (I-A) and (I-B)

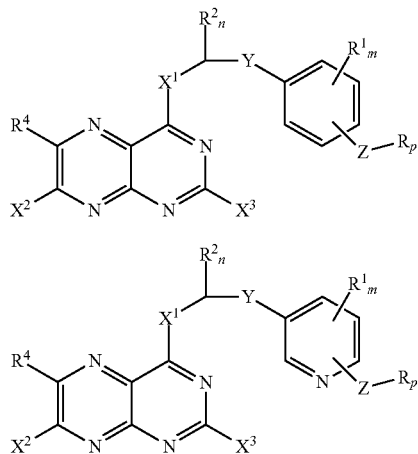

Wherein p is 1 and R may be an optionally substituted phenyl or a heterocycle comprising a 5 or 6 membered single ring or a fused ring system comprising at least one 5 or 6 membered heterocycle. More specifically, R may be selected from the list including but not limited to:

optionally substituted pyridinyl

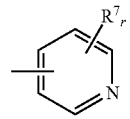

optionally substituted pyrazinyl

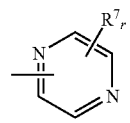

optionally substituted pyrimidinyl

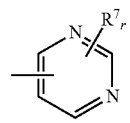

optionally substituted pyridazinyl

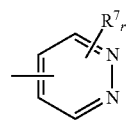

optionally substituted thiazolyl

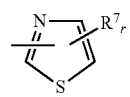

optionally substituted 1,2,3-thiadiazolyl

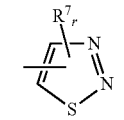

optionally substituted 1,2,4-thiadiazolyl

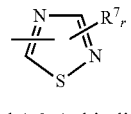

optionally substituted 1,3,4-thiadiazolyl

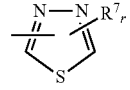

as well as pyridinyl-N-oxide, thienyl, furyl, oxazolyl, isoxazolyl, isothiazolyl, oxadiazolyl, furazanyl, pyrrolyl, pyrazolyl, and imidazolyl, where r is 4 in the case of pyridinyl, 3 in the case of pyrazinyl, pyrimidinyl, and pyridazinyl, 2 in the case of thiazolyl and 1 in the case of thiadiazolyl, and $R^7$ are independently H, halo, lower alkyl, lower alkoxy, benzyloxy, lower alkenyl, lower alkynyl, haloalkyl, haloalkoxy, $NO_2$, CN, lower alkoxycarbonyl, lower alkylcarbonyl, aldoximes and lower alkyloximes, optionally substituted on oxygen by lower alkyl. and lower alkyl-$SO_q$ and q is an integer from 0 to 2.

Throughout this document, all temperatures are given in degrees Celsius, and all percentages are weight percentages unless otherwise stated.

The terms "alkyl," "alkenyl" and "alkynyl," as well as derivative terms such as "alkoxy" and "alkylthio," as used herein, include within their scope straight chain, branched chain and cyclic moieties. The terms "alkenyl" and "alkynyl" are intended to include one or more unsaturated bonds.

The term "halo" refers to F, Cl, Br, and I atoms.

The term "lower alkyl" refers to $C_1$ to $C_6$ straight hydrocarbon chains and $C_3$ to $C_6$ branched and cyclic hydrocarbon groups.

The terms "lower alkenyl" and "lower alkynyl" refer to $C_2$ to $C_6$ straight hydrocarbon chains and $C_3$ (or $C_4$ in the case of lower alkynyl) to $C_6$ branched hydrocarbon groups containing at least one unsaturated bond.

The terms "lower alkoxy" and "lower alkylthio" refer to O-lower alkyl and S-lower alkyl groups.

The term "haloalkyl" refers to lower alkyl groups substituted with one or more halo atoms.

The term "haloalkoxy" refers to lower alkoxy groups substituted with one or more halo atoms.

The term "substituted phenyl" refers to phenyl substituted with lower alkyl, lower alkenyl, lower alkynyl, lower alkoxy, lower alkylthio, halo, hydroxy, $NO_2$, haloalkyl, haloalkoxy, haloalkylthio, CN, phenyl, substituted phenyl, O-phenyl, O-substituted phenyl, $C_1$-$C_4$ alkanoyloxy, $C_1$-$C_4$ alkoxycarbonyl, lower alkylcarbonyl, benzyloxy, or and lower alkyl-$SO_q$ and q is an integer from 0 to 2.

The term "fused ring system" refers to two rings joined, as defined in Moss, G. P. *Pure and Applied Chemistry,* 1998, 70, 143: "For ring systems . . . two rings which have two atoms and one bond in common may be regarded as being derived from the two rings as separate entities. The process of joining rings in this way is termed fusion."

In the present invention, whenever multiple substituents are independently selected it is to be understood that they are selected so as to be sterically compatible with each other. Steric compatibility refers to the absence of steric hindrance as this term is defined in The Condensed Chemical Dictionary, 7th edition, Reinhold Publishing Co., N.Y. page 893 (1966), which definition is as follows:

Steric hindrance. A characteristic of molecular structure in which the molecules have a spatial arrangement of their atoms such that a given reaction with another molecule is prevented or retarded in rate.

Steric compatibility is characterized by substituents whose physical bulk does not require confinement within volumes insufficient for the exercise of their normal behavior as discussed in D. J. Cram and G. Hammond, Organic Chemistry 2nd edition, McGraw-Hill Book Company, N.Y. page 215 (1964).

The compounds of this invention are made using well known chemical procedures. The required starting materials are commercially available or are readily synthesized using standard procedures.

Synthesis of Compounds of Formula (I-A) wherein $X^1$ is O

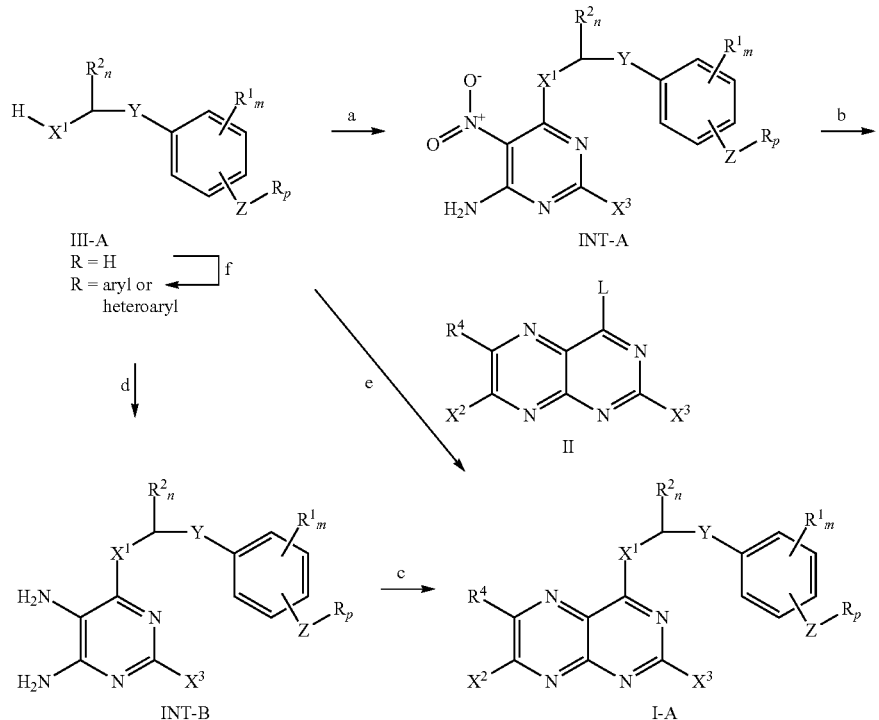

Scheme I

The compounds of formula (I-A) wherein $X^1$ is O can be made by condensing a compound of formula (II)

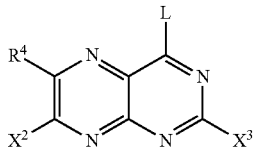

where $R^4$, $X^2$ and $X^3$ are as defined as for compounds of formula (I-A); and L is a group such as F, Cl, Br, 1,2,3-triazol-1-yl, 1,2,4-triazol-1-yl, OH, arylthio, alkylthio, alkylsulfonyl, arylsulfonyl, alkoxy, alkylsulfonyl, or arylsulfonyl; with a compound of the formula (III-A)

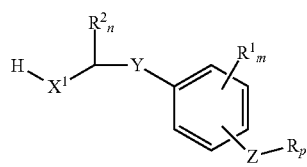

where R, $R^1$, $R^2$, Y, Z, m, n, and p are as defined for compounds of formula (I-A) and $X^1$ is O as in step e of Scheme I. The reaction is preferably carried out in the presence of a base in a non-reactive solvent, such as dichloromethane ($CH_2Cl_2$), tetrahydrofuran (THF), dimethylsulfoxide (DMSO) or N,N-dimethylformamide (DMF), at a temperature in the range of 0° C. to reflux temperature.

Alternatively, compounds of formula (I-A) can be made by reaction of a dicarbonyl or equivalent compound with a compound of formula (INT-B)

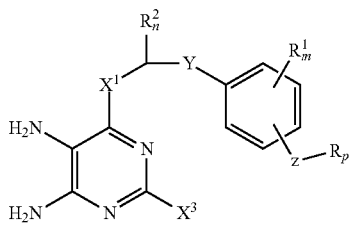

where R, $R^1$, $R^2$, $X^3$, Y, Z, m, n, and p are as defined for compounds of formula (I-A) and $X^1$ is O, as in step c of Scheme I. Representative dicarbonyl compounds include glyoxal, 2,3-butanedione and 1,4-dioxane-2,3-diol. The reaction is preferably carried out in an alcohol solvent, alternatively containing toluene, at a temperature in the range of 0° C. to reflux temperature.

Compounds of formula (INT-B) can be made by reaction of a 5,6-diaminopyrimidine compound

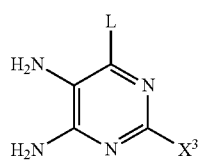

where $X^3$ and L are as defined as for compounds of formula (II); with a compound of formula (III-A) where R, $R^1$, $R^2$, Y, Z, m, n, and p are as defined for compounds of formula (I-A) and $X^1$ is O as in step d of Scheme I. The reaction is preferably carried out in the presence of a base in a non-reactive solvent, such as $CH_2Cl_2$, THF, DMSO or DMF, at a temperature in the range of 0° C. to reflux temperature.

Alternatively, compounds of formula (INT-B) can be synthesized by reduction of a 6-amino-5-nitropyrimidine compound of formula (INT-A)

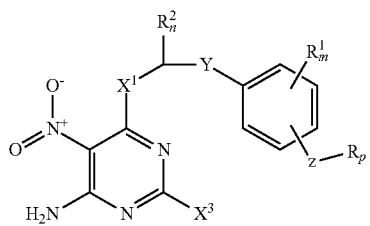

where R, $R^1$, $R^2$, $X^3$, Y, Z, m, n, and p are as defined for compounds of formula (I-A) as in step b of Scheme I. Reduction can be achieved by hydrogenation in the presence of a palladium catalyst in an alcohol solvent.

Compounds of formula (INT-A) can be synthesized by reaction of a 5-nitro-6-aminopyrimidine compound

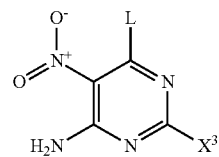

where $X^3$ and L are as defined as for compounds of formula (II); with a compound of formula (III-A) where R, $R^1$, $R^2$, Y, Z, m, n, and p are as defined for compounds of formula (I-A) as in step a of Scheme I. The reaction is preferably carried out in the presence of a base in a non-reactive solvent, such as $CH_2Cl_2$, THF, DMSO or DMF, at a temperature in the range of 0° to reflux temperature.

Compounds of formula (III-A), where R is a phenyl or heteroaryl, may be synthesized by reaction of compounds of formula (III-A) where R is H, with a compound of formula M-Het where M is a group such as F, Cl, Br, I, 1,2,3-triazol-1-yl, 1,2,4-triazol-1-yl, OH, arylthio, alkylthio, alkylsulfonyl, arylsulfonyl, alkoxy, alkylsulfinyl, or arylsulfinyl; and wherein Het is a phenyl or heterocycle, as in step f of Scheme I. Het may be optionally substituted with one or more groups selected from H, halo, lower alkyl, lower alkoxy, benzyloxy, lower alkenyl, lower alkynyl, haloalkyl, haloalkoxy, $NO_2$, CN, lower alkoxycarbonyl, lower alkylcarbonyl and lower alkyl-$SO_q$. The reaction is preferably carried out in the presence of a base in a non-reactive solvent, such as $CH_2Cl_2$, THF, DMSO or DMF, at a temperature in the range of 0° C. to reflux temperature.

Synthesis of Compounds of Formula (I-A) wherein $X^1$ is NH or N-lower alkyl.

The compounds of formula (I-A) wherein $X^1$ is NH or N-lower alkyl and R, $R^1$, $R^2$, $R^4$, $X^2$, $X^3$, Y, Z, m, n and p are as defined for compounds of formula (I-A), can be made in the same manner as described for Scheme I, from compounds of the formulas (II), (III-A), (INT-A), (INT-B) wherein R, $R^1$, $R^2$, $R^4$, $X^2$, $X^3$, Y, Z, m, n and p are as defined for formula (I-A), and $X^1$ is NH or N-lower alkyl.

Scheme II

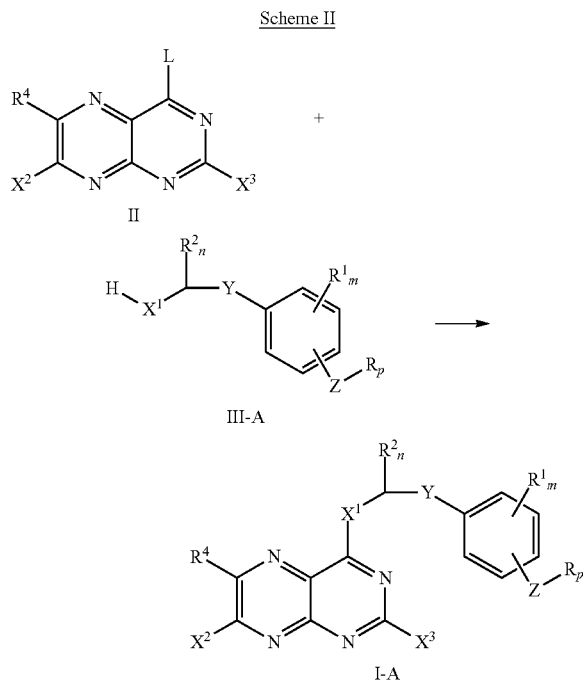

Preferably, the compounds of formula (I-A) wherein $X^1$ is NH or N-lower alkyl and Z is as defined for compounds of formula (I-A), can be made by condensing a compound of formula (II)

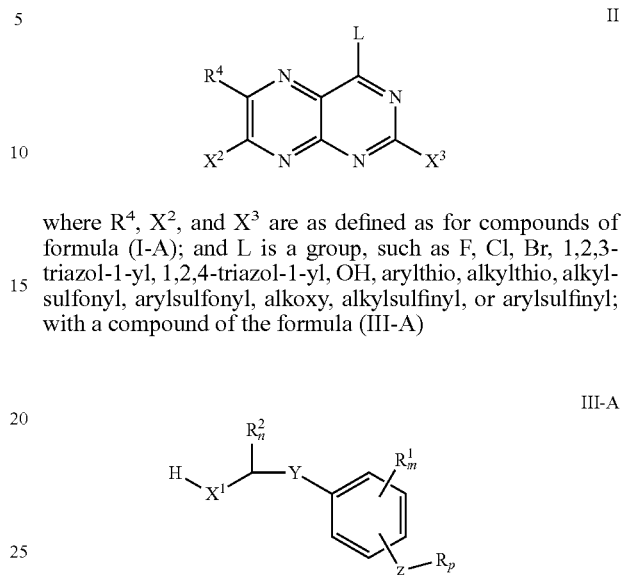

where $R^4$, $X^2$, and $X^3$ are as defined as for compounds of formula (I-A); and L is a group, such as F, Cl, Br, 1,2,3-triazol-1-yl, 1,2,4-triazol-1-yl, OH, arylthio, alkylthio, alkylsulfonyl, arylsulfonyl, alkoxy, alkylsulfinyl, or arylsulfinyl; with a compound of the formula (III-A)

where R, $R^1$, $R^2$, Y, Z, m, n, and p are as defined for compounds of formula (I-A) and $X^1$ is NH or N-lower alkyl, optionally as a salt (e.g., HCl), as in Scheme II. The reaction is preferably carried out in the presence of base, such as triethylamine, in a non-reactive solvent, such as $CH_2Cl_2$, THF or DMF. Alternatively, the reaction may be carried out in hexamethyldisilazane in the presence of ammonium sulfate.

Scheme III

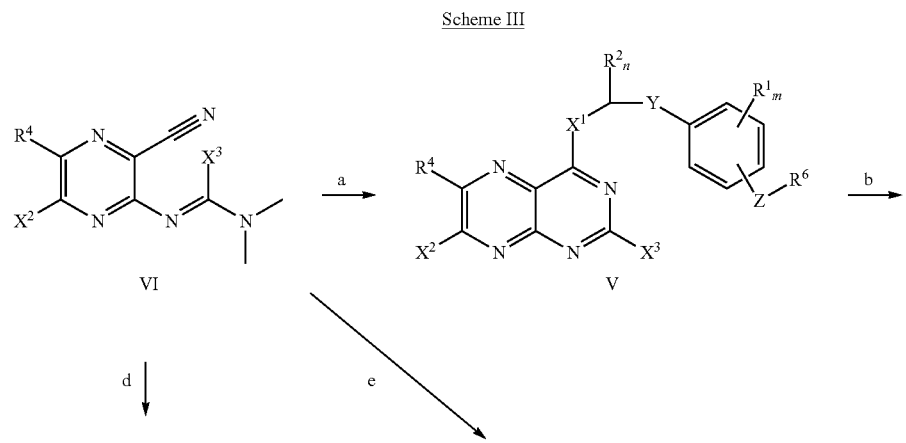

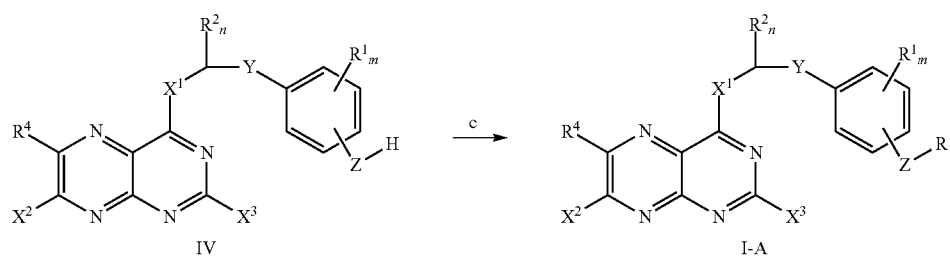

The compounds of formula (I-A) wherein $X^1$ is NH or N-lower alkyl and R, $R^1$, $R^2$, $R^3$, $R^4$, $X^2$, $X^3$, and Z are as defined for compounds of formula (I-A) where R is a phenyl or heterocycle optionally substituted with one or more groups selected from halo, lower alkyl, lower alkenyl, lower alkynyl, lower alkoxy, haloalkyl, haloalkoxy, $NO_2$, CN, lower alkoxycarbonyl, lower alkylcarbonyl and lower alkyl-$SO_q$, when q is an integer from 0 to 2;

Alternatively are prepared by treatment of a compound of formula (IV)

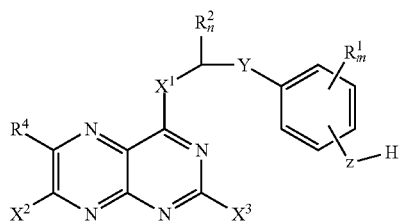

wherein $R^1$, $R^2$, $R^4$, $X^2$, $X^3$, Y, Z, m and n are as defined for compounds of formula (I-A) and $X^1$ is NH or N-lower alkyl; with a compound of formula M-Het where M is a group such as F, Cl, Br, I ,1,2,3-triazol-1-yl, 1,2,4-triazol-1-yl, OH, arylthio, alkylthio, alkylsulfonyl, arylsulfonyl, alkoxy, alkylsulfinyl, or arylsulfinyl; and wherein Het is a phenyl or heterocycle, as in step c of Scheme III. Het may be optionally substituted with one or more groups selected from H, halo, lower alkyl, lower alkoxy, benzyloxy, lower alkenyl, lower alkynyl, haloalkyl, haloalkoxy, $NO_2$, CN, lower alkoxycarbonyl, lower alkylcarbonyl and lower alkyl-$SO_q$. The reaction is preferably carried out in the presence of a base in a non-reactive solvent, such as $CH_2Cl_2$, THF, DMSO or DMF, at a temperature in the range of 0° C. to reflux temperature.

Certain compounds of formula (I-A) are prepared by modifications of other compounds of formula (I-A), by methods described in the experimental procedures of the Preparations and Examples section.

The compounds of formula (IV) where Z is oxygen can be prepared by treatment of compounds of formula (V)

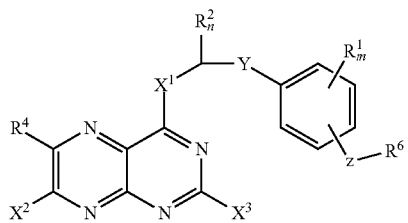

where $R^1$, $R^2$, $R^3$, $R^4$, Y, m and n are as defined for compounds of formula (I-A), $X^1$ is NH or N-lower alkyl, Z is oxygen, and $R^6$ is lower alkyl; with a reagent such as $BBr_3$ in a nonreactive organic solvent, such as $CH_2Cl_2$.

The compounds of formula (IV) alternatively may be prepared by treatment of compounds of formula (VI) wherein $R^4$, $X^2$ and $X^3$ are as described for compound of formula (I-A),

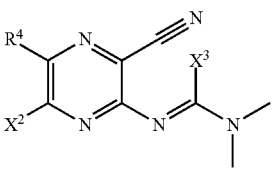

with a compound of formula (VII), optionally as a salt (e.g., HCl),

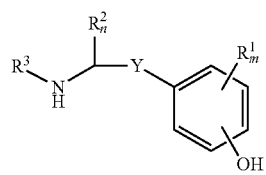

where $R^1$, $R^2$, Y, m and n are as defined for compounds of formula (I-A), and $R^3$ is H; in the presence of acetic acid, optionally as a solution in an appropriate solvent such as ethanol; with heating at temperatures from 25° to reflux.

The compounds of formula (IV) alternatively may be prepared by treatment of compounds of formula (II)

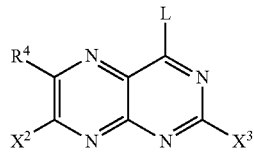

where $R^4$, $X^2$ and $X^3$ are as defined for compounds of formula (I-A); and L is a leaving group, such as F, Cl, Br, I, $NO_2$, 1,2,3-triazol-1-yl, 1,2,4-triazol-1-yl, $OSiMe_3$, arylthio, alkylthio, alkylsulfonyl, arylsulfonyl, alkoxy, alkylsulfinyl or arylsulfinyl; with a compound of formula (VII), optionally as a salt (e.g., HCl),

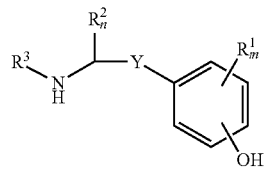

where $R^1$, $R^2$, $R^3$, Y, m and n are as defined for compounds of formula (I-A); optionally in the presence of a base, in a solvent such as acetonitrile, THF or DMF.

Compounds of formula (V) are prepared by the treatment of compounds of formula (VI) wherein $R^4$, $X^2$, and $X^3$ are as described for compound of formula (I-A); with a compound of formula (VIII-A), optionally as a salt (e.g., HCl),

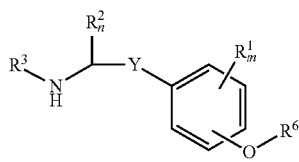

VIII-A where $R^1$, $R^2$, Y, m and n are as defined for compounds of formula (I-A), $R^3$ is H, and $R^6$ is lower alkyl as defined for compounds of formula (I-A); in the presence of acetic acid, optionally as a solution in an appropriate solvent such as ethanol; with heating at temperatures from 25° C. to reflux.

Amines of formula (VIII-A) where $R^1$, $R^2$, $R^3$, Y, m and n are as defined for compounds of formula (I-A) and $R^6$ is lower alkyl as defined for compounds of formula (1-A); are commercially available or may be prepared by well-known methods. For example, compounds of formula (VIII-A), where $R^1$, $R^2$, m and n are as defined for compounds of formula (I-A), $R^6$ is lower alkyl, $R^3$ is H, and Y is $R^5{}_n$ are prepared as their hydrochloride salts by treatment of appropriately substituted (4-alkoxyphenyl)-acetonitriles with hydrogen in the presence of hydrochloric acid, a catalyst such as palladium on carbon, and an appropriate solvent such as ethanol.

Alternatively, compounds of formula (VIII-A), where $R^1$, $R^2$, m and n are as defined for compounds of formula (I-A), $R^6$ is lower alkyl, $R^3$ is H, Y is $R^5{}_n$ are prepared by treatment of appropriately substituted (4-alkoxyphenyl)-acetonitriles with borane-dimethyl sulfide complex or lithium aluminum hydride in an appropriate solvent such as tetrahydrofuran at temperatures from 20° C. to reflux.

Alternatively, compounds of formula (VIII-A), where $R^1$, $R^2$, m and n are as defined for compounds of formula (I-A), $R^6$ is lower alkyl, $R^3$ is H, and Y is $R^5{}_n$ are prepared as their hydrochloride salts by treatment of appropriately substituted 1-alkoxy-4-((E)-2-nitrovinyl)-benzenes with hydrogen in the presence of hydrochloric acid, a catalyst such as palladium on carbon, and an appropriate solvent such as ethanol.

Alternatively, compounds of formula (VIII-A), where $R^1$, $R^2$, m and n are as defined for compounds of formula (I-A), $R^6$ is alkyl or benzyl, $R^3$ is H, and Y is $R^5{}_n$ are prepared by treatment of the appropriately substituted 1-alkoxy-4-((E)-2-nitrovinyl)-benzenes with lithium aluminum hydride in an appropriate solvent such as tetrahydrofuran.

The 1-alkoxy-4-((E)-2-nitrovinyl)-benzenes are prepared by treatment of the appropriately substituted benzaldehyde with nitromethane in the presence of ammonium acetate.

The compounds of formula (I-A) wherein X is NH alternatively are prepared by treatment of a compound of formula (VI), as defined above, with a compound of formula (M-A), optionally as a salt (e.g., HCl), where R, $R^1$, $R^2$, Y, Z, m, n and p are as defined for compounds of formula (I-A) and X is NH; in the presence of acetic acid, optionally as a solution in an appropriate solvent such as ethanol; with heating at temperatures from 25° to reflux.

Similarly, compounds of formula (I-B), wherein $X^1$ is NH can be prepared by treatment of a compound of formula (VI), as defined above, with a compound of formula (III-B)

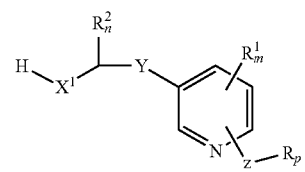

III-B optionally as a salt (e.g., HCl), where R, $R^1$, $R^2$, Y, Z, m, n and p are as defined for compounds of formula (I-B) and X is NH; in the presence of acetic acid, optionally as a solution in an appropriate solvent such as ethanol; with heating at temperatures from 25° to reflux. Compounds of formula (III-B) can be prepared by the methods in the Preparations and Examples section.

Compounds of formula (VI)

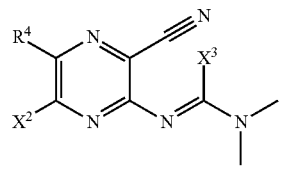

VI where $R^4$, $X^2$ and $X^3$ are as described for compound of formula (I-A) were prepared by treatment of a compound of formula (IX)

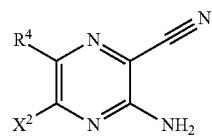

IX where $R^4$ and $X^2$ are as described for compound of formula (I-A), with N,N-dimethylformamide dimethyl acetal in an appropriate solvent such as toluene, with heating at temperature from 25° C. up to the reflux temperature.

Compounds of formula (IX)

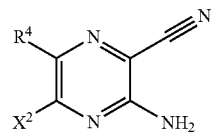

IX where $R^4$ and $X^2$ are as defined for compounds of formula (I-A) are commercially available or were prepared by well known synthetic procedures.

Synthesis of Compounds of Formula (I-A) wherein $X^1$ is S.

Scheme IV

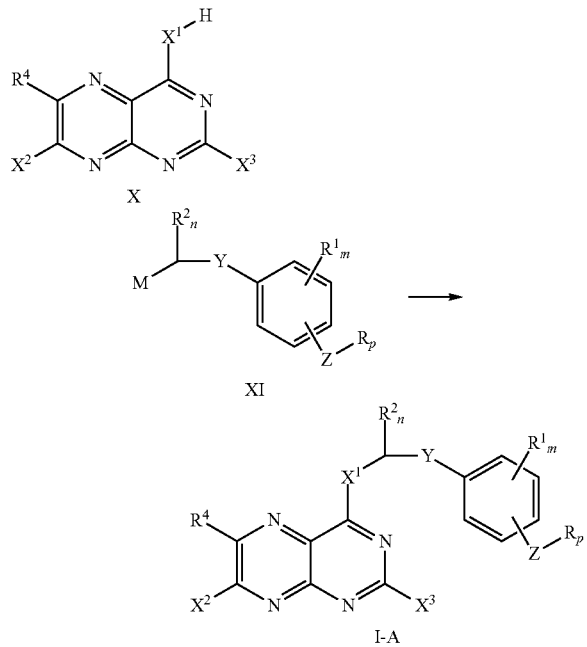

The compounds of formula (I-A) wherein R, $R^1$, $R^2$, $R^4$, $X^2$, $X^3$, Y, Z, m, n, and p are as defined for compounds of formula (I-A), and $X^1$ is S, can be made as in Scheme IV by condensing a compound of formula (X)

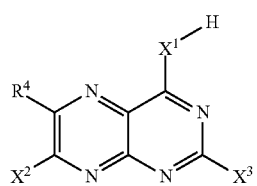

where $R^4$, $X^2$, and $X^3$ are as defined as for compounds of formula (I-A); and $X^1$ is S; with a compound of the formula (XI)

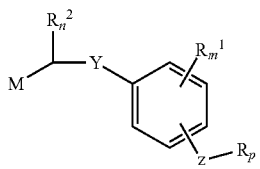

where R, $R^1$, $R^2$, Y, Z, m, n, and p are as defined for formula (I-A); and M is as defined in the reacting partner M-Het in Scheme III, step c. In compounds of formula (XI), M is preferably chlorine or bromine The reaction is preferably carried out in the presence of base, such as triethylamine, in a non-reactive solvent, such as $CH_2Cl_2$, THF or DMF.

The compounds of the present invention may be pesticides that have fungitoxic activity against harmful fungi including, but not limited to, fungi that are pathogens of plants, animals, and humans. They are active against fungi of a number of classes including Oomycetes, Deuteromycetes (Fungi Imperfecti), Basidiomycetes, and Ascomycetes. More particularly, one embodiment of the present invention provides for activity against phytopathogenic organisms including, but not limited to, *Pyricularia oryzae*, *Colletotrichum* species, *Erysiphe* species, *Puccinia* species, *Cochliobolus* species, *Alternaria* species, *Septoria* species, *Rhynchosporium* secalis, *Cercospora* and *Cercosporella* species, and *Pyrenophora* species. Additional diseases controlled include powdery mildews incited by *Sphaerotheca* fulignea (cucurbit powdery mildew) and *Uncinula necator* (grape powdery mildew), soybean rust incited by *Phakopsora pachyrhizi*, downy mildews such as cucumber downy mildew (*Pseudoperonospora cubensis*), grape downy mildew (*Plasmopara viticola*), apple scab incited by *Venturia inaequalis*, late blight incited by *Phytophthora infestans*, and Maize smut (*Ustilago maydis*).

The compounds of the present invention may have insecticidal activity against harmful insects and mites including, but not limited to, insects that are pests or parasites of plants, animals, and humans.

In other embodiments, the invention disclosed in this document may be used to control pests of Phylum Nematoda, the Phylum Arthropoda, the Subphylum Chelicerata, the Class Arachnida, the Subphylum Myriapoda, the Class Symphyla, the Subphylum Hexapoda, the Class Insecta. Within the Class Insecta, the invention disclosed in this document may be use to control Coleoptera (beetles). A non-exhaustive list of these such pests includes, but is not limited to, *Acanthoscelides* spp. (weevils), *Acanthoscelides obtectus* (common bean weevil), *Agrilus planipennis* (emerald ash borer), *Agriotes* spp. (wireworms), *Anoplophora glabripennis* (Asian longhorned beetle), *Anthonomus* spp. (weevils), *Anthonomus grandis* (boll weevil), *Aphidius* spp., *Apion* spp. (weevils), *Apogonia* spp. (grubs), *Ataenius spretulus* (Black Turfgrass Ataenius), *Atomaria linearis* (pygmy mangold beetle), *Aulacophore* spp., *Bothynoderes punctiventris* (beet root weevil), *Bruchus* spp. (weevils), *Bruchus pisorum* (pea weevil), *Cacoesia* spp., *Callosobruchus* maculatus (southern cow pea weevil), *Carpophilus hemipteras* (dried fruit beetle), *Cassida vittata*, *Cerosterna* spp., *Cerotoma* spp. (chrysomeids), *Cerotoma trifurcata* (bean leaf beetle), *Ceutorhynchus* spp. (weevils), *Ceutorhynchus assimilis* (cabbage seedpod weevil), *Ceutorhynchus napi* (cabbage curculio), *Chaetocnema* spp. (chrysomelids), *Colaspis* spp. (soil beetles), *Conoderus scalaris, Conoderus stigmosus, Conotrachelus nenuphar* (plum curculio), *Cotinus nitidis* (Green June beetle), *Crioceris asparagi* (asparagus beetle), *Cryptolestes ferrugineus* (rusty grain beetle), *Cryptolestes pusillus* (flat grain beetle), *Cryptolestes turcicus* (Turkish grain beetle), *Ctenicera* spp. (wireworms), *Curculio* spp. (weevils), *Cyclocephala* spp. (grubs), *Cylindrocpturus adspersus* (sunflower stem weevil), *Deporaus marginatus* (mango leaf-cutting weevil), *Dermestes lardarius* (larder beetle), *Dermestes maculates* (hide beetle), *Diabrotica* spp. (chrysolemids), *Epilachna varivestis* (Mexican bean beetle), *Faustinus cubae, Hylobius pales* (pales weevil), *Hypera* spp. (weevils), *Hypera postica* (alfalfa weevil), *Hyperdoes* spp. (Hyperodes weevil), *Hypothenemus hampei* (coffee berry beetle), *Ips* spp. (engravers), *Lasioderma serricorne* (cigarette beetle), *Leptinotarsa decemlineata* (Colorado potato beetle), *Liogenys fuscus, Liogenys suturalis, Lissorhoptrus oryzophilus* (rice water weevil), *Lyctus* spp. (wood beetles/powder post beetles), *Maecolaspis joliveti, Megascelis* spp., *Melanotus* communis, *Meligethes* spp., *Meligethes aeneus* (blossom beetle), *Melolontha melolontha* (common European cockchafer), *Oberea brevis, Oberea lin-*

*earis, Oryctes rhinoceros* (date palm beetle), *Oryzaephilus mercator* (merchant grain beetle), *Oryzaephilus surinamensis* (sawtoothed grain beetle), *Otiorhynchus* spp. (weevils), *Oulema melanopus* (cereal leaf beetle), *Oulema oryzae, Pantomorus* spp. (weevils), *Phyllophaga* spp. (May/June beetle), *Phyllophaga cuyabana, Phyllotreta* spp. (chrysomelids), *Phynchites* spp., *Popillia japonica* (Japanese beetle), *Prostephanus truncates* (larger grain borer), *Rhizopertha dominica* (lesser grain borer), *Rhizotrogus* spp. (European chafer), *Rhynchophorus* spp. (weevils), *Scolytus* spp. (wood beetles), *Shenophorus* spp. (Billbug), *Sitona* lineatus (pea leaf weevil), *Sitophilus* spp. (grain weevils), *Sitophilus granaries* (granary weevil), *Sitophilus oryzae* (rice weevil), *Stegobium paniceum* (drugstore beetle), *Tribolium* spp. (flour beetles), *Tribolium castaneum* (red flour beetle), *Tribolium confusum* (confused flour beetle), *Trogoderma variabile* (warehouse beetle), and *Zabrus tenebioides*.

In another embodiment, the invention disclosed in this document may be used to control Dermaptera (earwigs).

In another embodiment, the invention disclosed in this document may be used to control Dictyoptera (cockroaches). A non-exhaustive list of such pests includes, but is not limited to, *Blattella germanica* (German cockroach), *Blatta orientalis* (oriental cockroach), *Parcoblatta pennsylvanica, Periplaneta americana* (American cockroach), *Periplaneta australoasiae* (Australian cockroach), *Periplaneta brunnea* (brown cockroach), *Periplaneta fuliginosa* (smokybrown cockroach), *Pycnoselus surinamensis* (Surinam cockroach), and *Supella longipalpa* (brownbanded cockroach).

In another embodiment, the invention disclosed in this document may be used to control Diptera (true flies). A non-exhaustive list of such pests includes, but is not limited to, *Aedes* spp. (mosquitoes), *Agromyza* frontella (alfalfa blotch leafminer), *Agromyza* spp. (leaf miner flies), *Anastrepha* spp. (fruit flies), *Anastrepha* suspensa (Caribbean fruit fly), *Anopheles* spp. (mosquitoes), *Batrocera* spp. (fruit flies), *Bactrocera cucurbitae* (melon fly), *Bactrocera dorsalis* (oriental fruit fly), *Ceratitis* spp. (fruit flies), *Ceratitis capitata* (Mediterranean fruit fly), *Chrysops* spp. (deer flies), *Cochliomyia* spp. (screwworms), *Contarinia* spp. (Gall midges), *Culex* spp. (mosquitoes), *Dasineura* spp. (gall midges), *Dasineura brassicae* (cabbage gall midge), *Delia* spp., *Delia platura* (seedcorn maggot), *Drosophila* spp. (vinegar flies), *Fannia* spp. (filth flies), *Fannia canicularis* (little house fly), *Fannia scalaris* (latrine fly), *Gasterophilus intestinalis* (horse bot fly), *Gracillia perseae, Haematobia irritans* (horn fly), *Hylemyia* spp. (root maggots), *Hypoderma* lineatum (common cattle grub), *Liriomyza* spp. (leafminer flies), *Liriomyza brassica* (serpentine leafminer), *Melophagus ovinus* (sheep ked), *Musca* spp. (muscid flies), *Musca autumnalis* (face fly), *Musca domestica* (house fly), *Oestrus ovis* (sheep bot fly), *Oscinella frit* (frit fly), *Pegomyia betae* (beet leafminer), *Phorbia* spp., *Psila rosae* (carrot rust fly), *Rhagoletis cerasi* (cherry fruit fly), *Rhagoletis pomonella* (apple maggot), *Sitodiplosis mosellana* (orange wheat blossom midge), *Stomoxys calcitrans* (stable fly), *Tabanus* spp. (horse flies), and *Tipula* spp. (crane flies).

In another embodiment, the invention disclosed in this document may be used to control Hemiptera (true bugs). A non-exhaustive list of such pests includes, but is not limited to, *Acrosternum hilare* (green stink bug), *Blissus leucopterus* (chinch bug), *Calocoris norvegicus* (potato mirid), Cimex hemipterus (tropical bed bug), Cimex lectularius (bed bug), *Dagbertus fasciatus, Dichelops furcatus, Dysdercus suturellus* (cotton stainer), *Edessa meditabunda, Eurygaster maura* (cereal bug), *Euschistus heros, Euschistus servus* (brown stink bug), *Helopeltis antonii, Helopeltis theivora* (tea blight plantbug), *Lagynotomus* spp. (stink bugs), *Leptocorisa oratorius, Leptocorisa varicornis, Lygus* spp. (plant bugs), *Lygus hesperus* (western tarnished plant bug), *Maconellicoccus hirsutus, Neurocolpus longirostris, Nezara viridula* (southern green stink bug), *Phytocoris* spp. (plant bugs), *Phytocoris californicus, Phytocoris relativus, Piezodorus guildingi, Poecilocapsus lineatus* (fourlined plant bug), *Psallus vaccinicola, Pseudacysta perseae, Scaptocoris castanea*, and *Triatoma* spp. (bloodsucking conenose bugs/kissing bugs).

In another embodiment, the invention disclosed in this document may be used to control Homoptera (aphids, scales, whiteflies, leafhoppers). A non-exhaustive list of such pests includes, but is not limited to, *Acrythosiphon pisum* (pea aphid), *Adelges* spp. (adelgids), *Aleurodes proletella* (cabbage whitefly), *Aleurodicus disperses, Aleurothrixus floccosus* (woolly whitefly), *Aluacaspis* spp., *Amrasca bigutella bigutella, Aphrophora* spp. (leafhoppers), *Aonidiella aurantii* (California red scale), *Aphis* spp. (aphids), *Aphis gossypii* (cotton aphid), *Aphis pomi* (apple aphid), *Aulacorthum solani* (foxglove aphid), *Bemisia* spp. (whiteflies), *Bemisia argentifolii, Bemisia tabaci* (sweetpotato whitefly), *Brachycolus noxius* (Russian aphid), *Brachycorynella asparagi* (asparagus aphid), *Brevennia rehi, Brevicoryne brassicae* (cabbage aphid), *Ceroplastes* spp. (scales), *Ceroplastes rubens* (red wax scale), *Chionaspis* spp. (scales), *Chrysomphalus* spp. (scales), *Coccus* spp. (scales), *Dysaphis plantaginea* (rosy apple aphid), *Empoasca* spp. (leafhoppers), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum* granarium (English grain aphid), *Macrosiphum* rosae (rose aphid), *Macrosteles quadrilineatus* (aster leafhopper), *Mahanarva frimbiolata, Metopolophium dirhodum* (rose grain aphid), *Mictis longicornis, Myzus persicae* (green peach aphid), *Nephotettix* spp. (leafhoppers), *Nephotettix cinctipes* (green leafhopper), *Nilaparvata lugens* (brown planthopper), *Parlatoria pergandii* (chaff scale), *Parlatoria ziziphi* (ebony scale), *Peregrinus maidis* (corn delphacid), *Philaenus* spp. (spittlebugs), *Phylloxera vitifoliae* (grape phylloxera), *Physokermes piceae* (spruce bud scale), *Planococcus* spp. (mealybugs), *Pseudococcus* spp. (mealybugs), *Pseudococcus brevipes* (pine apple mealybug), *Quadraspidiotus perniciosus* (San Jose scale), *Rhapalosiphum* spp. (aphids), *Rhapalosiphum maida* (corn leaf aphid), *Rhapalosiphum padi* (oat bird-cherry aphid), *Saissetia* spp. (scales), *Saissetia oleae* (black scale), *Schizaphis graminum* (greenbug), *Sitobion avenae* (English grain aphid), *Sogatella furcifera* (white-backed planthopper), *Therioaphis* spp. (aphids), *Toumeyella* spp. (scales), *Toxoptera* spp. (aphids), *Trialeurodes* spp. (whiteflies), *Trialeurodes vaporariorum* (greenhouse whitefly), *Trialeurodes abutiloneus* (bandedwing whitefly), *Unaspis* spp. (scales), *Unaspis yanonensis* (arrowhead scale), and *Zulia entreriana*.

In another embodiment, the invention disclosed in this document may be used to control Hymenoptera (ants, wasps, and bees). A non-exhaustive list of such pests includes, but is not limited to, *Acromyrrmex* spp., *Athalia rosae, Atta* spp. (leafcutting ants), *Camponotus* spp. (carpenter ants), *Diprion* spp. (sawflies), *Formica* spp. (ants), *Iridomyrmex humilis* (Argentine ant), *Monomorium* spp., *Monomorium minumum* (little black ant), *Monomorium pharaonis* (Pharaoh ant), *Neodiprion* spp. (sawflies), *Pogonomyrmex* spp. (harvester ants), *Polistes* spp. (paper wasps), *Solenopsis* spp. (fire ants), Tapoinoma sessile (odorous house ant), *Tetranomorium* spp. (pavement ants), *Vespula* spp. (yellow jackets), and *Xylocopa* spp. (carpenter bees).

In another embodiment, the invention disclosed in this document may be used to control Isoptera (termites). A non-exhaustive list of such pests includes, but is not limited to, *Coptotermes* spp., *Coptotermes curvignathus*, *Coptotermes frenchii*, *Coptotermes formosanus* (Formosan subterranean termite), *Cornitermes* spp. (nasute termites), *Cryptotermes* spp. (drywood termites), *Heterotermes* spp. (desert subterranean termites), *Heterotermes aureus*, *Kalotermes* spp. (drywood termites), *Incistitermes* spp. (drywood termites), *Macrotermes* spp. (fungus growing termites), *Marginitermes* spp. (drywood termites), *Microcerotermes* spp. (harvester termites), *Microtermes obesi*, *Procornitermes* spp., *Reticulitermes* spp. (subterranean termites), *Reticulitermes banyulensis*, *Reticulitermes grassei*, *Reticulitermes flavipes* (eastern subterranean termite), *Reticulitermes hageni*, *Reticulitermes hesperus* (western subterranean termite), *Reticulitermes santonensis*, *Reticulitermes speratus*, *Reticulitermes tibialis*, *Reticulitermes virginicus*, *Schedorhinotermes* spp., and *Zootermopsis* spp. (rotten-wood termites).

In another embodiment, the invention disclosed in this document may be used to control Lepidoptera (moths and butterflies). A non-exhaustive list of such pests includes, but is not limited to, *Achoea janata*, *Adoxophyes* spp., *Adoxophyes orana*, *Agrotis* spp. (cutworms), *Agrotis ipsilon* (black cutworm), *Alabama argillacea* (cotton leafworm), *Amorbia cuneana*, *Amyelosis transitella* (navel orangeworm), *Anacamptodes defectaria*, *Anarsia lineatella* (peach twig borer), *Anomis sabulifera* (jute looper), *Anticarsia gemmatalis* (velvetbean caterpillar), *Archips argyrospila* (fruittree leafroller), *Archips rosana* (rose leaf roller), *Argyrotaenia* spp. (tortricid moths), *Argyrotaenia citrana* (orange tortrix), *Autographa gamma*, *Bonagota cranaodes*, *Borbo cinnara* (rice leaf folder), *Bucculatrix thurberiella* (cotton leafperforator), *Caloptilia* spp. (leafminers), *Capua reticulana*, *Carposina niponensis* (peach fruit moth), *Chilo* spp., *Chlumetia transversa* (mango shoot borer), *Choristoneura rosaceana* (obliquebanded leafroller), *Chrysodeixis* spp., *Cnaphalocerus medinalis* (grass leafroller), *Colias* spp., *Conpomorpha cramerella*, *Cossus cossus* (carpenter moth), *Crambus* spp. (Sod webworms), *Cydia funebrana* (plum fruit moth), *Cydia molesta* (oriental fruit moth), *Cydia nignicana* (pea moth), *Cydia pomonella* (codling moth), *Darna diducta*, *Diaphania* spp. (stem borers), *Diatraea* spp. (stalk borers), *Diatraea saccharalis* (sugarcane borer), *Diatraea graniosella* (southwestern corn borer), *Earias* spp. (bollworms), *Earias insulata* (Egyptian bollworm), *Earias vitella* (rough northern bollworm), *Ecdytopopha aurantianum*, *Elasmopalpus lignosellus* (lesser cornstalk borer), *Epiphysias postruttana* (light brown apple moth), *Ephestia* spp. (flour moths), *Ephestia cautella* (almond moth), *Ephestia elutella* (tobacco moth), *Ephestia kuehniella* (Mediterranean flour moth), *Epimeces* spp., *Epinotia aporema*, *Erionota thrax* (banana skipper), *Eupoecilia ambiguella* (grape berry moth), *Euxoa auxiliaris* (army cutworm), *Feltia* spp. (cutworms), *Gortyna* spp. (stemborers), *Grapholita molesta* (oriental fruit moth), *Hedylepta indicata* (bean leaf webber), *Helicoverpa* spp. (noctuid moths), *Helicoverpa armigera* (cotton bollworm), *Helicoverpa zea* (bollworm/corn earworm), *Heliothis* spp. (noctuid moths), *Heliothis virescens* (tobacco budworm), *Hellula undalis* (cabbage webworm), *Indarbela* spp. (root borers), *Keiferia lycopersicella* (tomato pinworm), *Leucinodes orbonalis* (eggplant fruit borer), *Leucoptera malifoliella*, *Lithocollectis* spp., *Lobesia botrana* (grape fruit moth), *Loxagrotis* spp. (noctuid moths), *Loxagrotis albicosta* (western bean cutworm), *Lymantria dispar* (gypsy moth), *Lyonetia clerkella* (apple leaf miner), *Mahasena corbetti* (oil palm bagworm), *Malacosoma* spp. (tent caterpillars), *Mamestra brassicae* (cabbage armyworm), *Maruca testulalis* (bean pod borer), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia*, *Pandemis cerasana* (common currant tortrix), *Pandemis heparana* (brown apple tortrix), *Papilio demodocus*, *Pectinophora gossypiella* (pink bollworm), *Peridroma* spp. (cutworms), *Peridroma saucia* (variegated cutworm), *Perileucoptera coffeella* (white coffee leafminer), *Phthorimaea operculella* (potato tuber moth), *Phyllocnisitis citrella*, *Phyllonorycter* spp. (leafminers), *Pieris rapae* (imported cabbageworm), *Plathypena scabra*, *Plodia interpunctella* (Indian meal moth), *Plutella xylostella* (diamondback moth), *Polychrosis viteana* (grape berry moth), *Prays endocarpa*, *Prays oleae* (olive moth), *Pseudaletia* spp. (noctuid moths), *Pseudaletia unipunctata* (armyworm), *Pseudoplusia includens* (soybean looper), *Rachiplusia nu*, *Scirpophaga incertulas*, *Sesamia* spp. (stemborers), *Sesamia inferens* (pink rice stem borer), *Sesamia nonagrioides*, *Setora nitens*, *Sitotroga cerealella* (Angoumois grain moth), *Sparganothis pilleriana*, *Spodoptera* spp. (armyworms), *Spodoptera exigua* (beet armyworm), *Spodoptera frugiperda* (fall armyworm), *Spodoptera oridania* (southern armyworm), *Synanthedon* spp. (root borers), *Thecla basilides*, *Thermisia gemmatalis*, *Tineola bisselliella* (webbing clothes moth), *Trichoplusia ni* (cabbage looper), *Tuta absoluta*, *Yponomeuta* spp., *Zeuzera coffeae* (red branch borer), and *Zeuzera pyrina* (leopard moth).

In another embodiment, the invention disclosed in this document may be used to control *Mallophaga* (chewing lice). A non-exhaustive list of such pests includes, but is not limited to, *Bovicola ovis* (sheep biting louse), *Menacanthus stramineus* (chicken body louse), and *Menopon gallinea* (common hen louse).

In another embodiment, the invention disclosed in this document may be used to control Orthoptera (grasshoppers, locusts, and crickets). A non-exhaustive list of such pests includes, but is not limited to, *Anabrus simplex* (Mormon cricket), *Gryllotalpidae* (mole crickets), *Locusta migratoria*, *Melanoplus* spp. (grasshoppers), *Microcentrum retinerve* (angularwinged katydid), *Pterophylla* spp. (katydids), *Schistocerca gregaria*, *Scudderia furcata* (forktailed bush katydid), and *Valanga nigricornis* (short horned grasshopper).

In another embodiment, the invention disclosed in this document may be used to control Phthiraptera (sucking lice). A non-exhaustive list of such pests includes, but is not limited to, *Haematopinus* spp. (cattle and hog lice), *Linognathus ovillus* (sheep louse), *Pediculus humanus capitis* (human body louse), *Pediculus humanus humanus* (human body lice), and *Pthirus pubis* (crab louse).

In another embodiment, the invention disclosed in this document may be used to control Siphonaptera (fleas). A non-exhaustive list of such pests includes, but is not limited to, *Ctenocephalides* canis (dog flea), *Ctenocephalides* felts (cat flea), and *Pulex* irritans (human flea).

In another embodiment, the invention disclosed in this document may be used to control Thysanoptera (thrips). A non-exhaustive list of such pests includes, but is not limited to, *Frankliniella fusca* (tobacco thrips), *Frankliniella occidentalis* (western flower thrips), *Frankliniella shultzei*, *Frankliniella williamsi* (corn thrips), *Heliothrips haemorrhaidalis* (greenhouse thrips), *Riphiphorothrips cruentatus*, *Scirtothrips* spp., *Scirtothrips citri* (citrus thrips), *Scirtothrips dorsalis* (yellow tea thrips), *Taeniothrips rhopalantennalis*, and *Thrips* spp.

In another embodiment, the invention disclosed in this document may be used to control *Thysanura* (bristletails). A non-exhaustive list of such pests includes, but is not limited to, *Lepisma* spp. (silverfish) and *Thermobia* spp. (firebrats).

In another embodiment, the invention disclosed in this document may be used to control *Acarina* (mites and ticks). A non-exhaustive list of such pests includes, but is not limited to, *Acarapsis woodi* (tracheal mite of honeybees), *Acarus* spp. (food mites), *Acarus siro* (grain mite), *Aceria mangiferae* (mango bud mite), *Aculops* spp., *Aculops lycopersici* (tomato russet mite), *Aculops pelekasi, Aculus pelekassi, Aculus schlechtendali* (apple rust mite), *Amblyomma americanum* (lone star tick), *Boophilus* spp. (ticks), *Brevipalpus obovatus* (privet mite), *Brevipalpus phoenicis* (red and black flat mite), *Demodex* spp. (mange mites), *Dermacentor* spp. (hard ticks), *Dermacentor variabilis* (American dog tick), *Dermatophagoides pteronyssinus* (house dust mite), *Eotetranycus* spp., *Eotetranychus carpini* (yellow spider mite), *Epitimerus* spp., *Eriophyes* spp., *Ixodes* spp. (ticks), *Metatetranycus* spp., *Notoedres cati, Oligonychus* spp., *Oligonychus coffee, Oligonychus ilicus* (southern red mite), *Panonychus* spp., *Panonychus citri* (citrus red mite), *Panonychus ulmi* (European red mite), *Phyllocoptruta oleivora* (citrus rust mite), *Polyphagotarsonemun latus* (broad mite), *Rhipicephalus sanguineus* (brown dog tick), *Rhizoglyphus* spp. (bulb mites), *Sarcoptes scabiei* (itch mite), *Tegolophus perseaflorae, Tetranychus* spp., *Tetranychus urticae* (two-spotted spider mite), and *Varroa destructor* (honey bee mite).

In another embodiment, the invention disclosed in this document may be used to control *Nematoda* (nematodes). A non-exhaustive list of such pests includes, but is not limited to, *Aphelenchoides* spp. (bud and leaf & pine wood nematodes), *Belonolaimus* spp. (sting nematodes), *Criconemella* spp. (ring nematodes), *Dirofilaria immitis* (dog heartworm), *Ditylenchus* spp. (stem and bulb nematodes), *Heterodera* spp. (cyst nematodes), *Heterodera zeae* (corn cyst nematode), *Hirschmanniella* spp. (root nematodes), *Hoplolaimus* spp. (lance nematodes), *Meloidogyne* spp. (root knot nematodes), *Meloidogyne incognita* (root knot nematode), *Onchocerca volvulus* (hook-tail worm), *Pratylenchus* spp. (lesion nematodes), *Radopholus* spp. (burrowing nematodes), and *Rotylenchus reniformis* (kidney-shaped nematode).

In another embodiment, the invention disclosed in this document may be used to control *Symphyla* (symphylans). A non-exhaustive list of such pests includes, but is not limited to, *Scutigerella immaculata.*

In another embodiment, the invention disclosed in this document may be used to control animal and human parasites. A non-exhaustive list of such pests includes, but is not limited to, arthropods such as mites (e.g., mesostigmatids, itch, mange, scabies, chiggers), ticks (e.g., soft-bodied and hard-bodied), lice (e.g., sucking, biting), fleas (e.g., dog flea, cat flea, oriental rat flea, human flea), true bugs (e.g., bed bugs, Triatomid bugs), bloodsucking adult flies (e.g., horn fly, horse fly, stable fly, black fly, deer fly, louse fly, tsetse fly, mosquitoes), and parasitic fly maggots (e.g., bot fly, blow fly, screwworm, cattle grub, fleeceworm); helminths such as nematodes (e.g., threadworm, lungworm, hookworm, whipworm, nodular worm, stomach worm, round worm, pinworm, heartworm), cestodes (e.g., tapeworms) and trematodes (e.g., liver fluke, blood fluke); protozoa such as coccidia, trypanosomes, trichomonads, amoebas and plasmodia; acanthocephalans such as thorny-headed worms (e.g., lingulatulida); and pentastomids such as tongueworms.

Detailed information regarding pests may be found in the "Handbook of Pest Control—The Behavior, Life History, and Control of Household Pests" by Arnold Mallis, 9$^{th}$ Edition, copyright 2004 by GIE Media Inc, which is expressly incorporated by reference herein.

The present invention contemplates all vehicles by which the composition of the present invention can be formulated for delivery and use as a pesticide composition, including solutions, suspensions, emulsions, wettable powders and water dispersible granules, emulsifiable concentrates, granules, dusts, baits, and the like. Compositions suitable for administration to vertebrates or man include preparations suitable for oral, parenteral, percutaneous, e.g. pour-on, or topical administration.

Compositions for oral administration comprise one or more of the compounds of general formula (I-A) or (I-B) in association with pharmaceutically acceptable carriers or coatings and include, for example, tablets, pills, capsules, pastes, gels, drenches, medicated feeds, medicated drinking water, medicated dietary supplements, slow-release boluses or other slow-release devices intended to be retained within the gastrointestinal tract. Any of these may incorporate active ingredient contained within microcapsules or coated with acid-labile or alkali-labile or other pharmaceutically acceptable enteric coatings. Feed premixes and concentrates containing compounds of the present invention for use in preparation of medicated diets, drinking water or other materials for consumption by animals may also be used.

Compositions for parenteral administration include solutions, emulsions or suspensions in any suitable pharmaceutically acceptable vehicle and solid or semisolid subcutaneous implants or pellets designed to release active ingredient over a protracted period and may be prepared and made sterile in any appropriate manner known to the art.

Compositions for percutaneous and topical administration include sprays, dusts, baths, dips, showers, jets, greases, shampoos, creams, wax-smears, or pour-on preparations and devices (e.g. ear tags) attached externally to animals in such a way as to provide local or systemic arthropod control.

Typically, formulations for application to plants, seeds, or soil are applied following dilution of the concentrated formulation with water as aqueous solutions, suspensions or emulsions, or combinations thereof. Such solutions, suspensions or emulsions are produced from water-soluble, water-suspended or water-suspendable, water-emulsified or water-emulsifiable formulations or combinations thereof which are solids, including and usually known as wettable powders or water dispersible granules; or liquids including and usually known as emulsifiable concentrates, aqueous suspensions or suspension concentrates, and aqueous emulsions or emulsions in water, or mixtures thereof such as suspension-emulsions. As will be readily appreciated, any materials to which this composition can be added may be used, provided they yield the desired utility without significant interference with the desired activity of the pesticidally active ingredients as pesticidal agents.

Wettable powders, which may be compacted to form water dispersible granules, comprise an intimate mixture of one or more of the pesticidally active ingredients, an inert carrier and surfactants. The concentration of the pesticidally active ingredient in the wettable powder is usually from about 10 percent to about 90 percent by weight based on the total weight of the wettable powder, more preferably about 25 weight percent to about 75 weight percent. In the preparation of wettable powder formulations, the pesticidally active ingredients can be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the pesticidally active ingredient comprise a convenient concentration, such as from about 10 weight percent to about 50 weight percent of the pesticidally active ingredient, in a suitable liquid, based on the total weight of the concentrate. The pesticidally active ingredients are dissolved in an inert carrier, which is either a water miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters esterified with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts of sulfated polyglycol ethers and appropriate salts of phosphated polyglycol ether.

Representative organic liquids which can be employed in preparing emulsifiable concentrates are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides; and glycol ethers such as the n-butyl ether, ethyl ether or methyl ether of diethylene glycol, and the methyl ether of triethylene glycol and the like. Mixtures of two or more organic liquids may also be employed in the preparation of the emulsifiable concentrate. Surface-active emulsifying agents are typically employed in liquid formulations and in an amount of from 0.1 to 20 percent by weight based on the combined weight of the emulsifying agents. The formulations can also contain other compatible additives, for example, plant growth regulators and other biologically active compounds used in agriculture.

Aqueous suspensions comprise suspensions of one or more water-insoluble pesticidally active ingredients dispersed in an aqueous vehicle at a concentration in the range from about 5 to about 70 weight percent, based on the total weight of the aqueous suspension. Suspensions are prepared by finely grinding one or more of the pesticidally active ingredients, and vigorously mixing the ground material into a vehicle comprised of water and surfactants chosen from the same types discussed above. Other components, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

Aqueous emulsions comprise emulsions of one or more water-insoluble pesticidally active ingredients emulsified in an aqueous vehicle at a concentration typically in the range from about 5 to about 70 weight percent, based on the total weight of the aqueous emulsion. If the pesticidally active ingredient is a solid it must be dissolved in a suitable water-immiscible solvent prior to the preparation of the aqueous emulsion. Emulsions are prepared by emulsifying the liquid pesticidally active ingredient or water-immiscible solution thereof into an aqueous medium typically with inclusion of surfactants that aid in the formation and stabilization of the emulsion as described above. This is often accomplished with the aid of vigorous mixing provided by high shear mixers or homogenizers.

The compositions of the present invention can also be granular formulations, which are particularly useful for applications to the soil. Granular formulations usually contain from about 0.5 to about 10 weight percent, based on the total weight of the granular formulation of the pesticidally active ingredient(s), dispersed in an inert carrier which consists entirely or in large part of coarsely divided inert material such as attapulgite, bentonite, diatomite, clay or a similar inexpensive substance. Such formulations are usually prepared by dissolving the pesticidally active ingredients in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts can be prepared by intimately mixing one or more of the pesticidally active ingredients in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the pesticidally active ingredients onto the target site such as a crop or organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters of sulfosuccinic acids, ethoxylated organosilicones, ethoxylated fatty amines and blends of surfactants with mineral or vegetable oils.

The formulations may optionally include combinations that contain one or more other pesticidal compounds. Such additional pesticidal compounds may be fungicides, insecticides, nematicides, miticides, arthropodicides, bactericides, plant growth stimulators or regulators, nitrification inhibitors, nutrients, or combinations thereof that are compatible with the compounds of the present invention in the medium selected for application, and not antagonistic to the activity of the present compounds. The compounds of the present invention, and the pesticidal compound in the combination can generally be present in a weight ratio of from 1:100 to 100:1.

The compounds disclosed in this invention can be in the form of pesticidally acceptable acid addition salts.

By way of non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic acids.

Additionally, by way of non-limiting example, an acid function can form salts including those derived from alkali or alkaline earth metals and those derived from ammonia and amines Examples of preferred cations include sodium, potassium, magnesium, and aminium cations.

The salts are prepared by contacting the free base form with a sufficient amount of the desired acid to produce a salt. The free base forms may be regenerated by treating the salt with a suitable dilute aqueous base solution such as dilute aqueous NaOH, potassium carbonate, ammonia, and sodium bicarbonate. As an example, in many cases, a pesticide is modified to a more water soluble form e.g. 2,4-dichlorophenoxy acetic acid dimethyl amine salt is a more water soluble form of 2,4-dichlorophenoxy acetic acid, a well known herbicide.

The compounds disclosed in this invention can also form stable complexes with solvent molecules that remain intact after the non-complexed solvent molecules are removed from the compounds. These complexes are often referred to as "solvates".

Certain compounds disclosed in this document can exist as one or more stereoisomers. The various stereoisomers include geometric isomers, diastereomers, and enantiomers. Thus, the compounds disclosed in this invention include racemic mixtures, individual stereoisomers, and optically active mixtures. It will be appreciated by those skilled in the art that one stereoisomer may be more active than the others. Individual stereoisomers and optically active mixtures may be obtained by selective synthetic procedures, by conventional synthetic procedures using resolved starting materials, or by conventional resolution procedures.

The compounds of the present invention can also be combined with other agricultural fungicides to form fungicidal mixtures and synergistic mixtures thereof. The fungicidal compounds of the present invention are often applied in conjunction with one or more other fungicides to control a wider variety of undesirable diseases. When used in conjunction with other fungicide(s), the presently claimed compounds can be formulated with the other fungicide(s), tank mixed with the other fungicide(s) or applied sequentially with the other fungicide(s). Such other fungicides include but are not limited to 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, BYF 1047, calcium polysulfide, captafol, captan, carbendazim, carboxin, carpropamid, carvone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, coumarin, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M,dinobuton, dinocap, diphenylamine, dithianon, dodemorph, dodemorph acetate, dodine, dodine free base, edifenphos, enestrobin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, isopyrazam, isotianil, kasugamycin, kasugamycin hydrochloride hydrate, kresoxim-methyl, mancopper, mancozeb, mandipropamid, maneb, mepanipyrim, mepronil, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxinecopper, oxpoconazole fumarate, oxycarboxin, pefurazoate, penconazole, pencycuron, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z071, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila*, *Fusarium oxysporum*, *Gliocladium* spp., *Phlebiopsis gigantea*, *Streptomyces griseoviridis*, *Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chloro-phenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenyl-itaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, XRD-563, and zarilamid, IK-1140, and any combinations thereof.

Additionally, the compounds of the present invention can be combined with other pesticides, including insecticides, nematicides, miticides, arthropodicides, bactericides or combinations thereof that are compatible with the compounds of the present invention in the medium selected for application, and not antagonistic to the activity of the present compounds to form pesticidal mixtures and synergistic mixtures thereof. The pesticidal compounds of the present invention are often applied in conjunction with one or more other insecticides, miticides, or other pesticides to control a wider variety of undesirable pests. When used in conjunction with other pesticides, the presently claimed compounds can be formulated with the other pesticide(s), tank mixed with the other pesticide(s) or applied sequentially with the other pesticide(s). Typical insecticides include, but are not limited to: antibiotic insecticides such as allosamidin and thuringiensin; macrocyclic lactone insecticides such as spinosad and spinetoram; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; diamide insecticides such as chlorantraniliprole, cyantraniliprole and flubendiamide; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, paradichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethyl-amine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; oxadiazolone insecticides such as metoxadiazone; phthalimide insecticides such as dialifos, phosmet and tetramethrin; pyrazole insecticides such as acetoprole, cyenopyrafen, ethiprole, fipronil, pyrafluprole, pyriprole, tebufenpyrad, tolfenpyrad and vaniliprole; pyrethroid ester insecticides such as acrinathrin, allethrin, bioallethrin, barthrin, bifenthrin, bioethanomethrin, cyclethrin, cyprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetramic acid insecticides such as spirotetramat; tetronic acid insecticides such as spiromesifen; thiourea insecticides such as diafenthiuron; urea insecticides such as flucofuron and sulcofuron; and unclassified insecticides such as closantel, copper naphthenate, crotamiton, EXD, fenazaflor, fenoxacrim, hydramethylnon, isoprothiolane, malonoben, metaflumizone, nifluridide, plifenate, pyridaben, pyridalyl, pyrifluquinazon, rafoxanide, sulfoxaflor, triarathene, triazamate, and any combinations thereof.

Additionally, the compounds of the present invention may be combined with herbicides that are compatible with the compounds of the present invention in the medium selected for application, and not antagonistic to the activity of the present compounds to form pesticidal mixtures and synergistic mixtures thereof. The pesticidal compounds of the present disclosure may be applied in conjunction with one or more herbicides to control a wide variety of undesirable plants, diseases, and pests. When used in conjunction with herbicides, the presently claimed compounds may be formulated with the herbicide(s), tank mixed with the herbicide(s) or applied sequentially with the herbicide(s). Typical herbicides include, but are not limited to: amide herbicides such as allidochlor, beflubutamid, benzadox, benzipram, bromobutide, cafenstrole, CDEA, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flampropand flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; thioamide herbicides such as chlorthiamid; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; benzothiazole herbicides such as benzazolin; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glufosinate-P, glyphosate and piperophos; phenoxy herbicides such as bromofenoxim, clomeprop, 2,4-DEB, 2,4-DEP, difenopenten, disul, erbon, etnipromid, fenteracol and trifopsime; oxadiazoline herbicides such as methazole, oxadiargyl, oxadiazon; oxazole herbicides such as fenoxasulfone; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecopropand mecoprop-P;

aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazole herbicides such as pyroxasulfone; benzoylpyrazole herbicides such as benzofenap, pyrasulfotole, pyrazolynate, pyrazoxyfen, and topramezone; phenylpyrazole herbicides such as fluazolate, nipyraclofen, pioxaden and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluoroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, indaziflam, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, ipfencarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as benzfendizone, bromacil, butafenacil, flupropacil, isocil, lenacil, saflufenacil and terbacil; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluoron, phenobenzuron, siduron, tetrafluoron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, metazosulfuron, nicosulfuron, orthosulfamuron, oxasulfuron, primisulfuron, propyrisulfuron, pyrazosulfuron, rimsulfuron, sulfometuron, sulfosulfuron and triflox ysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluoron and thidiazuron; and unclassified herbicides such as acrolein, allyl alcohol, aminocyclopyrachlor, azafenidin, bentazone, benzobicyclon, bicyclopyrone, buthidazole, calcium cyanamide, cambendichlor, chlorfenac, chlorfenprop, chlorflurazole, chlorflurenol, cinmethylin, clomazone, CPMF, cresol, cyanamide, ortho-dichlorobenzene, dimepiperate, endothal, fluoromidine, fluridone, fluorochloridone, flurtamone, fluthiacet, indanofan, methyl isothiocyanate, OCH, oxaziclomefone, pentachlorophenol, pentoxazone, phenylmercury acetate, prosulfalin, pyribenzoxim, pyriftalid, quinoclamine, rhodethanil, sulglycapin, thidiazimin, tridiphane, trimeturon, tripropindan and tritac.

The compounds of the present invention may have broad ranges of efficacy as pesticides. The exact amount of the active material to be applied is dependent not only on the specific active material being applied, but also on the particular action desired, the pathogen or pest to be controlled, and the stage of growth thereof, as well as the part of the plant, animal or other medium to be contacted with the compound. Thus, all the compounds, and formulations containing the same, may not be equally effective at similar concentrations or against the same pathogen and pest species.

The compounds are effective in use with plants in a phytologically acceptable amount. The term "phytologically acceptable amount" refers to an amount of a compound that kills or inhibits the pest or plant disease for which control is desired, but is not significantly toxic to the plant. This amount will generally be from about 0.1 to about 1000 parts per million (ppm), with 1 to 500 ppm being preferred.

The exact concentration of compound required varies with the pest or disease to be controlled, the type of formulation employed, the method of application, the particular plant or animal species, climate conditions, and the like. For fungicides, dilution and rate of application will depend upon the type of equipment employed, the method and frequency of application desired and diseases to be controlled, but the effective amount is usually from about 0.01 kilogram (kg) to about 20 kg of active ingredient (a.i.) per hectare (ha). As a foliar fungicide, a compound of the present invention is usually applied to growing plants at a rate of about 0.1 to about 5 and preferably from about 0.125 to about 0.5 kg per hectare.

As a seed-applied fungicide, the amount of toxicant coated on the seed is usually at a dosage rate of about 0.1 to about 250 grams (g) and preferably from about 1 to about 60 g per 100 kg of seed. As a soil fungicide, the chemical can be incorporated in the soil or applied to the surface of the soil or a rice nursery box usually at a rate of about 0.1 to about 5 kg per hectare.

The actual amount of insecticide or miticide to be applied to loci of pests is generally not critical and can readily be determined by those skilled in the art. In general, concentrations from about 10 g of pesticide per hectare to about 5000 g of pesticide per hectare are expected to provide good control.

The locus to which a pesticide is applied can be any locus inhabited by a pest, for example, vegetable crops, fruit and nut trees, grape vines, ornamental plants, domesticated animals, the interior or exterior surfaces of buildings, and the soil around buildings. Controlling pests generally means that pest populations, activity, or both, are reduced in a locus. This can come about when: pest populations are repulsed from a locus; when pests are incapacitated, partially or completely, temporarily or permanently, in or around a locus; or pests are exterminated, in whole or in part, in or around a locus. Of course a combination of these results can occur. Generally, pest populations, activity, or both are desirably reduced more than fifty percent, preferably more than 90 percent, even more preferably 99 percent.

Generally, with baits, the baits are placed in the ground where, for example, termites can come into contact with the bait. Baits can also be applied to a surface of a building, (horizontal, vertical, or slant, surface) where, for example, ants, termites, cockroaches, and flies, can come into contact with the bait.

Because of the unique ability of the eggs of some pests to resist pesticides repeated applications may be desirable to control newly emerged larvae.

Systemic movement of pesticides in plants may be utilized to control pests on one portion of the plant by applying the pesticides to a different portion of the plant, or to a location where the root system of a plant can uptake pesticides. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement or any other beneficial traits. Furthermore, such seed treatments with the invention disclosed in this document can further enhance the ability of a plant to better withstand stressful growing conditions. This results in a healthier, more vigorous plant, which can lead to higher yields at harvest time.

It should be readily apparent that the invention may be used with plants genetically transformed to express specialized traits, such as *Bacillus thuringiensis* or other insecticidal toxins, or those expressing herbicide resistance, or those with "stacked" foreign genes expressing insecticidal toxins, herbicide resistance, nutrition-enhancement or any other beneficial traits. An example of such a use is spraying such plants with the invention disclosed in this document.

The invention disclosed in this document may be suitable for controlling endoparasites and ectoparasites in the veterinary medicine sector or in the field of animal keeping. Compounds according to the invention are applied here in a known manner, such as by oral administration in the form of, for example, tablets, capsules, drinks, granules, by dermal application in the form of, for example, dipping, spraying, pouring on, spotting on, and dusting, and by parenteral administration in the form of, for example, an injection.

The invention disclosed in this document may also be employed advantageously in livestock keeping, for example, cattle, sheep, pigs, chickens, and geese. Suitable formulations may be administered orally to the animals with the drinking water or feed. The dosages and formulations that are suitable depend on the species.

It will be understood by those in the art that the efficacy of the compound on the foregoing fungi and insects establishes the general utility of the compounds as fungicides and insecticides.

Chromatography Definitions

Prep RP-HPLC (preparative reverse-phase high-performance liquid chromatography):

20 mm×250 mm S5 μm 120 Å YMC-AQ, or 50 mm×250 mm S10 μm 120 Å YMC-AQ column, using 0.1% v/v $H_3PO_4$ mixtures with MeCN (acetonitrile) as eluent;

HPLC (high performance liquid chromatography): acetonitrile/water solvent system over C8-C18 on silica gel support)

TLC (thin layer chromatography): $SiO_2$/glass plates, eluted with hexane, $Et_2O$ (diethyl ether), $CH_2Cl_2$ (dichloromethane), EtOAc (ethyl acetate), MeOH (methanol), or any useful mixture of these;

GC (gas chromatography);

GC-MS (gas chromatography-mass spectrometry)

LC-MS (liquid chromatography-mass spectrometry)

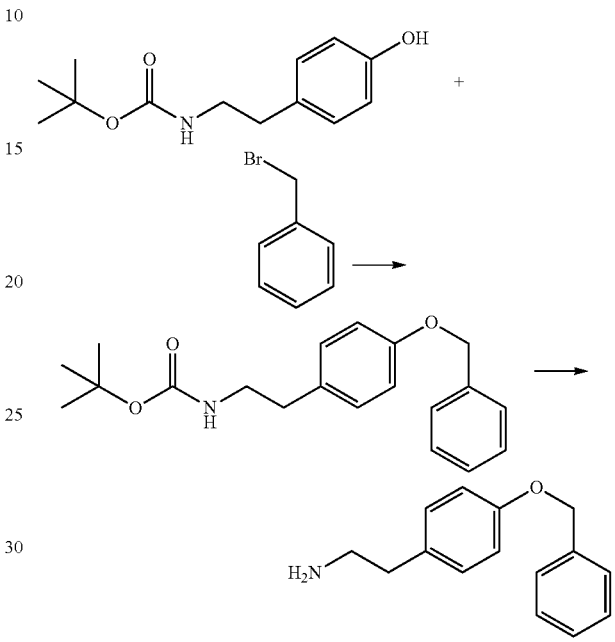

PREPARATION 1

2-(4-Benzyloxyphenyl)-ethylamine. To a suspension of potassium carbonate ($K_2CO_3$; 1.4 grams (g), 10.11 millimole (mmol)) in acetone (40 milliliters (mL)) was added bromomethylbenzene (1.73 g, 10.11 mmol) and tert-butyl 2-(4-hydroxyphenyl)ethylcarbamate (2 g, 8.4 mmol). The reaction mixture was heated at reflux for 15 hours (h) and then concentrated in vacuo. The residue was partitioned between diethyl ether ($Et_2O$) and water ($H_2O$), and the organic fraction was washed with brine, dried over sodium sulfate ($Na_2SO_4$), suction filtered, and concentrated in vacuo. The residue was purified by silica gel ($SiO_2$) flash chromatography with 25% $Et_2O$ in hexane to afford [2-(4-benzyloxyphenyl)-ethyl]-carbamic acid tert-butyl ester as a white solid (2.4 g). This was dissolved in $CH_2Cl_2$ (50 mL) and trifluoroacetic acid (5 mL) was added. After stirring 16 h, the solvent was removed in vacuo, and the residue was redissolved in $CH_2Cl_2$, washed with 1M sodium hydroxide (NaOH), dried ($Na_2SO_4$) and filtered. The solvent was removed in vacuo to yield 2-(4-benzyloxyphenyl)-ethylamine (1.5 g). This was used without purification in the next step.

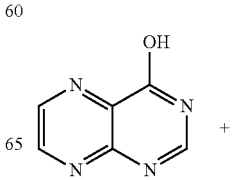

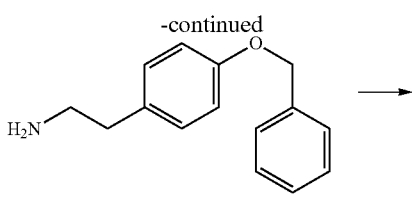

EXAMPLE 1

[2-(4-Benzyloxyphenyl)-ethyl]-pteridin-4-yl-amine. To a mixture of pteridin-4-ol (282 mg, 1.9 mmol) and 2-(4-benzyloxyphenyl)-ethylamine (476 mg, 2.1 mmol) and hexamethyldisilazane (5 mL) in a 25 mL round bottom flask, equipped with reflux condenser, drying tube and magnetic stir bar, was added ammonium sulfate (100 mg, 0.76 mmol). The mixture was heated to 114° C. overnight and then the solvent was removed in vacuo. The residue was suspended in $H_2O$ and filtered. The filter cake was dissolved in $CH_2Cl_2$, dried with $Na_2SO_4$, filtered, and concentrated in vacuo to provide [2-(4-benzyloxyphenyl)-ethyl]-pteridin-4-yl-amine as a white solid (501 mg): $^1H$ NMR (300 MHz) δ 9.01 (d, J=1.9 Hz, 1H), 8.81 (s, 1H), 8.61 (d, J=1.9 Hz, 1H), 7.49-7.29 (m, 6H), 7.25-7.15 (m, 3H), 6.96 (dd, J=6.8, 4.8 Hz, 2H), 5.06 (s, 2H), 3.93 (dd, J=13.2, 6.9 Hz, 2H), 3.00 (t, J=7.0 Hz, 2H); ESIMS m/z 358.1 ([M+H]$^+$).

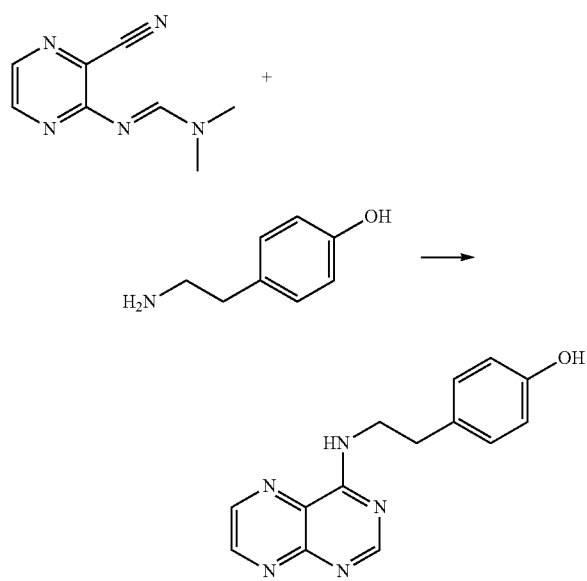

EXAMPLE 2

4-[2-(Pteridin-4-ylamino)-ethyl]-phenol. To a solution of N'-(3-cyanopyrazin-2-yl)-N,N-dimethylformamidine (prepared as in Albert and Ohta, *J. Chem. Soc.* C 1971, 3727-3730, which is expressly incorporated by reference herein; 2.0 g, 11.4 mmol) in ethyl alcohol (EtOH; 50 mL) was added 4-(2-aminoethyl)-phenol (4.7 g, 34 mmol) and acetic acid (3.9 mL, 4.1 g, 68 mmol). The solution was heated to reflux for 19 h, concentrated in vacuo, and the residue was slurried with $H_2O$ and suction filtered. The filter cake was washed with $H_2O$ and dried in a vacuum oven (80° C., 0.5 torr) to yield 4-[2-(pteridin-4-ylamino)-ethyl]-phenol (2.7 g) as a white solid: mp>210° C.; $^1H$ NMR (DMSO-$d_6$) δ 9.20 (s, 1H), 9.08 (s, 1H), 8.94 (s, 1H), 8.95 (t, J=6.0 Hz, 1H), 8.82 (s, 1H), 8.64 (s, 1H), 7.06 (d, J=8.5 Hz, 2H), 6.69 (d, J=8.2 Hz, 2H), 3.75 (t, J=6.2 Hz, 2H), 2.85 (t, J=7.6 Hz, 2H); ESIMS m/z 268 (M$^+$).

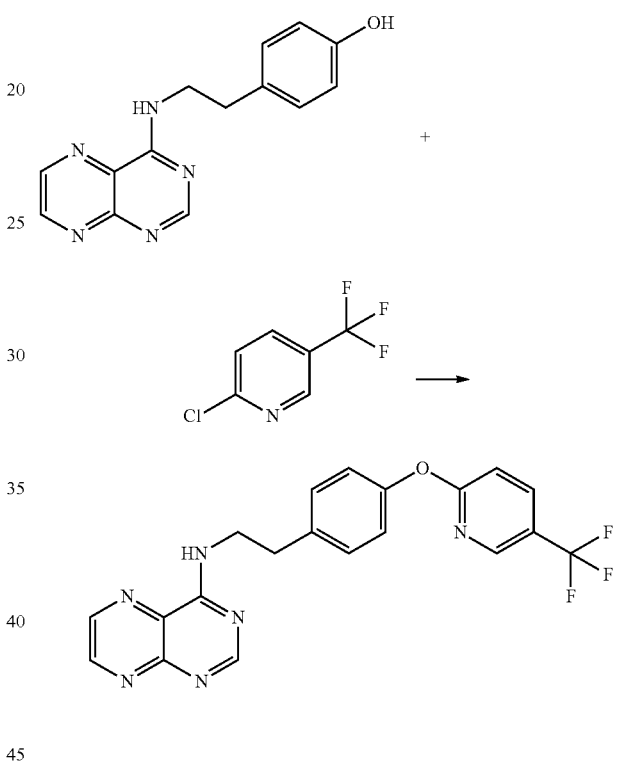

EXAMPLE 3

Pteridin-4-yl-{2-[4-(5-trifluoromethylpyridin-2-yloxy)-phenyl]-ethyl}-amine. To a solution of 4-[2-(pteridin-4-ylamino)ethyl]phenol (270 mg, 1.0 mmol) and dry DMSO (5 mL) was added 2-chloro-5-trifluoromethylpyridine (155 mg, 0.85 mmol) and $K_2CO_3$ (280 mg, 2.0 mmol). This mixture was heated to 80° C. for 3 h, cooled to ambient temperature, poured into $H_2O$ (20 mL) and extracted with $CH_2Cl_2$ (20 mL). The $CH_2Cl_2$ solution was washed with $H_2O$ (2×10 mL), dried with $Na_2SO_4$, and the solution was filtered. The solution was concentrated in vacuo, redissolved in a minimum volume of $CH_2Cl_2$ and treated with hexane to precipitate a solid. The solid was collected by filtration and dried under vacuum to afford pteridin-4-yl-{2-[4-(5-trifluoromethylpyridin-2-yloxy)-phenyl]-ethyl}-amine (310 mg) as an off-white solid: mp 147-150° C.; $^1H$ NMR (300 MHz, CDCl$_3$) δ 9.04 (d, J=1.9 Hz, 1H), 8.85 (s, 1H), 8.64 (d, J=1.9 Hz, 1H), 8.35 (d, J=5.2 Hz, 1H), 7.40-7.29 (m, 3H), 7.22 (dd, J=5.2, 0.8 Hz, 1H), 7.19-7.05 (m, 3H), 4.01 (dd, J=13.3, 7.0 Hz, 2H), 3.10 (t, J=7.1 Hz, 2H); ESIMS m/z 413 ([M+H]$^+$).

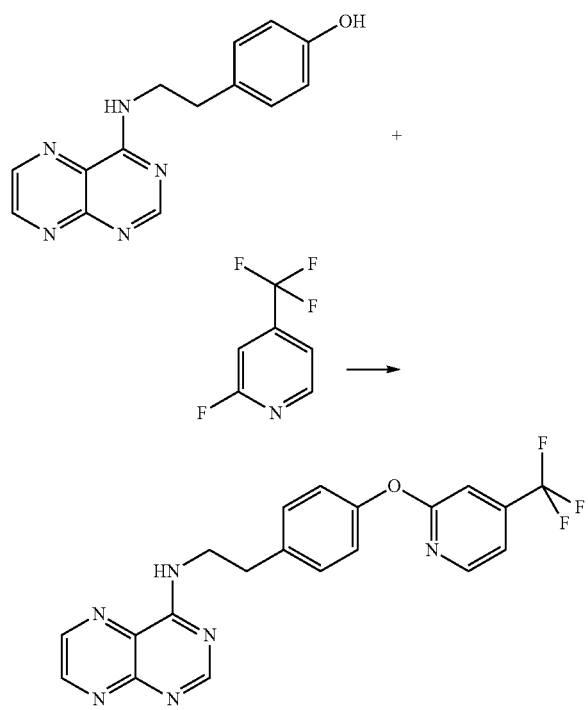

EXAMPLE 3Alt

Pteridin-4-yl-{2-[-(4-trifluoromethylpyridin-2-yloxy)-phenyl]-ethyl}-amine. To a solution of 4-[2-(pteridin-4-ylamino)ethyl]phenol (2.5 g, 9.3 mmol) and DMSO (20 mL) in a 100 mL round bottom flask, equipped with reflux condenser, drying tube and magnetic stir bar, was added 2-fluoro-4-(trifluoromethyl)pyridine (prepared as in U.S. Pat. No. 4,775,762, which is expressly incorporated by reference herein; 1.7 g, 10 mmol) and cesium carbonate ($Cs_2CO_3$; 3.7 g, 11.5 mmol). This mixture was heated to 57° C. for 16 h, then cooled to ambient temperature and poured into ice $H_2O$ (150 mL), precipitating an off-white solid. This was collected by suction filtration and the filter cake was washed with $H_2O$ and then pentane. The cake was then dissolved in $CH_2Cl_2$, dried with $Na_2SO_4$, and the solution was filtered. The solution was concentrated in vacuo to afford pteridin-4-yl-{2-[4-(4-trifluoromethylpyridin-2-yloxy)-phenyl]-ethyl}-amine (3.0 g) as an off-white solid: mp 147-149° C.; $^1$H NMR (300 MHz, $CDCl_3$) δ 9.04 (d, J=1.9 Hz, 1H), 8.85 (s, 1H), 8.64 (d, J=1.9 Hz, 1H), 8.35 (d, J=5.2 Hz, 1H), 7.40-7.29 (m, 3H), 7.22 (dd, J=5.2, 0.8 Hz, 1H), 7.19-7.05 (m, 3H), 4.01 (dd, J=13.3, 7.0 Hz, 2H), 3.10 (t, J=7.1 Hz, 2H); ESIMS m/z 413 ([M+H]$^+$).

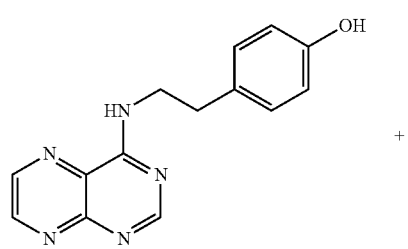

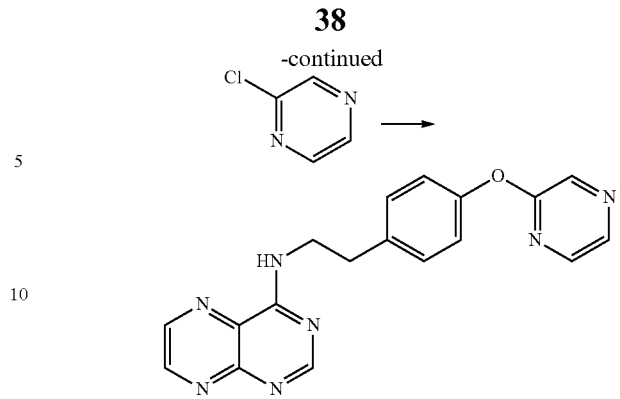

EXAMPLE 4

Pteridin-4-yl-{2-[4-(pyrazin-2-yloxy)-phenyl]-ethyl}-amine. To a solution of 4-[2-(pteridin-4-ylamino)ethyl]phenol (0.267 g, 1.0 mmol) and 2-chloropyrazine (0.114 g, 1.0 mmol) in anhydrous DMF (7 mL) was added 60% sodium hydride (NaH) in mineral oil (0.060 g, 1.5 mmol) portionwise. The mixture was stirred at 55° C. overnight and then at 70° C. for a total reaction time of 32 h. The solvent was removed in vacuo and the residue was suspended in $H_2O$. The solid was collected by suction filtration, washed with $H_2O$ and $Et_2O$, dried in a vacuum oven at 55° C. overnight to afford pteridin-4-yl-{2-[4-(pyrazin-2-yloxy)-phenyl]-ethyl}-amine (0.291 g, 84%) as a light brown solid: $^1$H NMR (300 MHz, $CDCl_3$) δ 9.02 (d, J=1.9 Hz, 1H), 8.82 (s, 1H), 8.63 (d, J=1.9 Hz, 1H), 8.43 (d, J=1.5 Hz, 1H), 8.26 (d, J=2.4 Hz, 1H), 8.10 (dd, J=2.4, 1.5 Hz, 1H), 7.33 (d, J=8.4 Hz, 2H), 7.13 (d, J=8.4 Hz, 2H), 3.99 (dd, J=13.6, 6.9 Hz, 2H), 3.08 (t, J=6.9 Hz, 2H); ESIMS m/z 346.24 ([M+H]$^+$).

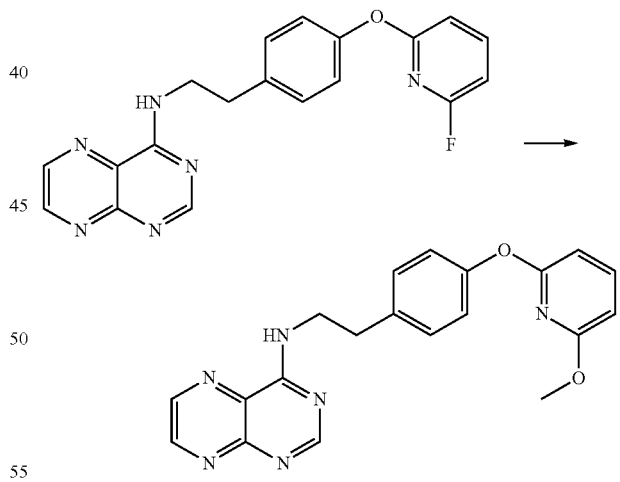

EXAMPLE 5

{2-[4-(6-Methoxypyridin-2-yloxy)-phenyl]-ethyl}-pteridin-4-yl-amine. {2-[4-(6-Fluoropyridin-2-yloxy)-phenyl]-ethyl}-pteridin-4-ylamine (200 mg, 0.55 mmol) was dissolved in 4 mL dry DMSO and treated with sodium methoxide (300 mg, 5.5 mmol, 10 eq) and stirred for 20 h at 25° C. The mixture was poured into $H_2O$ (15 mL) and extracted with $CH_2Cl_2$ (2×25 ml). The pooled $CH_2Cl_2$ extracts were washed with $H_2O$ and brine, dried ($Na_2SO_4$), filtered, and evaporated. The gummy residue was dissolved in a minimum quantity of CH$_2$Cl$_2$ and treated with hexane to precipitate the product as a solid that was collected by suction filtration, washed with hexane and dried in vacuo to afford {2-[4-(6-methoxypyridin-2-yloxy)-phenyl]-ethyl}-pteridin-4-yl-amine (139 mg) as a tan solid: mp 152-153° C.; $^1$H NMR (DMSO-d$_6$) δ 9.09 (s, 1H), 9.00 (t, J=5.9 Hz, 1H), 8.82 (s, 1H), 8.63 (s, 1H), 7.70 (t, J=8.0 Hz, 1H), 7.30 (d, J=8.3 Hz, 2H), 7.05 (d, J=8.4 Hz, 2H), 6.51 (d, J=8.0 Hz, 2H), 6.36 (d, J=7.7 Hz, 2H), 3.83 (m, 2H), 3.65 (s, 3H), 3.00 (m, 2H); ESIMS m/z 375 ([M+H]$^+$).

Also prepared by Example 5.

Pteridin-4-yl-(2-{4-[6-(2,2,2-trifluoroethoxy)-pyridin-2-yloxy]-phenyl}-ethyl)-amine, from sodium 2,2,2-trifluoroethoxide, prepared by treatment of 2,2,2-trifluoroethanol with sodium hydride.

{2-[4-(6-Ethoxypyridin-2-yloxy)-phenyl]-ethyl}-pteridin-4-yl-amine, from sodium ethoxide, prepared by treatment of ethanol with sodium hydride.

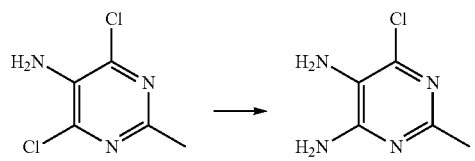

PREPARATION 2

6-Chloro-4,5-diamino-2-methylpyrimidine. A 200 mL stainless steel Parr vessel was loaded with 5-amino-4,6-dichloro-2-methylpyrimidine (7.2 g, 40 mmol) and 2 M ammonia in isopropanol (100 mL), and then was sealed and heated at 150° C. for 16 h. HPLC analysis indicated complete conversion. The mixture was concentrated in vacuo, and the residue was suspended in a mixture of H$_2$O (10 mL) and isopropanol (35 mL). This was stirred at 50° C. for 1 h and then was cooled to room temperature. The precipitate was collected by suction filtration, washed sparingly with isopropanol, then air dried on the filter to afford 6-chloro-4,5-diamino-2-methylpyrimidine (5.8 g, 91%) as a brown powder, which was used without further purification in the next step.

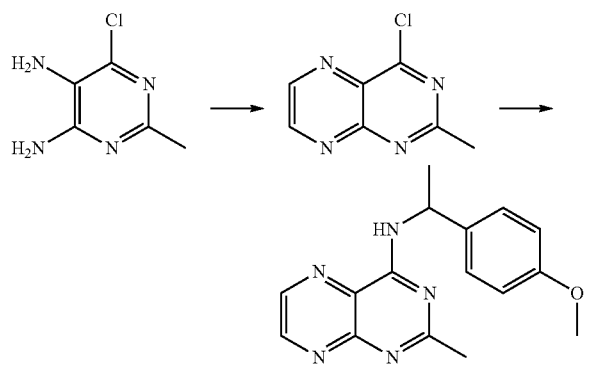

EXAMPLE 6

[1-(4-Methoxyphenyl)ethyl]-2-methylpteridin-4-yl-amine. A mixture of 6-chloro-4,5-diamino-2-methylpyrimidine (317 mg, 2.0 mmol) and 1,4-dioxane-2,3-diol (240 mg, 2.0 mmol) in EtOH (15 mL) was stirred at 25° C. for 1 h. TLC analysis (1:1 hexane/EtOAc on SiO$_2$) indicated complete consumption of starting material. 1-(4-Methoxyphenyl)-ethylamine (332 mg, 2.2 mmol) and triethylamine (Et$_3$N, 0.3 mL, 2.2 mmol) were added, and the reaction was stirred overnight. The majority of solvent was removed in vacuo and the residue was partitioned between EtOAc and H$_2$O. The organic layer was concentrated in vacuo to leave a brown residue that was purified by column chromatography over SiO$_2$, eluting with 2:1 EtOAc/hexane, then 100% EtOAc to afford [1-(4-methoxyphenyl)ethyl]-2-methylpteridin-4-yl-amine (126 mg) as a brown oil.

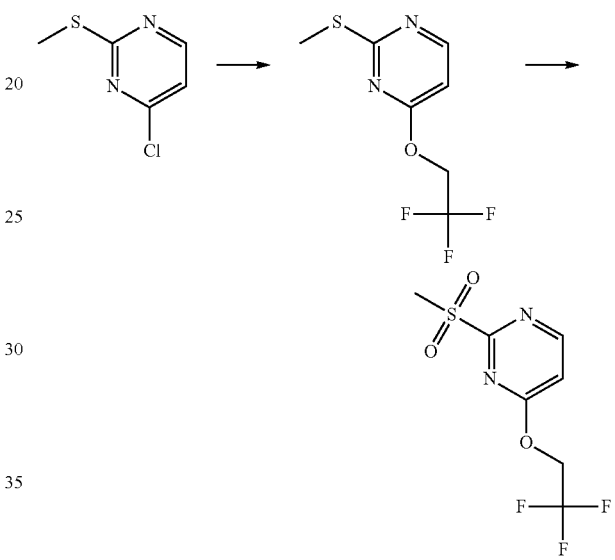

PREPARATION 3

1. 2-Methylthio-4-(2,2,2)-trifluoroethoxypyrimidine. To a suspension of 60% NaH (524 mg, 130.1 mmol) in DMSO (30 mL) was added 2,2,2-trifluoroethanol (1.31 g, 130.1 mmol). The reaction mixture was stirred 0.5 h at 25° C. and then 4-chloro-2-(methylthio)pyrimidine (2.0 g, 12.5 mmol) was added and stirred for 16 h. The reaction was diluted with H$_2$O and extracted with Et$_2$O. The Et$_2$O layer was washed with brine, concentrated in vacuo, and filtered through SiO$_2$ to yield 2.16 g of yellow oil which appeared to be 60% pure by HPLC and was used without further purification in the following step. 2. 2-Methylsulfonyl-4-(2,2,2)-trifluoroethoxypyrimidine. To a solution of 1.0 g, (4.46 mmol) of the product from Preparation 3, Step 1, in CH$_2$Cl$_2$ (5 mL), was added meta-chloroperoxybenzoic acid (MCPBA; 1.6 g, 6.7 mmol) in CH$_2$Cl$_2$ (6 mL). After 3 h, the reaction mixture was diluted with CH$_2$Cl$_2$ (20 mL) and washed with saturated aqueous sodium bicarbonate (NaHCO$_3$) solution. The organic layer was dried (Na$_2$SO$_4$), filtered and concentrated in vacuo to yield 2-methylsulfonyl-4-(2,2,2)-trifluoroethoxypyrimidine (1.3 g, 70% pure by LC). This was used without further purification.

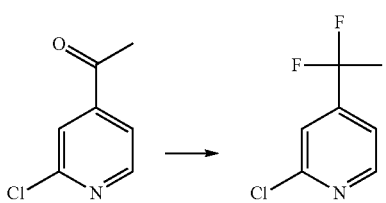

PREPARATION 4

2-Chloro-4-(1,1-difluoroethyl)-pyridine. To a solution of 2-chloro-4-acetylpyridine (2.6 g, 17.2 mmol) in $CH_2Cl_2$ (50 mL) was added diethylamino-sulfurtrifluoride (8 mL, 60 mmol) at 25° C. and the mixture was stirred for 16 h. The reaction was quenched by addition of saturated aqueous $NaHCO_3$ dropwise at 0° C. After separation of the two phases, the organic phase was dried over $Na_2SO_4$, filtered, and concentrated in vacuo. The residue was purified by column chromatography over $SiO_2$ with 10% EtOAc in hexane to yield 2-chloro-4-(1,1-difluoroethyl)pyridine (1.72 g) as a light brown oil: EIMS m/z 177 ([M]+).

Also prepared by this method:

2-Bromo-6-(1,1-difluoroethyl)-pyridine, from 1-(6-bromo-pyridin-2-yl)-ethanone. EIMS m/z 222 ([M]+).

2-Chloro-4-difluoromethylpyridine, from 2-chloropyridine-4-carbaldehyde. EIMS m/z 163 ([M]+).

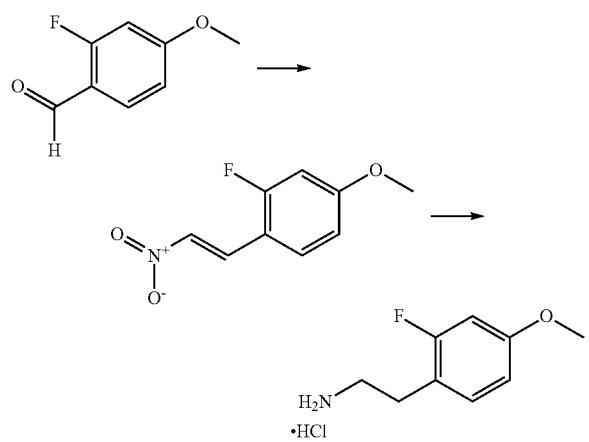

PREPARATION 5

1. 2-Fluoro-4-methoxy-1-((E)-2-nitrovinyl)benzene. A solution of 2-fluoro-4-methoxybenzaldehyde (5.0 g, 33 mmol) and ammonium acetate (1.0 g, 13 mmol) in nitromethane (40 mL) was heated on a steam bath for 2.5 h. The reaction mixture was concentrated under reduced pressure, and the sticky residue was partitioned between $CH_2Cl_2$ and $H_2O$. The organic layer was washed with half-saturated brine, dried ($MgSO_4$), filtered, and concentrated. The residue was triturated in hexane and the solid was filtered and washed with hexane and dried to give 2-fluoro-4-methoxy-1-(E)-2-nitrovinyl)benzene (5.57 g) as an orange solid: mp 80-82° C.; $^1H$ NMR ($CDCl_3$): δ 8.02 (d, J=13.5 Hz, 1H), 7.66 (d, J=13.5 Hz, 1H), 7.43 (m, 1H), 6.68-6.80 (m, 2H), 3.87 (s, 3H); EIMS m/z 197 ([M]+). This material was used in the next step without additional purification.

2. 2-(2-Fluoro-4-methoxyphenyl)ethylamine hydrochloride. Under a nitrogen atmosphere, 2-fluoro-4-methoxy-1-(E)-2-nitrovinyl)benzene (26.5 g, 134.5 mmol) was added in portions to a suspension of $LiAlH_4$ (16 g, 195 mmol) in THF (1 L) at 0° C. The mixture then was heated at reflux, and after 3.5 h, the reaction mixture was cooled to 0° C. and quenched carefully with $H_2O$ (34.6 mL) and 10% aqueous NaOH (28 mL). After removal of green precipitates by suction filtration, the filtrate was dried over $MgSO_4$, filtered and evaporated under reduced pressure. The oily residue was dissolved in EtOAc (150 mL) and then conc. HCl was added to adjust the pH to approximately 1. $Et_2O$ (1 L) was added with stirring and the solid was collected by suction filtration and washed with a small amount of acetone, then dried under vacuum to give 12.3 g of 2-(2-fluoro-4-methoxyphenyl)ethylamine hydrochloride as a white solid, mp 162-165° C. The filtrate was concentrated under reduced pressure, and the residue was dried azeotropically by suspending in toluene and concentrating in vacuo. The residue was dissolved in methanol, and the solution was diluted with EtOAc to precipitate additional product. The second crop was collected by suction filtration and washed with ethyl acetate, affording another 7.3 g of product. The total yield was 19.6 g (72%). $^1H$ NMR ($CDCl_3$): δ 8.29 (br, 3H), 7.24 (t, J=8.7 Hz, 1H), 6.73-6.84 (m, 2H), 3.74 (s, 3H), 2.83-2.99 (m, 4H); ESIMS m/z 169.9 ([M]+—HCl).

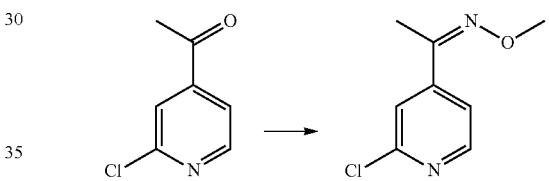

PREPARATION 6

2-Chloro-4-methoximinoacetylpyridine. To a solution of methoxylamine hydrochloride (0.37 g, 4.5 mmol) and sodium acetate (NaOAc; 0.37 g, 4.5 mmol) in $H_2O$ (0.6 mL) and MeOH (5 mL) was added 2-chloro-4-acetylpyridine (0.47 g, 3 mmol), and the reaction was stirred overnight. The MeOH was evaporated, $H_2O$ added, and the solution was extracted with $CH_2Cl_2$. The organic layer was dried ($Na_2SO_4$), filtered, and concentrated in vacuo to provide 0.50 g of crude product. EIMS m/z 184 ([M]+).

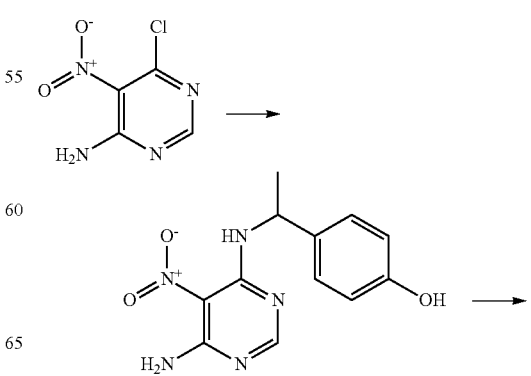

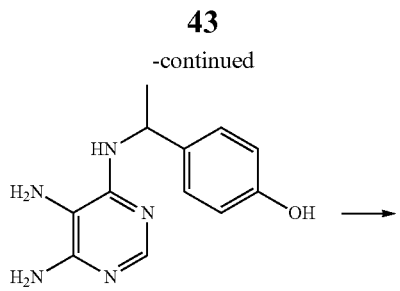

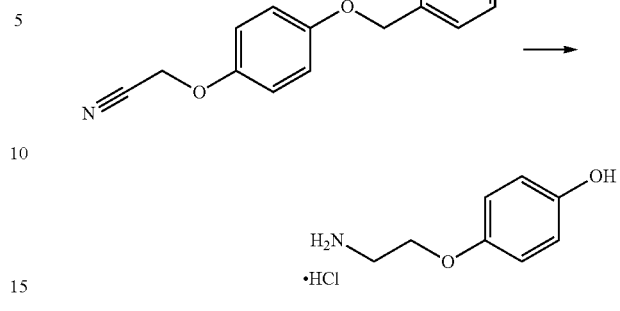

PREPARATION 8

4-(2-aminoethoxy)-phenol.

1. (4-Benzyloxyphenoxy)-acetonitrile. A mixture of 4-benzyloxyphenol (9.4 g, 47 mmol), bromoacetonitrile (6.8 g, 56.7 mmol) in acetone (50 mL) with K$_2$CO$_3$ (2 g, 14. 5 mmol) was heated to reflux 1 min, then at 40° C. for 1 h with stirring. The reaction mixture was filtered, the solids washed with acetone, and the filtrate concentrated in vacuo to afford a tan oil which crystallized on standing, providing 10.70 g of (4-benzyloxyphenoxy)-acetonitrile.

2. 4-(2-Aminoethyloxy)-phenol. In a Parr bottle the product from Preparation 8, Step 1. (10.7 g, 44.7 mmol) was dissolved in absolute EtOH (100 mL). The solution was treated with 37% HCl (9 g) and 10% Pd/C (1.8 g). The reaction mixture was de-aerated, then charged with hydrogen (initial pressure: 50 pso H$_2$) and shaken for 16 h. The mixture was filtered and the filtrate was concentrated in vacuo to afford 4-(2-aminoethoxy)-phenol hydrochloride salt (7.22 g, 85%) as a beige solid. This material was used without further purification.

Also prepared by Preparation 8: 3-(2-Aminoethyloxy)-phenol hydrochloride salt, from 3-benzyloxyphenol.

Also prepared by Preparation 8, Step 2.

2-(4-Methoxy-2,5-dimethylphenyl)-ethylamine hydrochloride, from (4-methoxy-2,5-dimethylphenyl)-acetonitrile.

2-(4-Methoxy-2-methylphenyl)-ethylamine hydrochloride, from (4-methoxy-2-methylphenyl)-acetonitrile.

2-(4-Methoxy-2,3-dimethylphenyl)-ethylamine hydrochloride, from (4-methoxy-2,3-dimethylphenyl)-acetonitrile.

PREPARATION 7

1. 4-[1-(6-Amino-5-nitropyrimidin-4-ylamino)-ethyl]-phenol. 4-Amino-5-nitro-6-chloropyrimidine (5.0 g, 29 mmol), 4-(1-aminoethyl)phenol (4.3 g, 32 mmol) and Et$_3$N (4.5 mL, 3.2 g, 32 mmol) were combined in anhydrous DMF (30 mL). After stirring 2 h at 25° C., the mixture was poured into dilute citric acid (150 mL; pH ca. 3) and the precipitated product was collected by suction filtration and washed with H$_2$O. The solid was recrystallized from a refluxing mixture of H$_2$O (100 mL) and EtOH (50 mL) to yield 6.6 g (84%).

2. 4-[1-(5,6-Diaminopyrimidin-4-ylamino)-ethyl]-phenol. The product from Preparation 7, Step 1, was dissolved in hot EtOH (200 mL), the solution cooled and sparged with nitrogen for 15 minutes (min), treated with Raney nickel (10 g), and hydrogenated for 2 h in a Parr shaker. The catalyst was removed by suction filtration and the solvent removed in vacuo to yield 3.8 g (98%).

EXAMPLE 7

4-[1-(Pteridin-4-ylamino)-ethyl]-phenol. The product from Preparation 7, Step 2 (1.1 g, 4.5 mmol) was dissolved in EtOH (5 mL) and treated with 40 wt. % aqueous glyoxal solution (1.3 g, 9.0 mmol) plus H$_2$O (10 mL) and heated at 75° C. for 40 min. After cooling, the mixture was diluted with H$_2$O (20 mL), and the precipitated product was collected by suction filtration, washed with H$_2$O and dried in vacuo at 80° C. to give 4-[1-(pteridin-4-ylamino)-ethyl]-phenol (900 mg, 75%): $^1$H NMR (300 MHz, CDCl$_3$) δ 9.33 (s, 1H), 9.06 (s, 1H), 8.99 (s, 1H), 8.85 (s, 1H), 8.63 (s, 1H), 7.32 (d, J=9 Hz, 2H), 6.73 (d, J=9 Hz, 2H), 5.52 (t, J=9 Hz, 1H), 1.60 (d, J=9 Hz, 3H).

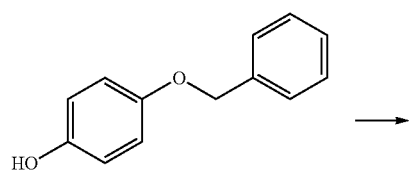

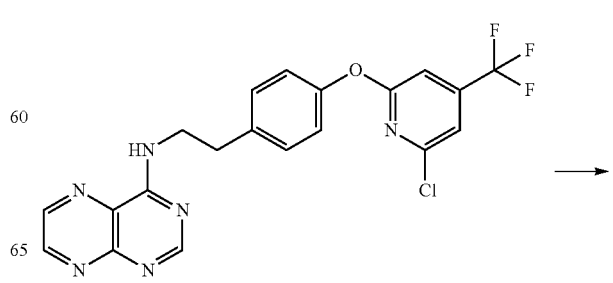

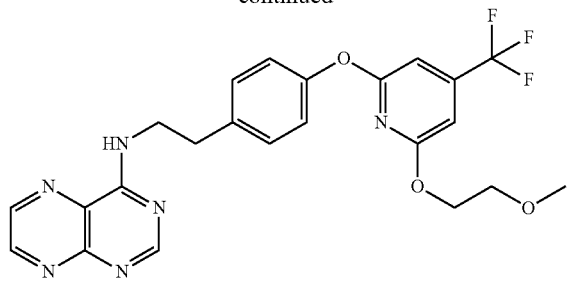

EXAMPLE 8

(2-{4-[6-(2-Methoxyethoxy)-4-trifluoromethyl-pyridin-2-yloxy]-phenyl}-ethyl)-pteridin-4-yl-amine. To a solution of {2-[4-(6-chloro-4-trifluoromethylpyridin-2-yloxy)-phenyl]-ethyl}-pteridin-4-yl-amine (320 mg, 0.7 mmol) in anhydrous methoxyethanol (5 mL) was added NaH (50 mg, 60% dispersion in oil). This was heated at 100° C. until TLC indicated completion. The reaction was evaporated under $N_2$, and the residue was taken up in $H_2O$ (125 mL) and treated with dilute HCl to adjust the pH to 7. The aqueous mixture was washed with EtOAc, the layers were separated, and the organic layer was concentrated in vacuo to provide 0.22 g of a gum. This was dissolved in $Et_2O$, hexane was added, and the $Et_2O$ boiled off to precipitate a solid. The product was collected by suction filtration to afford (2-{4-[6-(2-methoxyethoxy)-4-trifluoromethyl-pyridin-2-yloxy]-phenyl}-ethyl)-pteridin-4-yl-amine (97 mg) as a beige powder: mp 101-104° C.; $^1$H NMR (CDCl$_3$) δ 9.03 (d, J=2.0 Hz, 1H), 8.84 (s, 1H), 8.63 (d, J=1.8 Hz, 1H), 7.31-7.29 (m, 2H), 7.27-7.23 (m, 1H), 7.13-7.09 (m, 2H), 6.73 (s, 1H), 6.55 (s, 1H), 4.30-4.28 (m, 2H), 4.01-3.96 (m, 2H), 3.63-3.61 (m, 2H), 3.38 (s, 3H), 3.10-3.07 (m, 2H); EIMS m/z 487.3([M]$^+$).

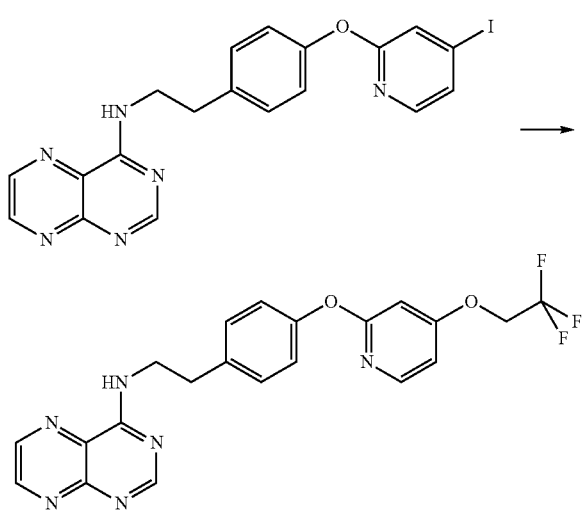

EXAMPLE 9

Pteridin-4-yl-(2-{4-[4-(2,2,2-trifluoroethoxy)-pyridin-2-yloxy]-phenyl}-ethyl)-amine. To a solution of N-(2-{4-[(4-iodopyridin-2-yl)oxy]phenyl}ethyl)pteridin-4-amine (300 mg, 0.64 mmol) and 2,2,2-trifluoroethanol (5 mL, 1.27 mmol) in a 45 mL Parr Bomb was added Cs$_2$CO$_3$ (412 mg, 1.27 mmol), 1,10-phenanthroline (22 mg, 0.127 mmol), and CuI (12 mg, 0.064 mmol). The reaction was held at 110° C. for 72 h, diluted with CH$_2$Cl$_2$, and washed with H$_2$O. The organic layer was concentrated in vacuo and the residue was purified by preparative HPLC to afford pteridin-4-yl-(2-{4-[4-(2,2,2-trifluoroethoxy)-pyridin-2-yloxy]-phenyl}-ethyl)-amine (74 mg, 26%) as a yellow solid: mp 166° C.; EIMS m/z 442 ([M]$^+$).

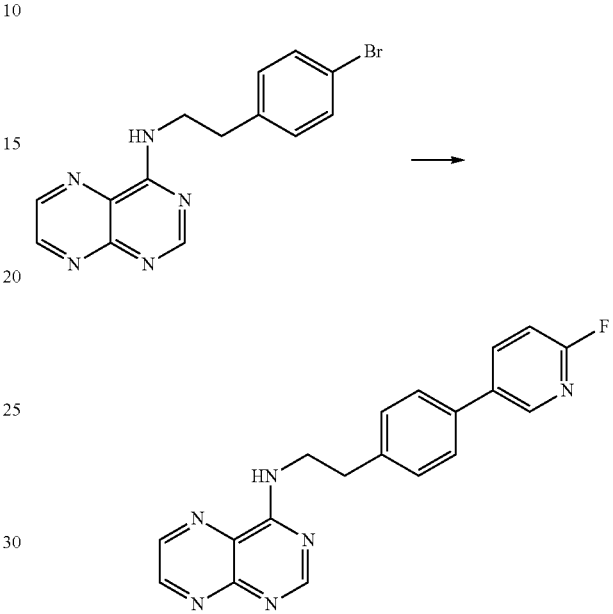

EXAMPLE 10

{2-[4-(6-Fluoropyridin-3-yl)-phenyl]-ethyl}-pteridin-4-yl-amine. To a round bottom flask was added [2-(4-bromophenyl)-ethyl]-pteridin-4-yl-amine (200 mg, 0.61 mmol), 2-fluoro-5-pyridineboronic acid (102 mg, 0.73 mmol), NaHCO$_3$ (102 mg, 1.21 mmol), PdCl$_2$(PPh$_3$)$_2$ (213 mg) and 50% aqueous ethylene glycol dimethyl ether (DME; 3.0 mL). The reaction was heated to reflux for 4.5 h, after which the reaction was cooled and the resulting orange precipitate filtered. The filtered material was washed with EtOAc and the filtrate washed with H$_2$O. The organic fractions were pooled and concentrated in vacuo. The residue (229 mg) was purified by preparative RP-HPLC to afford {2-[4-(6-fluoropyridin-3-yl)-phenyl]-ethyl}-pteridin-4-yl-amine (20 mg) as an orange solid: mp 184-186° C.; EIMS m/z 346 ([M]$^+$).

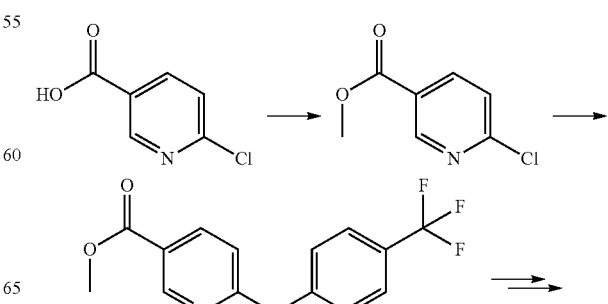

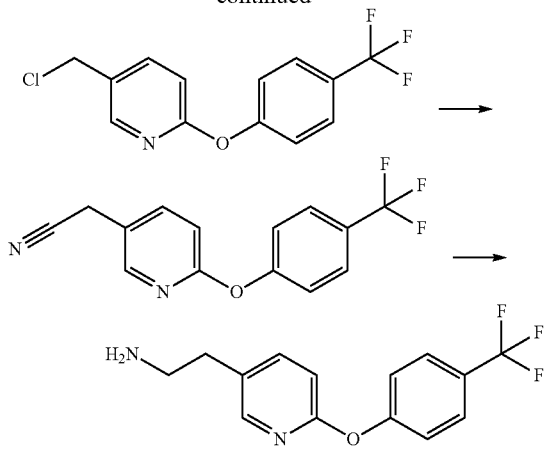

PREPARATION 9

2-[6-(4-Trifluoromethylphenoxy)-pyridin-3-yl]-ethylamine.

1. 6-Chloronicotinic acid, methyl ester. To a solution of 6-chloronicotinic acid (20.0 g, 0.127 mol) in CH$_2$Cl$_2$ (250 mL) was added oxalyl chloride (123.3 mL, 0.15 mol) with 1-5 drops of DMF. The solution was stirred 18 h and concentrated in vacuo. The residue was dissolved in CH$_2$Cl$_2$ (100 mL) and cooled in an ice bath. To this was added MeOH (20 mL) and the solution was stirred for 15 min while maintaining a temp below 40° C. The solvent was removed in vacuo, and the residue was dissolved in Et$_2$O, washed with H$_2$O and brine, dried with Na$_2$SO$_4$, and filtered through SiO$_2$. The solvent was removed in vacuo to yield 6-chloronicotinic acid, methyl ester (21 g) as an off-white solid: $^1$H-NMR (300 MHz, CDCl$_3$) δ 9.02 (d, J=13.8 Hz, 1H), 8.51-8.06 (m, 1H), 7.76-7.30 (m, 1H), 4.01 (s, 3H); EIMS m/z 171 ([M]$^+$), which was used in Step 2 without further purification.

2. 6-(4-Trifluoromethylphenoxy)-nicotinic acid methyl ester. To a suspension of NaH (60% dispersion in oil; 1.2 g, 30 mmol) in 30 mL of DMSO was added a solution of 4-(trifluoromethyl)phenol (1.86 g, 30 mmol) in 20 mL of DMSO and the mixture was stirred for 30 min. To this was added methyl 6-chloronicotinate (5.13 g, 30 mmol) and the solution was heated overnight at 70° C. The reaction was cooled to room temperature and then diluted with Et$_2$O. The solution was washed with H$_2$O, brine, dried with Na$_2$SO$_4$, suction filtered, and the solvent removed in vacuo. The residue was purified via normal phase column chromatography over SiO$_2$ using 15% Et$_2$O/pentane to yield 6-(4-trifluoromethylphenoxy)-nicotinic acid methyl ester (4.5 g) as a colorless solid: $^1$H-NMR (300 MHz, CDCl$_3$) δ 8.81 (dd, J=2.5, 0.6 Hz, 1H), 8.33 (dd, J=8.6, 2.4 Hz, 1H), 7.69 (d, J=8.5 Hz, 2H), 7.31-7.24 (m, 2H), 7.02 (dd, J=8.5, 0.6 Hz, 1H), 3.93 (s, 3H); EIMS m/z 297 ([M]$^+$).

3. 5-Chloromethyl-2-(4-trifluoromethylphenoxy)-pyridine. To a suspension of LiAlH$_4$ (0.051 g, 13.5 mmol) in THF (20 mL) was added dropwise a solution of 6-(4-trifluoromethylphenoxy)-nicotinic acid methyl ester (4.0 g, 13.5 mmol) in THF (10 mL). After the mixture was stirred 1 h, the reaction was quenched by the addition of 4M NaOH (3 mL) followed by H$_2$O (3 mL). A precipitate formed and the THF was decanted. The precipitate was washed with hot THF 2 times. The organic fractions were combined and the solvent removed in vacuo to yield 3.5 g of yellow oil which was dissolved in toluene (15 mL) and cooled in an ice bath. To this solution was added SOCl$_2$ (3.9 mL) dropwise. The solution was allowed to warm to RT and stirred 2 h, at which point the reaction was concentrated in vacuo. The residue was dissolved in Et$_2$O and washed with 1M NaOH. The Et$_2$O phase was dried with Na$_2$SO$_4$ and suction filtered through SiO$_2$. The solvent was removed in vacuo yielding 5-chloromethyl-2-(4-trifluoromethylphenoxy)-pyridine (1.8 g) as a yellow solid: $^1$H NMR (300 MHz, CDCl$_3$) δ 8.17 (d, J=2.5 Hz, 1H), 7.80 (dd, J=8.5, 2.5 Hz, 1H), 7.66 (dd, J=5.5, 3.5 Hz, 2H), 7.30-7.17 (m, 2H), 7.00 (d, J=8.4 Hz, 1H), 4.57 (s, 2H); EIMS m/z 287 ([M]$^+$).

4. [6-(4-Trifluoromethylphenoxy)-pyridin-3-yl]-acetonitrile To a solution of 5-chloromethyl-2-(4-trifluoromethylphenoxy)-pyridine (1.8 g, 6.27 mmol) in EtOH (12 mL) was added NaCN (1.23 g, 25 mmol). The reaction mixture was heated to 50° C. for 16 h. More ethanol (6 mL) was added, and the reaction mixture clarified. After an additional 3 h, the solvent was removed in vacuo, the residue taken up in Et$_2$O and washed with H$_2$O. The organic layer was dried with Na$_2$SO$_4$, suction filtered and concentrated in vacuo. The residue was purified by flash chromatography (50% Et$_2$O in petroleum ether over SiO$_2$) to yield [6-(4-trifluoromethylphenoxy)-pyridin-3-yl]-acetonitrile (1.3 g) as a pink solid; $^1$H NMR (300 MHz, CDCl$_3$) δ 8.17-8.09 (m, 1H), 7.81-7.71 (m, 1H), 7.70-7.61 (m, 2H), 7.29-7.19 (m, 2H), 7.04 (d, J=8.4 Hz, 1H), 3.73 (s, 2H); EIMS m/z 278 ([M]$^+$).

5. 2-{6-[4-(Trifluoromethyl)phenoxy]pyridin-3-yl}ethylamine. To a solution of AlCl$_3$ (268 mg, 1.8 mmol) in Et$_2$O cooled to 0° C. in an ice bath was added LiAlH$_4$ (66 mg, 1.8 mmol) in one portion, under N$_2$. After stirring 15 min, a solution of [6-(4-trifluoromethylphenoxy)-pyridin-3-yl]-acetonitrile (500 mg, 1.8 mmol) in Et$_2$O (2 mL) and THF (1 mL) was added dropwise resulting in an exotherm. The reaction was allowed to cool to room temperature, and after 2 h, the reaction was quenched by careful addition of 5 mL of saturated aqueous ammonium chloride. The resulting mixture was made alkaline by addition of 2M NaOH solution. The precipitate which formed was removed by filtration through Celite. The filtrate phases were separated, and the aqueous phase was extracted 3 times with Et$_2$O. The pooled organic fractions were dried with Na$_2$SO$_4$ and suction filtered. The solvent was removed in vacuo to yield 2-[6-(4-trifluoromethylphenoxy)-pyridin-3-yl]-ethylamine (200 mg), as a brown oil.

Also prepared by Preparation 9, Steps 4 and 5. 2-(4-Methoxy-3-trifluoromethylphenyl)-ethylamine hydrochloride, from (4-methoxy-3-trifluoromethylphenyl)-methanol.

Also prepared by Preparation 9, Step 5.

2-(3-Fluoro-4-methoxyphenyl)-ethylamine hydrochloride, from (3-fluoro-4-methoxyphenyl)-acetonitrile.

2-(4-Methoxy-3-methylphenyl)-ethylamine hydrochloride, from (4-methoxy-3-methylphenyl)-acetonitrile.

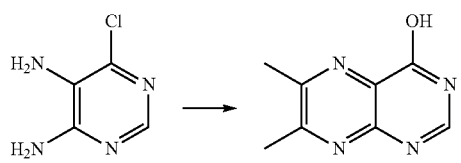

PREPARATION 10

6,7-Dimethyl-pteridin-4-ol. A mixture of 6-chloropyrimidine-4,5-diamine (1.4 g, 10 mmol) and 2,3-butanedione (2.0 g, 23 mmol) in toluene (35 mL) and methanol (10 mL) was stirred at reflux for 1 h. Upon cooling, the product precipitated and was collected by suction filtration and rinsed with a MeOH/Et₂O mixture (ca. 1:2), then air dried to afford 6,7-dimethylpteridin-4-ol (1.4 g, 72%) as a gold powder.

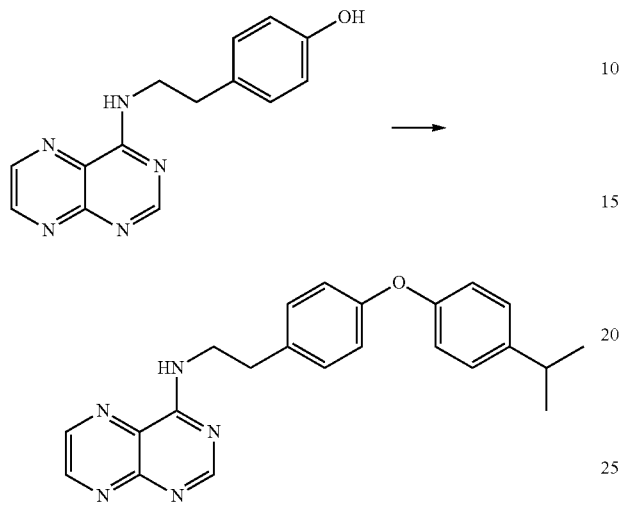

EXAMPLE 11

{2-[4-(4-Isopropylphenoxy)-phenyl]-ethyl}-pteridin-4-yl-amine. 4-[2-(Pteridin-4-ylamino)-ethyl]-phenol (500 mg, 1.9 mmol), 4-isopropylphenylboronic acid (400 mg, 2.4 mmol), anh. Cu(OAc)₂ (360 mg, 2.0 mmol) and powdered, freshly activated 4 Å molecular sieves (approximately 1 g) were combined in CH₂Cl₂ (15 mL), treated with pyridine (920 μL, 900 mg, 11.4 mmol) and sealed and stirred for 20 h with a moisture trap. The reaction was suction filtered and the filtrate shaken with dilute aqueous NH₄OH. The organic phase was washed with H₂O and brine and concentrated in vacuo. The residue was purified by preparative RP-HPLC using 80% MeCN/H₂O to yield {2-[4-(4-isopropylphenoxy)-phenyl]-ethyl}-pteridin-4-yl-amine (78 mg, 11%) as a tan solid: mp 105-106.5° C.

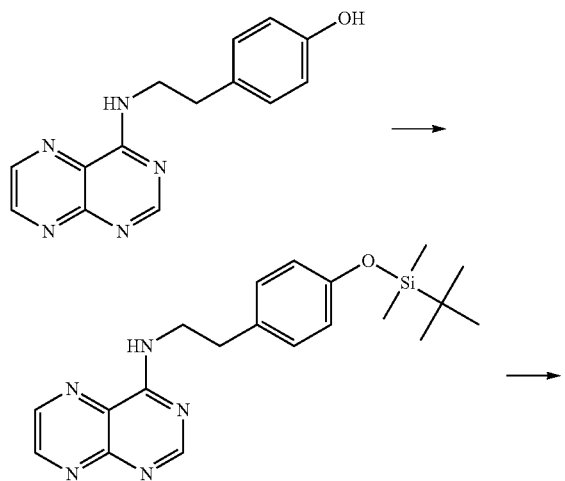

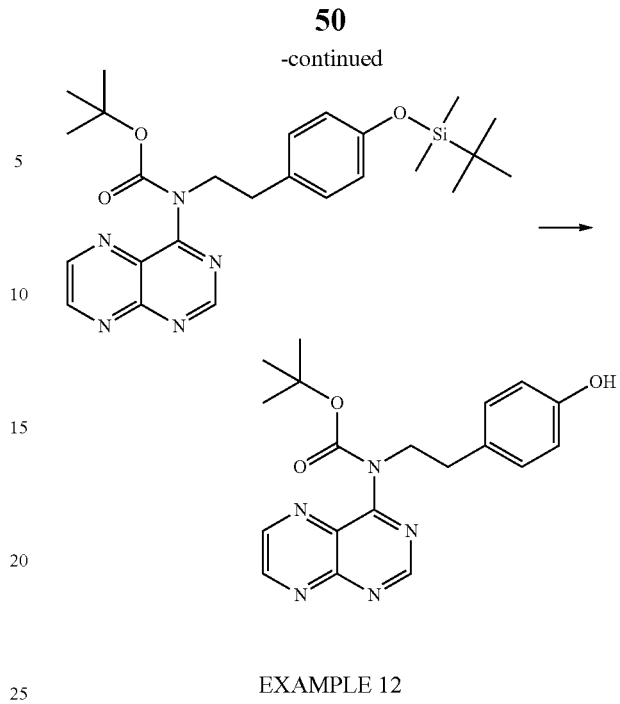

EXAMPLE 12

{2-[4-(tert-Butyldimethylsilanyloxy)-phenyl]-ethyl}-pteridin-4-yl-amine. 4-[2-(Pteridin-4-ylamino)-ethyl]-phenol (1.0 g, 3.7 mmol) was partially dissolved in dry DMF (75 mL), treated with imidazole (630 mg, 9.3 mmol), cooled to 0-5° C. and treated dropwise with a solution of t-butyldimethylsilyl chloride (680 mg, 4.5 mmol) in DMF (15 mL). After warming to 25° C. the mixture was stirred for 20 h, diluted with H₂O (75 mL) and extracted with EtOAc. The extracts were washed with H₂O, brine, dried (Na₂SO₄), filtered and concentrated in vacuo to give {2-[4-(tert-butyldimethylsilanyloxy)-phenyl]-ethyl}-pteridin-4-yl-amine (1.3 g) as a white solid: mp 164-165° C.; $^1$H NMR (300 MHz, CDCl₃) δ 8.99 (s, 1H), 8.61 (s, 1H), 8.59 (s, 1H), 8.26 (d, J=5.9 Hz, 1H), 6.8-7.2 (m, 5H), 3.98 (t, J=6.2 Hz, 2H), 2.99 (t, 6.3 Hz, 2H), 1.02 (s, 6H), 0.18 (s, 9H).

EXAMPLE 13

{2-[4-(tert-Butyldimethylsilanyloxy)-phenyl]-ethyl}-pteridin-4-yl-carbamic acid tert-butyl ester. {2-[4-(tert-Butyldimethylsilanyloxy)-phenyl]-ethyl}-pteridin-4-yl-amine (10.15 g, 3.0 mmol) was dissolved in dry DMF (50 mL), treated with di-tert-butyldicarbonate (730 mg, 3.3 mmol) plus approximately DMAP (N,N-dimethyl-4-aminopyridine; 25 mg) and stirred at 25° C. for 22 h. The mixture was diluted with H₂O and extracted with EtOAc. The EtOAc extracts were washed with H₂O, dried (Na₂SO₄), suction filtered and concentrated in vacuo to give {2-[4-(tert-butyldimethylsilanyloxy)-phenyl]-ethyl}-pteridin-4-yl-carbamic acid tert-butyl ester (1.2 g; 83%), as a yellow gum; ESIMS m/z 482 ([M+H]⁺).

EXAMPLE 14

[2-(4-Hydroxyphenyl)-ethyl]-pteridin-4-yl-carbamic acid tert-butyl Ester.

{2-[4-(tert-Butyldimethylsilanyloxy)-phenyl]-ethyl}-pteridin-4-yl-carbamic acid tert-butyl ester (680 mg, 1.4 mmol) was dissolved in 5 mL CH₂Cl₂ and treated with tetrabutylammonium fluoride 3H₂O in 10 mL THF. After stirring for 18 h, the solution was washed with H₂O, dried (Na₂SO₄), suction filtered, and concentrated in vacuo to give [2-(4-hydroxyphenyl)-ethyl]-pteridin-4-yl-carbamic acid tert-butyl ester as a tan solid, mp 132-134° C. (dec.); ESIMS m/z ([M+H]⁺) 368.

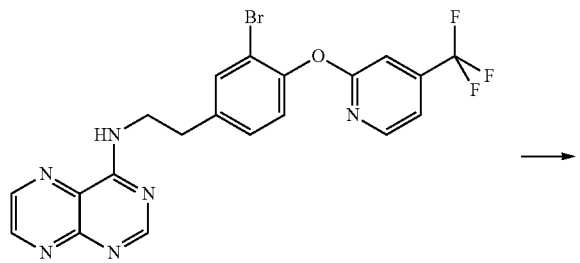

EXAMPLE 15

5-[2-(Pteridin-4-ylamino)-ethyl]-2-(4-trifluoromethyl-pyridin-2-yloxy)-benzoic acid, methyl ester. To a solution of {2-[3-bromo-4-(4-trifluoromethylpyridin-2-yloxy)-phenyl]-ethyl}-pteridin-4-yl-amine (243 mg, 0.5 mmol), in methanol in a 45 mL Parr bomb was added Pd(OAc)$_2$ (5.6 mg, 0.25 mmol), DPPB (21 mg, 0.5 mmol), and K$_2$CO$_3$ (138 mg, 1 mmol). The reactor was sealed and charged with 300 psi of CO. The reaction was heated to 110° C. for 15 h, cooled to ambient temperature, filtered through Celite, and concentrated in vacuo. The residue was dissolved in CH$_2$Cl$_2$, washed with H$_2$O, brine, dried over Na$_2$SO$_4$, suction filtered and concentrated in vacuo. The residue was slurried in Et$_2$O and pentane. The solvent was decanted to leave 5-[2-(pteridin-4-ylamino)-ethyl]-2-(4-trifluoromethylpyridin-2-yloxy)-benzoic acid, methyl ester (55 mg; 23% yield) as a light yellow solid: mp 171-172° C.; $^1$H NMR (300 MHz, CDCl$_3$) δ 9.04 (d, J=2.0 Hz, 1H), 8.84 (s, 1H), 8.64 (d, J=1.9 Hz, 1H), 8.23 (d, J=5.0 Hz, 1H), 7.94 (d, J=2.3 Hz, 1H), 7.52 (dd, J=8.2, 2.2 Hz, 1H), 7.26-7.12 (m, 4H), 4.02 (dd, J=13.7, 6.9 Hz, 2H), 3.67 (s, 3H), 3.13 (t, J=7.3 Hz, 2H); ESIMS m/z 471.

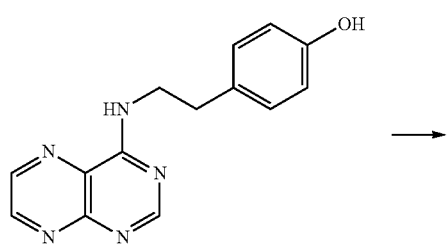

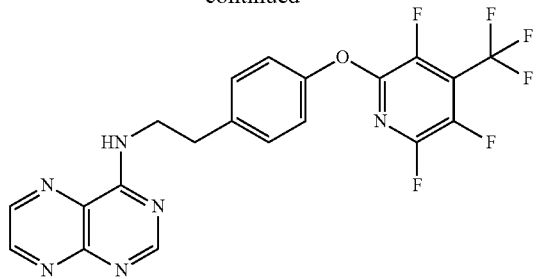

EXAMPLE 16

Pteridin-4-yl-{2-[4-(3,5,6-trifluoro-4-trifluoromethyl-pyridin-2-yloxy)-phenyl]-ethyl}-amine. 4-[2-(Pteridin-4-ylamino)-ethyl]-phenol (0.27 g, 1.0 mmol), 2,3,5,6-tetrafluoro-4-trifluoromethylpyridine (0.24 g, 1.0 mmol) and DMF (5 mL) were added to a 25 mL round bottom flask equipped with magnetic stirring bar and dry nitrogen line. To the reaction mixture was added Et$_3$N (0.12 g, 1.2 mmol). After stirring 24 h at room temperature, the reaction mixture was concentrated in vacuo, and the residue was partitioned between H$_2$O and EtOAc. The organic layer was concentrated in vacuo and the residue was purified by column chromatography (EtOAc/hexane over SiO$_2$) to afford pteridin-4-yl-{2-[4-(3,5,6-trifluoro-4-trifluoromethyl-pyridin-2-yloxy)-phenyl]-ethyl}-amine (110 mg) as a beige solid: mp 103-108° C.

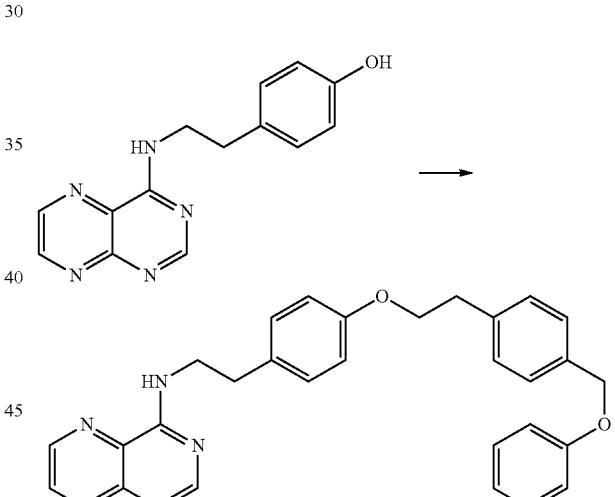

EXAMPLE 17

(2-{4-[2-(4-Benzyloxy-phenyl)-ethoxy]-phenyl}-ethyl)-pteridin-4-yl-amine. 4-[2-(Pteridin-4-ylamino)-ethyl]-phenol (300 mg, 10.1 mmol), triphenylphosphine (790 mg, 3.0 mmol) and 2-(4-benzyloxyphenyl)ethanol (700 mg, 3.0 mmol) were combined in 10 mL anh. dioxane, treated with diisopropylazodicarboxylate (590 μL, 610 mg, 3.0 mmol) and stirred for 18 h. The volatiles were removed in vacuo and the residue was chromatographed on SiO$_2$ with EtOAc (10% to 40%) in CH$_2$Cl$_2$ to obtain (2-{4-[2-(4-benzyloxyphenyl)-ethoxy]-phenyl}-ethyl)-pteridin-4-ylamine (105 mg; 20%) as a white solid: mp 120-122° C.; ESIMS m/z 478 ([M+H]⁺); $^1$H NMR (300 MHz, CDCl$_3$) δ 9.23 (s, 1H), 8.96 (s, 1H), 8.80 (s, 1H), 6.8-7.5 (m, 13H), 4.1 (m, 2H), 3.90 (m, 2H), 3.01 (m, 4H).

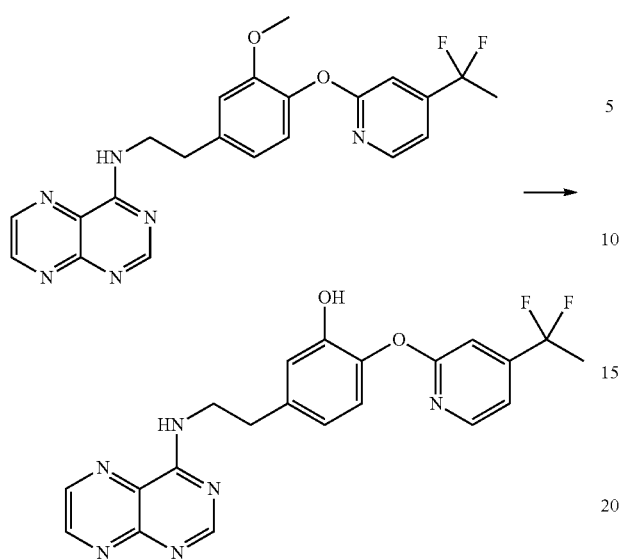

EXAMPLE 18

2-[4-(1,1-Difluoroethyl)-pyridin-2-yloxy]-5-[2-(pteridin-4-ylamino)-ethyl]-phenol. To a solution of (2-{4-[4-(1,1-difluoroethyl)-pyridin-2-yloxy]-3-methoxyphenyl}-ethyl)-pteridin-4-yl-amine (1.37 g, 3.13 mmol) in CH$_2$Cl$_2$ (15 mL) cooled to 0° C., was added 1M BBr$_3$/hexane (9.4 mL, 9.4 mmol). The solution was allowed to warm to room temperature and stirred overnight. The reaction was quenched with methanol and concentrated in vacuo. The residue was dissolved in small amount of methanol and poured into aqueous NaHCO$_3$. The hydroxyaryl product precipitated and was collected by suction filtration and washed with H$_2$O. The filter cake was air dried on the filter to yield 2-[4-(1,1-difluoroethyl)-pyridin-2-yloxy]-5-[2-(pteridin-4-ylamino)-ethyl]-phenol (0.76 g), as a light brown solid: $^1$H NMR (300 MHz, d$_6$-DMSO) δ 9.53 (br s, 1H), 9.45 (s, 1H), 9.12 (s, 1H), 8.91 (d, J=1.5 Hz, 1H), 8.78 (br, 1H), 8.20 (d, J=5.3 Hz, 1H), 7.22 (d, J=5.3 Hz, 1H), 7.08 (s, 1H), 6.98 (d, J=8.1 Hz, 1H), 6.85 (d, J=1.8 Hz, 1H), 6.72 (dd, J=8.1, 1.8 Hz, 1H), 3.84 (dd, J=14.7, 7.4 Hz, 2H), 2.93 (t, J=7.4 Hz, 2H), 1.98 (t, J=19.2 Hz, 3H); ESIMS m/z 425 ([M+H]$^+$).

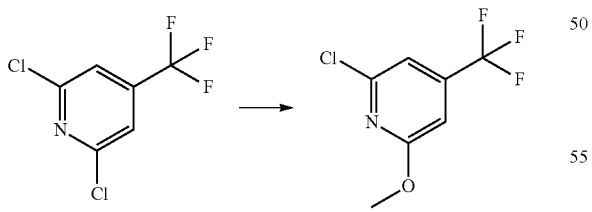

PREPARATION 11

2-Methoxy-6-chloro-4-trifluoromethylpyridine. To a solution of 2,6-dichloro-4-trifluoromethylpyridine (10 g, 46.3 mmol) in methanol (200 mL) was added 25% NaOH/MeOH (12.5 g, 13.2 mL, 231 mmol), which was then stirred at 50° C. for 2 h and then at room temperature overnight. The reaction mixture was extracted with pentane, and the extract was concentrated in vacuo to afford 2-methoxy-6-chloro-4-trifluoromethylpyridine (9.79 g), used without further purification.

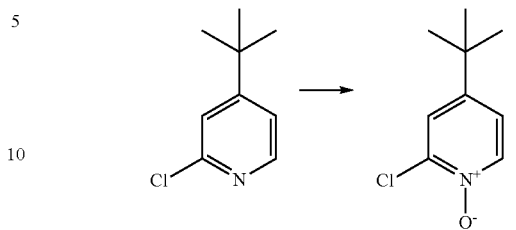

PREPARATION 12

2-Chloro-4-t-butylpyridine-N-oxide. 2-Chloro-4-t-butylpyridine (5.0 g, 30 mmol) was dissolved in chloroform (75 mL), treated with MCPBA, ca. 75% (8.3 g, 36 mmol, 1.2 equivalents) and heated to reflux for 19 h. The mixture was stirred with sodium bisulfite solution until testing with starch-iodide paper indicated consumption of oxidant. The pH was adjusted to 7 with saturated aqueous NaHCO$_3$ solution, the phases separated and the aqueous phase extracted once with CH$_2$Cl$_2$. The organic phases were pooled and washed twice with H$_2$O, once with brine, dried (Na$_2$SO$_4$) and concentrated in vacuo to afford 2-chloro-4-t-butylpyridine-N-oxide (5.0 g, 90%), which crystallized to long white needles on standing.

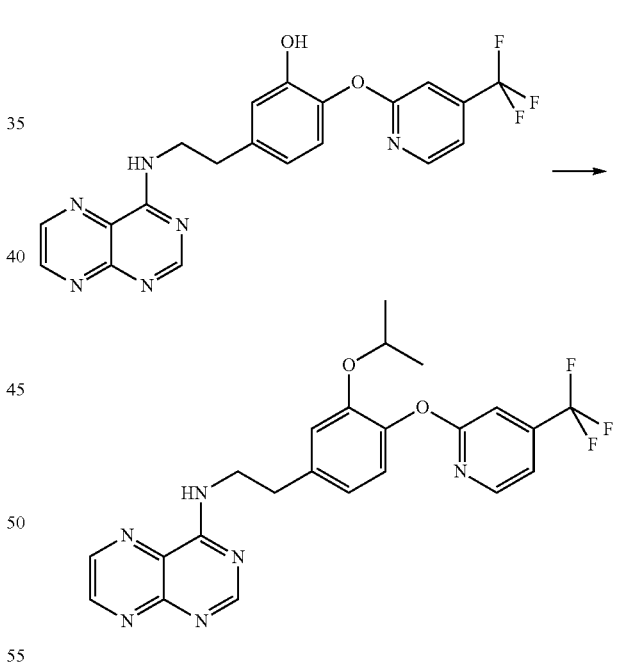

EXAMPLE 19

{2-[3-(Isopropoxy)-4-(4-trifluoromethyl-pyridin-2-yloxy)-phenyl]-ethyl}-pteridin-4-ylamine. To a solution of 5-[2-(pteridin-4-ylamino)-ethyl]-2-(4-trifluoromethylpyridin-2-yloxy)-phenol (200 mg, 0.47 mmol) in 2 mL of DMSO was added 2-iodopropane (62 mg, 0.5 mmol), and K$_2$CO$_3$ (97 mg, 0.7 mmol). The solution was heated 2 h at 50° C., after which TLC analysis indicated absence of starting material. The mixture was poured onto ice. The product precipitated and was collected by suction filtration, washed with H$_2$O, and air dried, yielding {2-[3-(isopropoxy)-4-(4-trifluoromethylpyridin-2-yloxy)-phenyl]-ethyl}-pteridin-4-ylamine (180 mg; 81% yield) as a light brown solid: ESIMS m/z: 471 ([M+H]+).

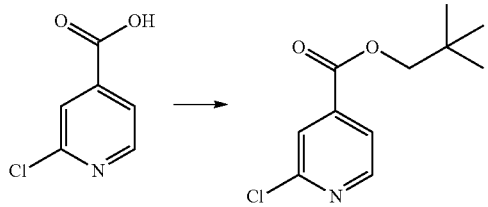

PREPARATION 13

2-Chloroisonicotinic acid, 2,2-dimethyl-propyl ester. 2-Chloroisonicotinic acid (2.0 g, 13 mmol) was suspended in 50 mL dry CH$_2$Cl$_2$ and treated with oxalyl chloride (3.5 mL, 5.0 g, 39 mmol) plus 3 drops DMF. The mixture was stirred for 4 h, the volatiles removed in vacuo and the residue taken up in 50 mL CH$_2$Cl$_2$. After cooling to 0° C. and treating with neopentyl alcohol (1.7 ml, 1.4 g, 16 mmol), Et$_3$N (2.5 mL, 1.8 g, 18 mmol) was added in portions. The mixture was warmed to 25° C., stirred for 15 h, washed sequentially with 15 mL H$_2$O, 15 mL saturated aqueous NaHCO$_3$, and 15 mL brine, then dried (Na$_2$SO$_4$), filtered, and concentrated in vacuo to give 2.4 g (80%) of 2-chloroisonicotinic acid, 2,2-dimethyl-propyl ester as an oil, used without additional purification: $^1$H NMR (300 MHz, CDCl$_3$) δ 8.56 (d, J=5.6 Hz, 1H), 7.88 (s, 1H), 7.78 (d J=5.0 Hz, 1H), 4.06 (s, 2H), 1.05 (s, 9H).

Also prepared by Preparation 13. 2-Chloroisonicotinic acid, tert-butyl ester, from tert-butanol.

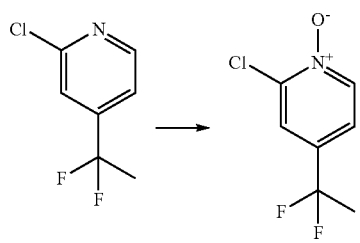

PREPARATION 14

2-chloro-4-(1,1-difluoro)ethylpyridine-N-oxide. To a solution of 1.27 g (7 mmol) 2-chloro-4-(1,1-difluoro)ethylpyridine (Preparation 4) in TFA was added 30% hydrogen peroxide (6 mL) and the solution was heated at reflux for 2.5 h. The TFA was removed in vacuo and the residue poured into ice-cold H$_2$O. The mixture was neutralized with Na$_2$CO$_3$ and extracted with EtOAc and CH$_2$Cl$_2$. The pooled organic layers were dried (Na$_2$SO$_4$), filtered and concentrated in vacuo to give 2-chloro-4-(1,1-difluoroethyl)-pyridine 1-oxide (1.00 g) as a brown oil: $^1$H NMR (CDCl$_3$): δ 8.39 (d, J=6.6 Hz, 1H), 7.63 (d, J=2.4 Hz, 1H), 7.33 (dd, J=6.6, 2.4 Hz, 1H), 1.94 (t, J=18 Hz, 3H); EIMS m/z 193 ([M]+).

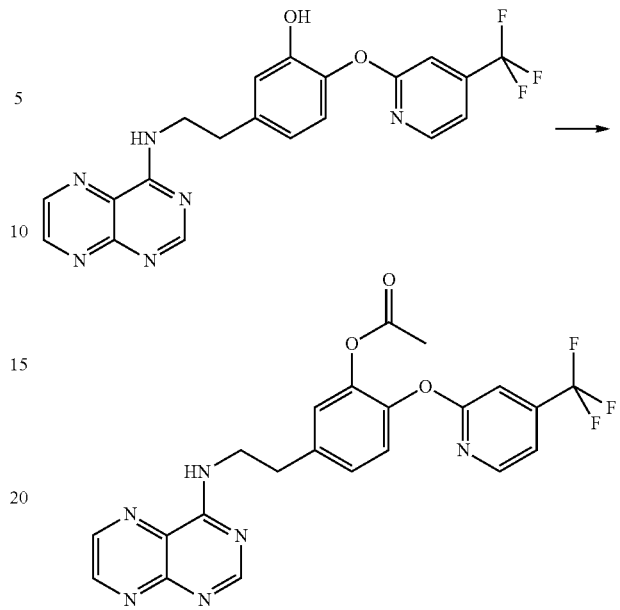

EXAMPLE 20

Acetic acid 5-[2-(pteridin-4-ylamino)-ethyl]-2-(4-trifluoromethylpyridin-2-yloxy)-phenyl ester. To 4 mL of acetic anhydride was added 5-[2-(Pteridin-4-ylamino)-ethyl]-2-(4-trifluoromethylpyridin-2-yloxy)-phenol (330 mg, 0.7 mmol), pyridine (0.5 mL), and 5 mg DMAP. The solution was stirred at ambient temperature for 15 h, then diluted with CH$_2$Cl$_2$ and washed sequentially with H$_2$O and saturated aqueous NaHCO$_3$ solution. The organic fraction was dried with Na$_2$SO$_4$, suction filtered, and concentrated in vacuo. The residue was diluted with 1:1 Et$_2$O/pentane. The product precipitated, was collected by filtration, and the cake washed with cool 1:1 Et$_2$O/pentane. This afforded 184 mg (56% yield) of acetic acid 5-[2-(pteridin-4-ylamino)-ethyl]-2-(4-trifluoromethylpyridin-2-yloxy)-phenyl ester, an off-white solid: ESIMS m/z: 471 ([M]+).

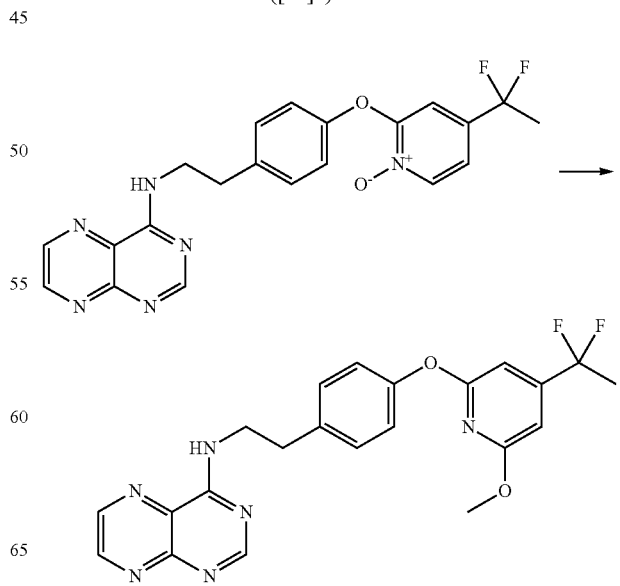

EXAMPLE 21

(2-{4-[4-(1,1-Difluoroethyl)-6-methoxypyridin-2-yloxy]-phenyl}-ethyl)-pteridin-4-yl-amine. A round bottom flask was charged with (2-{4-[4-(1,1-difluoroethyl)-1-oxy-pyridin-2-yloxy]-phenyl}-ethyl)-pteridin-4-yl-amine (0.52 g, 1.13 mmol), ethyl chloroformate (0.43 mL, 4.5 mmol), Et$_3$N (0.95 mL, 6.81 mmol) and MeOH (10 mL), and heated at reflux for 2 days. The solvent was removed and the residue dissolved in CH$_2$Cl$_2$. The solution was washed with brine, dried over Na$_2$SO$_4$, filtered, concentrated in vacuo and purified by preparative RP-HPLC to give (2-{4-[4-(1,1-difluoroethyl)-6-methoxypyridin-2-yloxy]-phenyl}-ethyl)-pteridin-4-yl-amine (0.130 g, 24% yield) as a pale yellow solid: $^1$H NMR (300 MHz, CDCl$_3$) δ 9.02 (d, J=1.9 Hz, 1H), 883 (s, 1H), 8.62 (d, J=1.9 Hz, 1H), 7.29 (d, J=8.1 Hz, 2H), 7.12 (d, J=8.1 Hz, 2H), 6.54 (s, 1H), 6.44 (s, 1H), 3.98 (dd, J=13.2, 6.9 Hz, 2H), 3.79 (s, 3H), 3.08 (t, J=6.9 Hz, 2H), 1.86 (t, J=18.3 Hz, 3H); ESIMS m/z 439.2 ([M+H]$^+$).

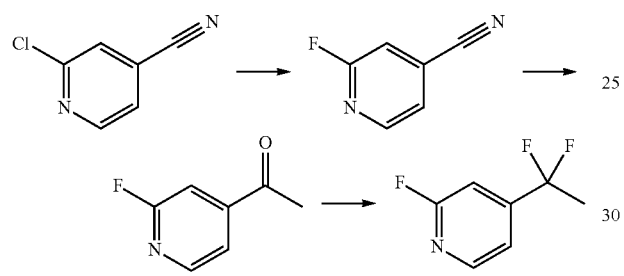

PREPARATION 15

4-(1,1-Difluoroethyl)-2-fluoropyridine.

1. 2-Fluoroisonicotinonitrile. Cesium fluoride (30 g, 0.22 mmol) was slurried in dry sulfolane (150 mL) and concentrated via vacuum distillation at 0.5 mm Hg. After removal of 20% of the solvent, the suspension was cooled and 2-chloroisonicotinonitrile (15 g, 0.11 mmol) was added, then stirred and heated at 100° C. for 20 h. It was cooled to 25° C., poured into H$_2$O (200 mL) and extracted with Et$_2$O. The Et$_2$O phase was washed with H$_2$O, then brine, dried over Na$_2$SO$_4$, filtered and concentrated in vacuo. The residue was purified by column chromatography over SiO$_2$ with CH$_2$Cl$_2$ to give 2-fluoroisonicotinonitrile (12.0 g) as a low-melting colorless solid: EIMS m/z: 122 ([M]$^+$); $^1$H NMR (CDCl$_3$): δ 8.45 (dd, 1H), 7.47 (dd, 1H), 7.24 (m, 1H).

2. 1-(2-Fluoropyridin-4-yl)-ethanone. To a solution of 2-fluoroisonicotinonitrile (10 g, 82 mmol) in anhydrous Et$_2$O (250 mL) cooled in an ice-H$_2$O bath was slowly added 3M methyl magnesium bromide in hexane (40 mL, 120 mmol). The mixture was stirred at 25° C. overnight. The reaction was quenched slowly with 1N aq. citric acid solution at 0° C. until all solids dissolved. Brine was added and the two phases were separated. The organic phase was dried over Na$_2$SO$_4$, filtered, and concentrated in vacuo to give 1-(2-fluoropyridin-4-yl)-ethanone (6.2 g) as a brown oil. The aqueous phase was stirred at 25° C. for 3 h, then extracted with CH$_2$Cl$_2$. The CH$_2$Cl$_2$ layer was dried over Na$_2$SO$_4$, filtered, and concentrated in vacuo to give an additional 1.1 g of the product, for a total of 7.3 g, used in the next step without further purification: EIMS m/z 139 ([M]$^+$). $^1$H NMR (CDCl$_3$): δ 8.25 (dd, 1H), 7.47 (d, 1H), 7.21 (m, 1H).

3. 2-Fluoro-4-(1,1-difluoroethyl)pyridine. 1-(2-Fluoropyridin-4-yl)-ethanone (6.2 g, 44.6 mmol) from the previous reaction was treated with diethylamino-sulfurtrifluoride (17 mL, 130 mmol), as in Preparation 4, to yield 3.5 g of 2-fluoro-4-(1,1-difluoroethyl)pyridine (45% yield), as a light yellow oil: EIMS m/z 161 ([M]$^+$).

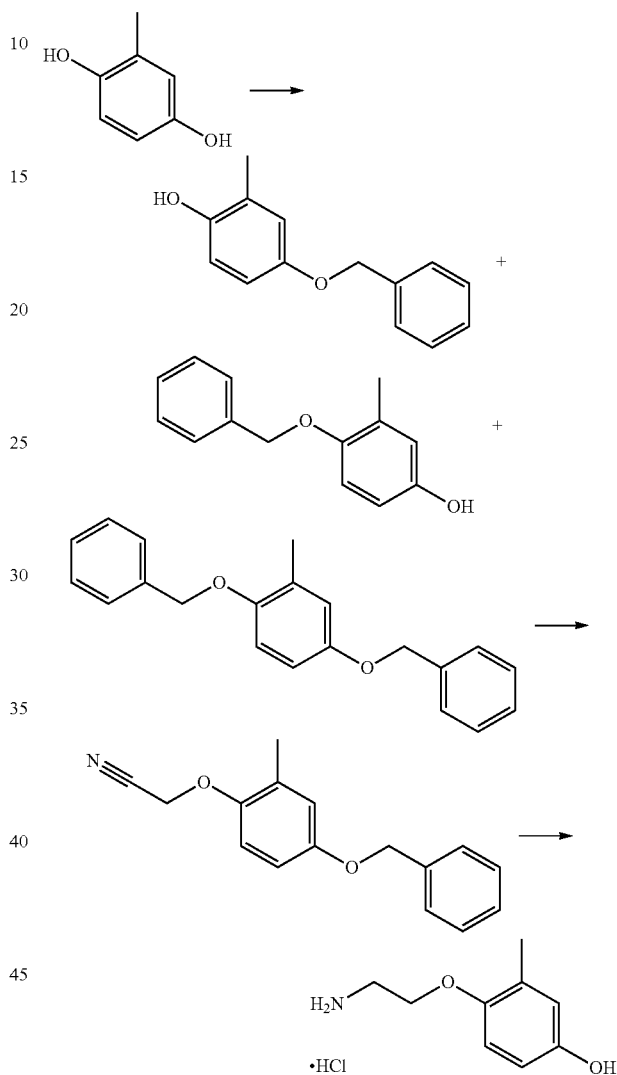

PREPARATION 16

4-(2-Aminoethoxy)-3-methylphenol hydrochloride.

1. 4-Benzyloxy-2-methylphenol. 2-Methylbenzene-1,4-diol (12.4 g, 0.1 mol) was dissolved in acetone (200 mL) in a 500 mL round bottom flask equipped with magnetic stirrer, reflux condenser and dry nitrogen line. To the solution was added K$_2$CO$_3$ (20.5 g), followed by benzyl bromide (12.2 mL, 0.1 mol) with vigorous stirring. After stirring at room temperature for 72 h, the reaction mixture was filtered and concentrated in vacuo. The residue was partitioned between slightly acidic H$_2$O (pH adjusted to 5 with 0.1N HCl) and a 1:1 mixture of Et$_2$O and pentane. The organic layer was filtered and concentrated in vacuo to provide a black oil (20.66 g). The oil was extracted with isopentane (3×150 mL) and the pooled isopentane fractions were concentrated in vacuo to provide an orange oil (10 g); the dark insoluble residue was set aside. The orange oil was passed over a SiO₂ column with Et₂O/pentane (1:1) eluent. The appropriate fractions were pooled and concentrated in vacuo to provide 7.0 g of 1,4-bisbenzyloxy-2-methylbenzene as a pale yellow oil, which solidified on standing.

The dark insoluble residue from above was passed over a SiO₂ column with Et₂O/pentane (1:2) eluent. The appropriate fractions were pooled and concentrated in vacuo to provide 7.2 g 4-benzyloxy-2-methylphenol and 4-benzyloxy-3-methylphenol (approximately 1:1 mixture of monobenzylated isomers) as an orange solid, used in the next step without further purification.

2. (4-Benzyloxy-2-methylphenoxy)-acetonitrile. 4-Benzyloxy-2-methylphenol and 4-benzyloxy-3-methylphenol product from step 1 (5.76 g, 27 mmol) and bromoacetonitrile (3.24 g, 27 mmol) were dissolved in tetrahydrofuran (100 mL) in a 500 mL round bottom flask equipped with magnetic stir bar, reflux condenser and dry nitrogen line. The solution was treated with NaH (60% dispersion in oil; 1.4 g, 35 mmol) and stirred at room temperature overnight. The reaction mixture was diluted with dimethyl formamide (20 mL), and then stirred another 2 h at room temperature. The reaction mixture was concentrated in vacuo, then taken up in H₂O (200 mL). After adjusting pH to 4 with 2N HCl, the aqueous layer was washed with an equivolume of Et₂O/pentane (1:1). The organic layer was concentrated in vacuo to provide a yellow-brown oil (6.45 g). The oil was subjected to preparative HPLC to provide a slightly purified product, after pooling appropriate fractions. This product was extracted with boiling isopentane (3×100 mL) and the pooled isopentane fractions were concentrated in vacuo to provide 2.25 g of (4-benzyloxy-2-methylphenoxy)-acetonitrile (isomer A) and (4-benzyloxy-3-methylphenoxy)-acetonitrile (isomer B), approximately 2:1 mixture of A:B (determined by ¹H-NMR integrations), as a pale yellow oil. The insoluble residue was digested in boiling pentane, decanted, and cooled to room temperature. After 24 hours, crystals had formed. The supernatant was decanted, and concentrated in vacuo to provide 750 mg of isomers A and B in 1:3 ratio (¹H-NMR analysis). The crystals were found to be the desired isomer A. Successive pentane digestions of the crude residues and crystallization eventually led to the recovery of 1.95 g of the highly enriched (4-benzyloxy-2-methylphenoxy)-acetonitrile (isomer A).

3. 4-(2-Aminoethoxy)-3-methylphenol hydrochloride. (4-Benzyloxy-2-methylphenoxy)-acetonitrile (isomer A from Step 2; 1.95 g, 7.7 mmol) was dissolved in absolute ethanol (100 mL) in a Parr bottle. The solution was treated with con. aq. HCl (1.55 g) and 10% Pd—C (0.3 g), degassed, charged with hydrogen (55 psig), and shaken for 72 h. The suspension was filtered and concentrated in vacuo to afford 1.92 g 4-(2-aminoethoxy)-3-methylphenol hydrochloride as a beige solid, used without further purification: EIMS m/z 167 ([M]).

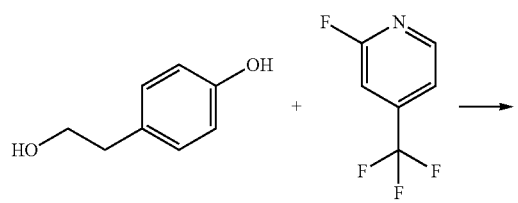

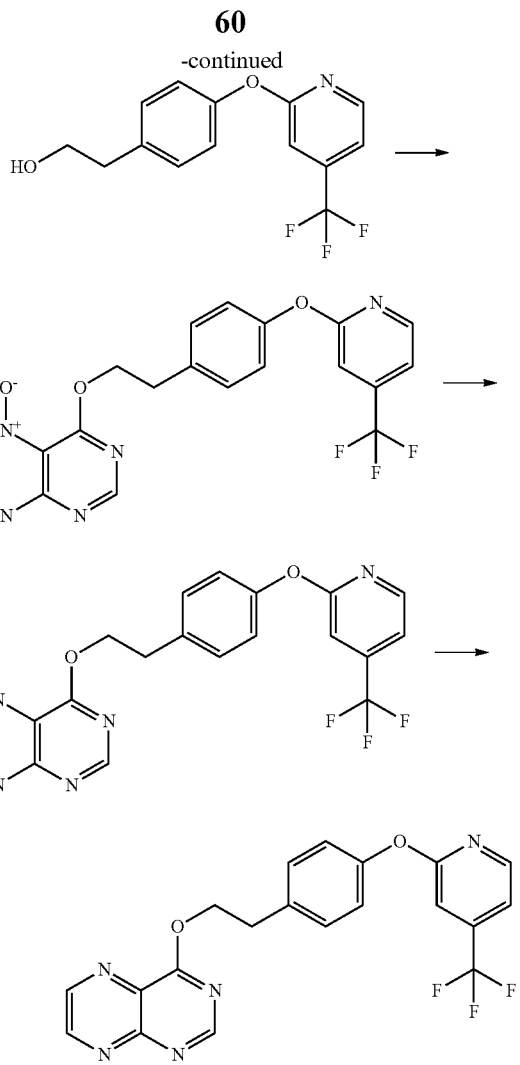

EXAMPLE 22

4-{2-[4-(4-Trifluoromethylpyridin-2-yloxy)-phenyl]-ethoxy}-pteridine.

1. 2-[4-(4-Trifluoromethylpyridin-2-yloxy)-phenyl]-ethanol 2-(4-Hydroxyphenyl)ethanol (4.0 g, 29 mmol), K₂CO₃ (8.0 g, 58 mmol) and 2-fluoro-4-trifluoromethylpyridine (3.6 g, 22 mmol) were combined in DMSO (30 mL) and stirred at 25° C. for 20 h. The mixture was poured into H₂O and extracted twice with Et₂O. The combined Et₂O extracts were washed with 1M NaOH, H₂O, brine, and concentrated in vacuo to give 2-[4-(4-trifluoromethylpyridin-2-yloxy)-phenyl]-ethanol (4.7 g; 57%), mp 78-79° C.; EIMS m/z 283; ¹H NMR (300 MHz, DMSO-d₆) δ 8.38 (d, J=5.3 Hz, 1H), 7.0-7.5 (m, 8H), 4.67 (t, J=5.0 Hz, 2H), 2.74 (t, J=5.2 Hz, 2H).

2. 4-Nitro-6-{2-[4-(4-trifluoromethylpyridin-2-yloxy)-phenyl]-ethoxy}-pyrimidin-5-ylamine. 2-[4-(4-Trifluoromethylpyridin-2-yloxy)-phenyl]-ethanol (product from Step 1; 400 mg, 1.4 mmol) was dissolved in DMSO (10 mL), treated with 95% NaH (36 mg, 1.5 mmol) and the mixture was warmed to 50-60° C. to produce a clear solution. Upon cooling the mixture was treated with 4-amino-5-nitro-6-chloropyrimidine (260 mg, 1.5 mmol) and heated at 45° C. for 6 h. After cooling the mixture was poured into H$_2$O (60 mL) and the precipitate was collected by suction filtration, washed with H$_2$O and air-dried on the filter: $^1$HNMR (300 MHz, CDCl$_3$) δ 8.39 (s, 1H), 8.33 (s, 1H), 8.18 (s, 1H), 7.38 (m, 2H), 7.15 (m, 4H), 4.69 (t, J=6.8 Hz, 2H), 3.15 (t, 6.6 Hz, 2H). This material was used in the next step without further purification.

3. 6-{2-[4-(4-Trifluoromethylpyridin-2-yloxy)-phenyl]-ethoxy}-pyrimidine-4,5-diamine. 4-Nitro-6-{2-[4-(4-trifluoromethylpyridin-2-yloxy)-phenyl]-ethoxy}-pyrimidin-5-ylamine was taken up in 75 mL absolute ethanol, treated with 100 mg 5% Pd/C and shaken under 50 psi hydrogen for 20 h. After removal of the catalyst by filtration, the crude diamino ether (6-{2-[4-(4-trifluoromethylpyridin-2-yloxy)-phenyl]-ethoxy}-pyrimidine-4,5-diamine) was obtained by removal of the solvent in vacuo to provide 6-{2-[4-(4-trifluoromethylpyridin-2-yloxy)-phenyl]-ethoxy}-pyrimidine-4,5-diamine, which was used in the next step without further purification.

4. 4-{2-[4-(4-Trifluoromethylpyridin-2-yloxy)-phenyl]-ethoxy}-pteridine. 6-{2-[4-(4-Trifluoromethylpyridin-2-yloxy)-phenyl]-ethoxy}-pyrimidine-4,5-diamine (75 mg, 0.19 mmol) was combined with 50% aqueous glyoxal solution (1 mL) in EtOH (5 mL) and stirred overnight at 25° C. The solution was evaporated and the residue extracted with CH$_2$Cl$_2$. The CH$_2$Cl$_2$ layer was washed with H$_2$O and concentrated in vacuo. The residue was recrystallized from hot MeCN to give 4-{2-[4-(4-trifluoromethyl-pyridin-2-yloxy)-phenyl]-ethoxy}-pteridine (16 mg, 20%): mp 172-173° C.; EIMS m/z 413; $^1$H NMR (300 MHz, CDCl$_3$) δ 9.24 (s, 1H), 9.07 (s, 1H), 9.02 (s, 1H), 8.30 (s, 1H), 7.43 (d, J=9.5 Hz, 2H), 7.28 (d, J=9.0 Hz, 2H), 4.63 (t, 6.8 Hz, 2H), 3.17 (t, J=7.0 Hz, 2H).

triphenylphosphine (310 mg, 1.2 mmol) were dissolved in dry THF (15 mL) and treated with rhenium bis-thiolate catalyst (5 mg; prepared according to Y. Wang and J.H. Espenson, Org. Lett., 2000, 2(22), 3525-26; expressly incorporated by reference herein). The mixture was stirred for 1.5 h, evaporated, and the residue purified by preparative RP-HPLC using 85% MeCN to give {2-[4-(4-tert-butylpyridin-2-yloxy)-phenyl]-ethyl}-pteridin-4-ylamine as a tan solid (155 mg, 32%): mp: 156-157° C.; ESIMS m/z 400 ([M+H]$^+$);. $^1$H NMR (300 MHz, CDCl$_3$) δ 9.02 (s, 1H), 8.82 (s, 1H), 8.62 (s, 1H), 8.08 (d, J=5.9 Hz, 1H), 6.9-7.3 (m, 7H), 3.99 (t, J=7.0 Hz, 2H), 3.055 (t, 7.0 Hz, 2H).

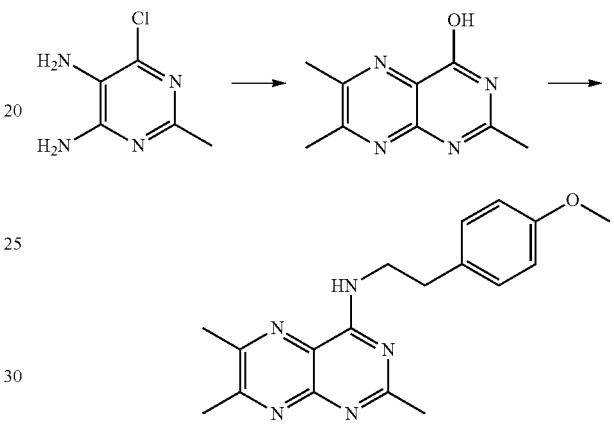

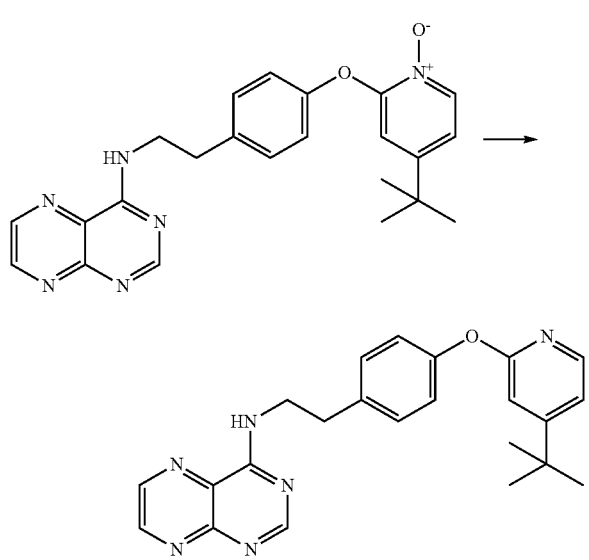 [SMILES: CC(C)(C)c1cc[n+]([O-])c(Oc2ccc(CCNc3ncnc4nccnc34)cc2)c1 ; CC(C)(C)c1ccnc(Oc2ccc(CCNc3ncnc4nccnc34)cc2)c1]

EXAMPLE 24

[2-(4-Methoxyphenyl)-ethyl]-(2,6,7-trimethylpteridin-4-yl)-amine.

1. 2,6,7-Trimethylpteridin-4(1H)-one: A mixture of 6-chloro-2-methylpyrimidine-4,5-diamine (3.2 g, 20 mmol) and 2,3-butanedione (3.6 g, 42 mmol) in n-butanol (40 mL) was stirred at 75-80° C. for 1 h. After cooling, the reaction was diluted with Et$_2$O (50 mL) and the solid collected by suction filtration. This was dried in vacuo affording, 2,6,7-trimethylpteridin-4(1H)-one (3.9 g), as a gold powder which was used in the next step without further purification.

2. [2-(4-Methoxyphenyl)-ethyl]-(2,6,7-trimethylpteridin-4-yl)-amine. A mixture of 2,6,7-trimethylpteridin-4(1H)-one (1.1 g, 6.0 mmol), 4-methoxyphenethylamine (1.6 g, 11 mmol) and ammonium sulfate (0.56 g, 4.2 mmol) in hexamethyldisilazane (16 mL) was heated at 115° C. for 6 h. After cooling, the majority of solids were dissolved by addition of CH$_2$Cl$_2$ and H$_2$O and the solvents removed in vacuo. The residue was slurried in a mixture of MeOH (5 mL) and H$_2$O (50 mL) and stirred for 45 min. The bronze solid was collected by suction filtration and dried in vacuo at 50° C. The residue was dissolved in MeOH/CH$_2$Cl$_2$ and diluted with Et$_2$O, causing crystallization. All solvent was allowed to evaporate, and the remaining solid dried in vacuo to afford [2-(4-methoxyphenyl)-ethyl]-(2,6,7-trimethylpteridin-4-yl)-amine as a brown powder (1.3 g; 67%): $^1$H NMR (300 MHz, CDCl$_3$) δ 7.22-7.14 (m, 2H), 6.95 (t, J=6.3 Hz, 1H), 6.90-6.83 (m, 2H), 3.87 (dd, J=13.5, 6.8 Hz, 2H), 3.80 (s, 3H), 2.97 (t, J=7.2 Hz, 2H), 2.69 (s, 3H), 2.66 (s, 3H), 2.61 (s, 3H).

EXAMPLE 23

{2-[4-(4-tert-Butylpyridin-2-yloxy)-phenyl]-ethyl}-pteridin-4-ylamine. {2-[4-(4-tert-Butyl-1-oxypyridin-2-yloxy)-phenyl]-ethyl}-pteridin-4-ylamine (500 mg, 1.2 mmol) and

TABLE 1

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 1 | 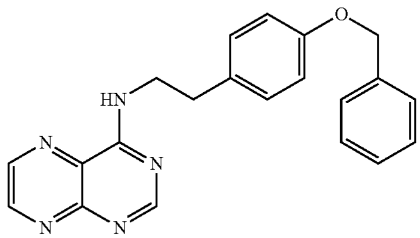 [SMILES: c1ccc(COc2ccc(CCNc3ncnc4nccnc34)cc2)cc1] | | Preparation 1 | 1 |
| 2 | 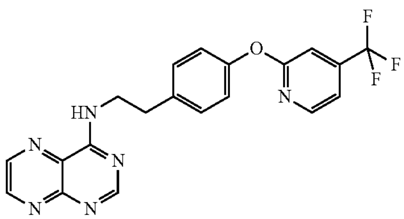 [SMILES: FC(F)(F)c1ccnc(Oc2ccc(CCNc3ncnc4nccnc34)cc2)c1] | Knox, I. L.; Rogers, R. B. U.S. Pat. No. 4,775,762, 1988. | 4 | 3 Alt. |
| 3 | 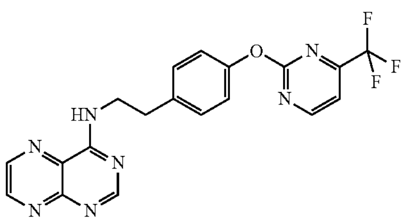 [SMILES: FC(F)(F)c1ccnc(Oc2ccc(CCNc3ncnc4nccnc34)cc2)n1] | | 4 | 3 |
| 4 | 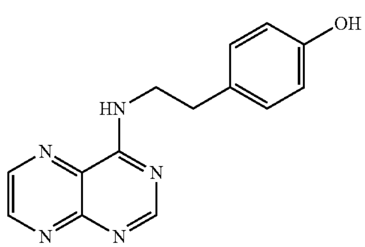 [SMILES: Oc1ccc(CCNc2ncnc3nccnc23)cc1] | Albert, A.; Ohta, K. *J. Chem. Soc. C* 1971, 3727-3730. | | 2 |
| 5 | 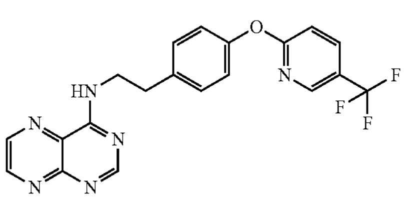 [SMILES: FC(F)(F)c1ccc(Oc2ccc(CCNc3ncnc4nccnc34)cc2)nc1] | | 4 | 3 |
| 6 | 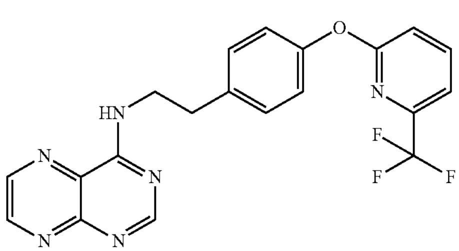 [SMILES: FC(F)(F)c1cccc(Oc2ccc(CCNc3ncnc4nccnc34)cc2)n1] | | 4 | 3 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 7 | (structure) | (2,6-difluoropyridine structure) | 4 | 3 |
| 8 | (structure) | (2-chloro-4-cyanopyridine structure) | 4 | 3 |
| 9 | (structure) | (pyrazine-N=CHN(CH3)2 cyano structure) Albert, A.; Ohta, K. *J. Chem. Soc. C* 1971, 3727-3730. | (1-phenylethylamine structure) | 2 |
| 10 | (structure) | 7 | methanol | 5 |
| 11 | (structure) | 7 | trifluoroethanol | As in Ex. 5 |
| 12 | (structure) | 7 | ethanol | As in Ex. 5 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 13 | (pteridinyl-NH-CH2CH2-C6H4-O-pyridine-CN) | (Cl-pyridine-CN) | 4 | 3 |
| 14 | (pteridinyl-NH-CH2CH2-C6H4-O-pyridine-CN) | (Cl-pyridine-CN) | 4 | 3 |
| 15 | (pteridinyl-NH-CH2CH2-C6H4-O-pyrimidine) | (Cl-pyrimidine) | 4 | 3 |
| 16 | (pteridinyl-NH-CH2CH2-C6H4-O-pyrimidine-OCH3) | (Cl-pyrimidine-OCH3) | 4 | 3 |
| 17 | (pteridinyl-NH-CH(CH3)-C6H4-OCH3) | (pyrazine-CN with N=CH-N(CH3)2); Albert, A.; Ohta, K. J. Chem. Soc. C 1971, 3727-3730. | (H2N-CH(CH3)-C6H4-OCH3) | 2 |
| 18 | (pteridinyl-NH-CH2CH2-C6H4-O-pyrazine-CN) | (NC-pyrazine-Cl) | 4 | 3 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 19 | 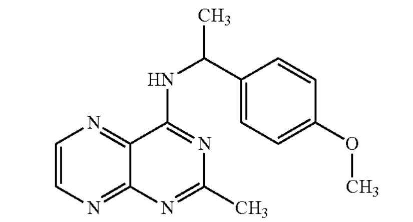 [SMILES: COc1ccc(C(C)Nc2nc(C)nc3nccnc23)cc1] | | | 6 |
| 20 | 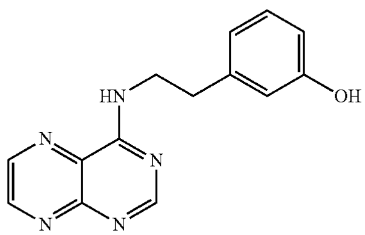 [SMILES: Oc1cccc(CCNc2ncnc3nccnc23)c1] | Albert, A.; Ohta, K. *J. Chem. Soc. C* 1971, 3727-3730. | | 2 |
| 21 | 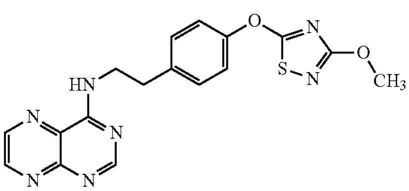 [SMILES: COc1nsc(Oc2ccc(CCNc3ncnc4nccnc34)cc2)n1] | Leung-Toung, R. et al., *Bioorg. Med. Chem.* 2003, 11, 5529-5537. | 4 | 4 |
| 22 | 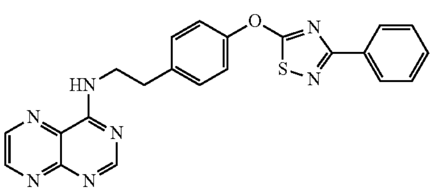 [SMILES: c1ccc(-c2nsc(Oc3ccc(CCNc4ncnc5nccnc45)cc3)n2)cc1] | Leung-Toung, R. et al., *Bioorg. Med. Chem.* 2003, 11, 5529-5537. | 4 | 4 |
| 23 | 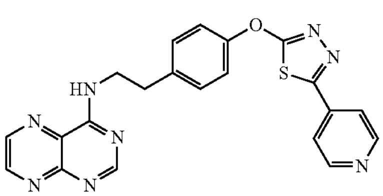 [SMILES: c1cc(-c2nnc(Oc3ccc(CCNc4ncnc5nccnc45)cc3)s2)ccn1] | | 4 | 4 |
| 24 | 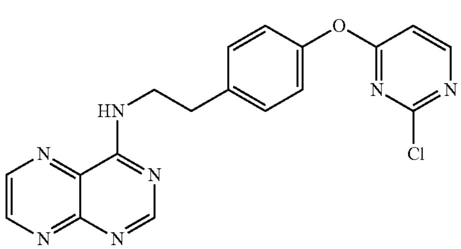 [SMILES: Clc1nccc(Oc2ccc(CCNc3ncnc4nccnc34)cc2)n1] | | 4 | 3 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 25 | 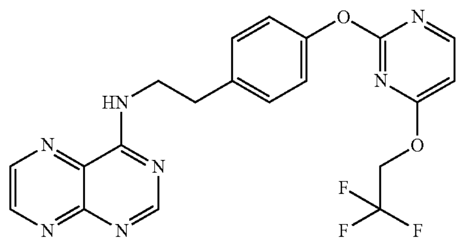 [SMILES: FC(F)(F)COc1ccnc(Oc2ccc(CCNc3ncnc4nccnc34)cc2)n1] | Preparation 2 | 4 | 3 |
| 26 | 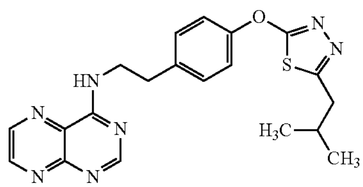 [SMILES: CC(C)Cc1nnc(Oc2ccc(CCNc3ncnc4nccnc34)cc2)s1] | | 4 | 4 |
| 27 | 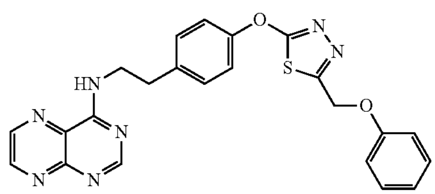 [SMILES: c1ccc(OCc2nnc(Oc3ccc(CCNc4ncnc5nccnc45)cc3)s2)cc1] | Yadav, L. D. S. et al., *Pest. Sci.* 1989, 25, 219-225. | 4 | 4 |
| 28 | 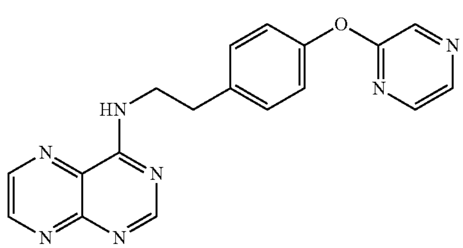 [SMILES: c1cnc(Oc2ccc(CCNc3ncnc4nccnc34)cc2)cn1] | | 4 | 4 |
| 29 | 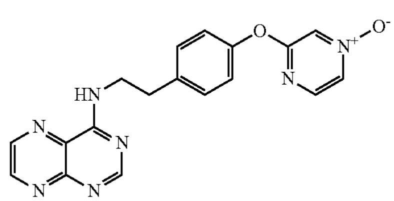 [SMILES: [O-][n+]1ccnc(Oc2ccc(CCNc3ncnc4nccnc34)cc2)c1] | Mixan, C. E.; Pews, R. G. *J. Org. Chem.* 1977, 42, 1869-1871 | 4 | 4 |
| 30 | 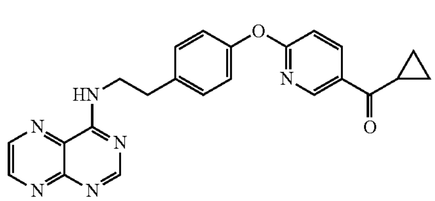 [SMILES: O=C(c1ccc(Oc2ccc(CCNc3ncnc4nccnc34)cc2)nc1)C1CC1] | Wang, X.-J. et al., *Org. Lett.* 2005, 7, 5593-5595. | 4 | 4 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 31 | 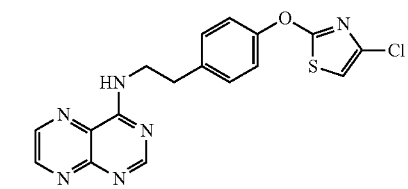 [SMILES: Clc1csc(Oc2ccc(CCNc3ncnc4nccnc34)cc2)n1] | | 4 | 4 |
| 32 | 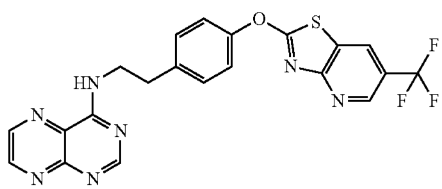 [SMILES: FC(F)(F)c1cnc2nc(Oc3ccc(CCNc4ncnc5nccnc45)cc3)sc2c1] | Smith, R. et al., WO 200604475 A2, 2006. | 4 | 4 |
| 33 | 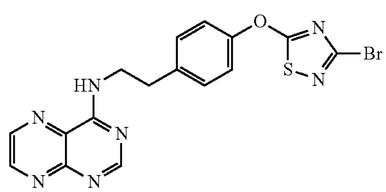 [SMILES: Brc1nsc(Oc2ccc(CCNc3ncnc4nccnc34)cc2)n1] | | 4 | 4 |
| 34 | 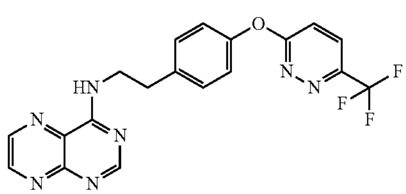 [SMILES: FC(F)(F)c1ccc(Oc2ccc(CCNc3ncnc4nccnc34)cc2)nn1] | Goodman, A. J. et al., *Tetrahedron* 1999, 55, 15067-15070. | 4 | 4 |
| 35 | 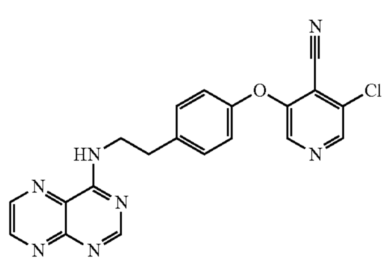 [SMILES: N#Cc1c(Cl)cncc1Oc1ccc(CCNc2ncnc3nccnc23)cc1] | | 4 | 3 |
| 36 | 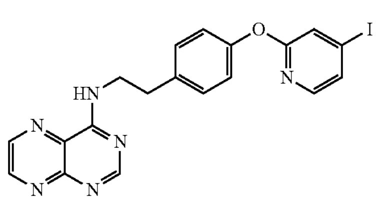 [SMILES: Ic1ccnc(Oc2ccc(CCNc3ncnc4nccnc34)cc2)c1] | | 4 | 3 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 37 | 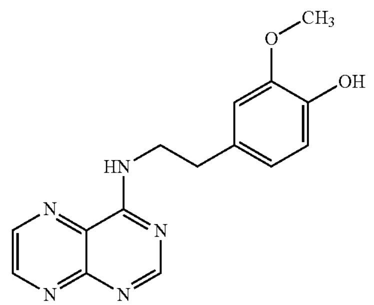 [SMILES: COc1cc(CCNc2ncnc3nccnc23)ccc1O] | Albert, A.; Ohta, K. *J. Chem. Soc. C* 1971, 3727-3730. | | 2 |
| 38 | 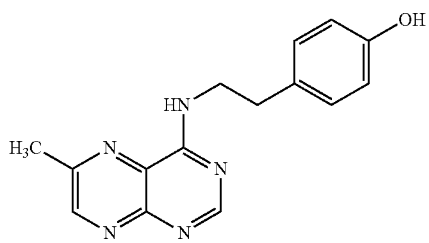 [SMILES: Cc1cnc2ncnc(NCCc3ccc(O)cc3)c2n1] | Taylor, E. C.; LaMattina, J. L. *J. Org. Chem.* 1977, 42, 1523-1527. | | 2 |
| 39 | 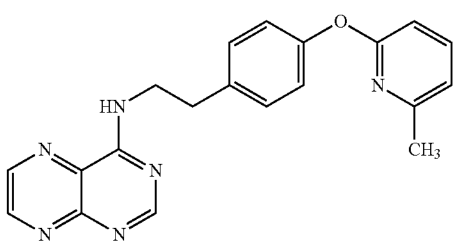 [SMILES: Cc1cccc(Oc2ccc(CCNc3ncnc4nccnc34)cc2)n1] | | | 4 |
| 40 | 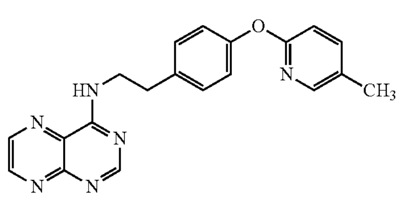 [SMILES: Cc1ccc(Oc2ccc(CCNc3ncnc4nccnc34)cc2)nc1] | | | 4 |
| 41 | 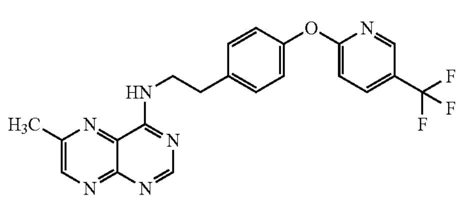 [SMILES: Cc1cnc2ncnc(NCCc3ccc(Oc4ccc(C(F)(F)F)cn4)cc3)c2n1] | | 38 | 3 |
| 42 | 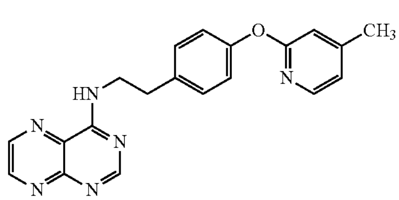 [SMILES: Cc1ccnc(Oc2ccc(CCNc3ncnc4nccnc34)cc2)c1] | | | 4 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 43 | (structure) | (3-methyl-2-fluoropyridine structure) | 4 | 4 |
| 44 | (structure) | (structure) Preparation 4 | 4 | 4 |
| 45 | (structure) | (structure) Albert, A.; Ohta, K. *J. Chem. Soc. C* 1971, 3727-3730. | (4-methoxyphenethylamine structure) | 2 |
| 46 | (structure) | (4-CF₃-2-chloropyridine structure) | 20 | 4 |
| 47 | (structure) | (5-CF₃-2-chloropyridine structure) | 20 | 4 |
| 48 | (structure) | (2-bromothiazole structure) | 4 | 3 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 49 | 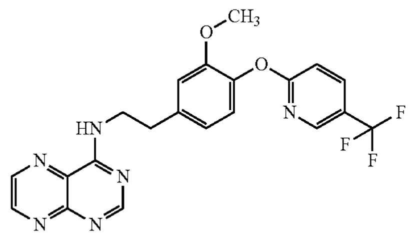 [SMILES: COc1cc(CCNc2ncnc3nccnc23)ccc1Oc1ccc(C(F)(F)F)cn1] | | 37 | 3 |
| 50 | 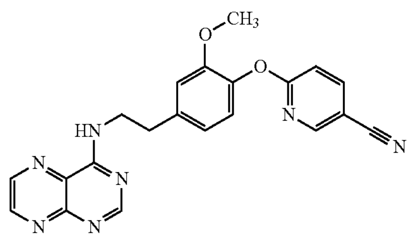 [SMILES: COc1cc(CCNc2ncnc3nccnc23)ccc1Oc1ccc(C#N)cn1] | | 37 | 3 |
| 51 | 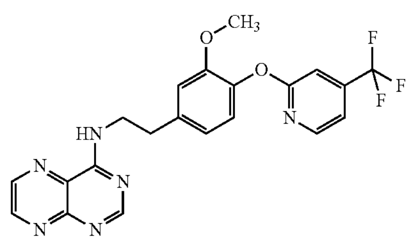 [SMILES: COc1cc(CCNc2ncnc3nccnc23)ccc1Oc1cc(C(F)(F)F)ccn1] | | 37 | 3 |
| 52 | 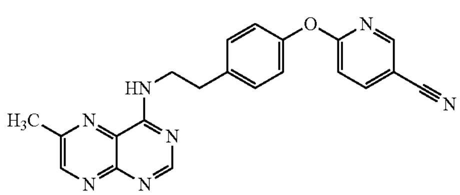 [SMILES: Cc1cnc2ncnc(NCCc3ccc(Oc4ccc(C#N)cn4)cc3)c2n1] | | 38 | 3 |
| 53 | 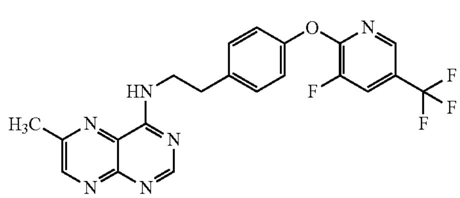 [SMILES: Cc1cnc2ncnc(NCCc3ccc(Oc4ncc(C(F)(F)F)cc4F)cc3)c2n1] | | 38 | 3 |
| 54 | 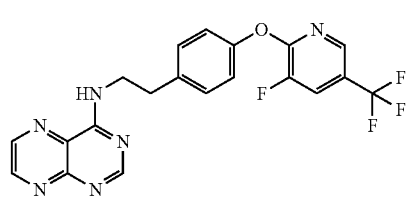 [SMILES: Fc1cc(C(F)(F)F)cnc1Oc1ccc(CCNc2ncnc3nccnc23)cc1] | | 4 | 3 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 55 | 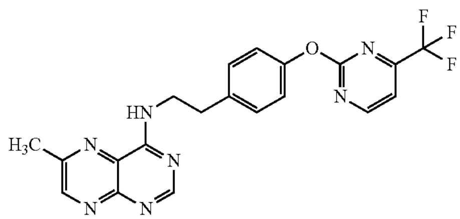 [SMILES: Cc1cnc2ncnc(NCCc3ccc(Oc4nccc(C(F)(F)F)n4)cc3)c2n1] | | 38 | 3 |
| 56 | 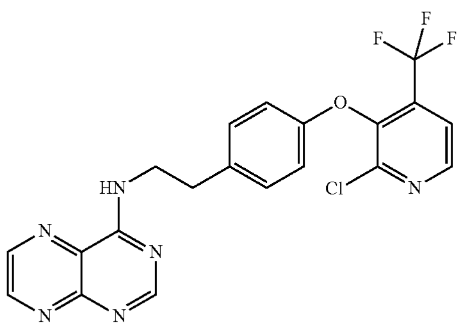 [SMILES: FC(F)(F)c1ccnc(Cl)c1Oc1ccc(CCNc2ncnc3nccnc23)cc1] | | 4 | 4 |
| 57 | 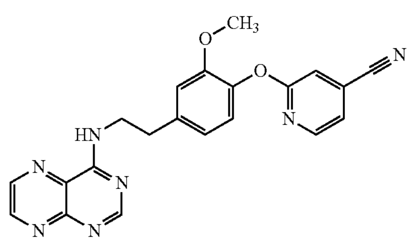 [SMILES: COc1cc(CCNc2ncnc3nccnc23)ccc1Oc1cc(C#N)ccn1] | | 37 | 3 |
| 58 | 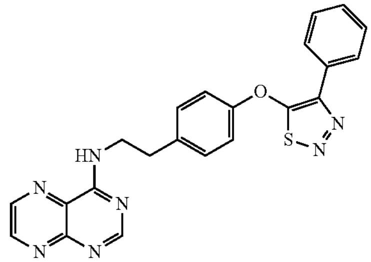 [SMILES: c1ccc(-c2nnsc2Oc2ccc(CCNc3ncnc4nccnc34)cc2)cc1] | | 4 | 4 |
| 59 | 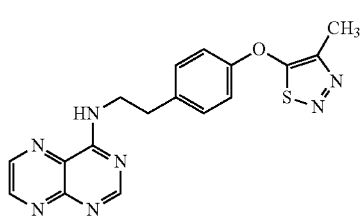 [SMILES: Cc1nnsc1Oc1ccc(CCNc2ncnc3nccnc23)cc1] | | 4 | 4 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 60 | 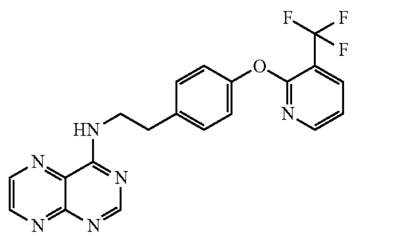 [SMILES: FC(F)(F)c1cccnc1Oc1ccc(CCNc2ncnc3nccnc23)cc1] | | 4 | 4 |
| 61 | 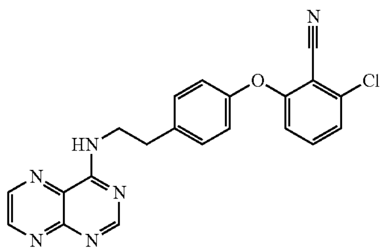 | | 4 | 3 |
| 62 | 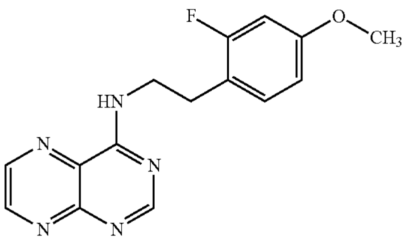 [SMILES: COc1ccc(CCNc2ncnc3nccnc23)c(F)c1] | Albert, A.; Ohta, K. *J. Chem. Soc. C* 1971, 3727-3730. | Preparation 5 | 2 |
| 63 | 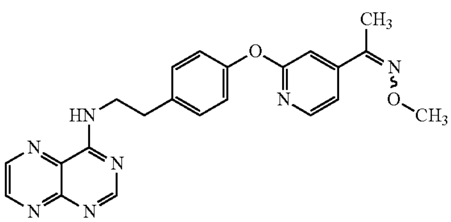 [SMILES: CON=C(C)c1ccnc(Oc2ccc(CCNc3ncnc4nccnc34)cc2)c1] | Preparation 6 | 4 | 4 |
| 64 | 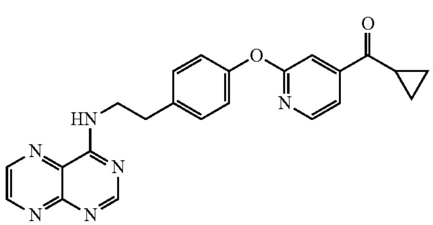 [SMILES: O=C(c1ccnc(Oc2ccc(CCNc3ncnc4nccnc34)cc2)c1)C1CC1] | Wang, X.-J. et al., *Org. Lett.* 2005, 7, 5593-5595. | 4 | 4 |
| 65 | 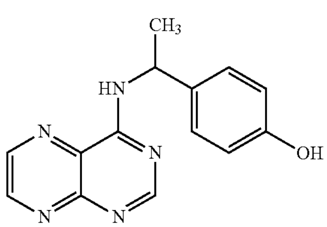 [SMILES: CC(Nc1ncnc2nccnc12)c1ccc(O)cc1] | | | Preparation 7 and Example 7 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 66 | 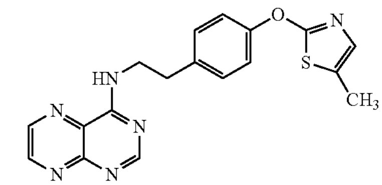 [SMILES: Cc1cnc(Oc2ccc(CCNc3ncnc4nccnc34)cc2)s1] | | 4 | 4 |
| 67 | 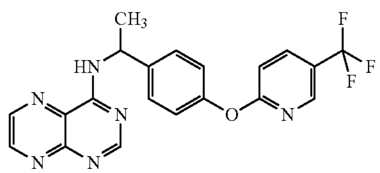 [SMILES: CC(Nc1ncnc2nccnc12)c1ccc(Oc2ccc(C(F)(F)F)cn2)cc1] | | 65 | 3 |
| 68 | 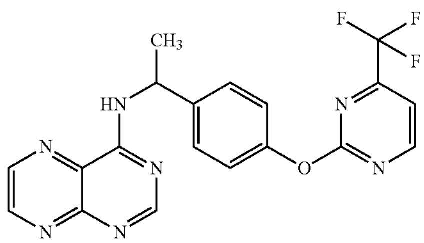 [SMILES: CC(Nc1ncnc2nccnc12)c1ccc(Oc2nccc(C(F)(F)F)n2)cc1] | | 65 | 3 |
| 69 | 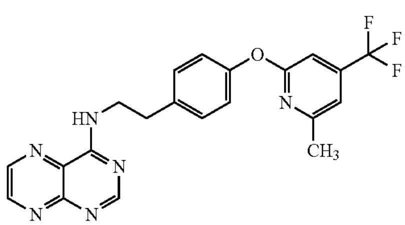 [SMILES: Cc1cc(C(F)(F)F)cc(Oc2ccc(CCNc3ncnc4nccnc34)cc2)n1] | | 4 | 4 |
| 70 | 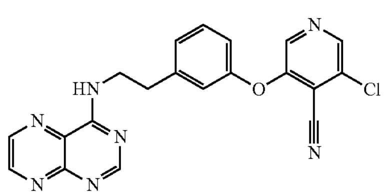 [SMILES: N#Cc1c(Cl)cncc1Oc1cccc(CCNc2ncnc3nccnc23)c1] | | 20 | 4 |
| 71 | 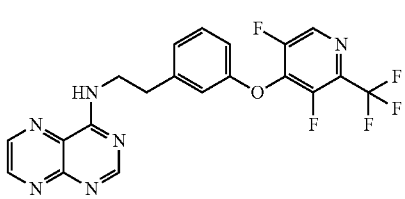 [SMILES: Fc1cnc(C(F)(F)F)c(F)c1Oc1cccc(CCNc2ncnc3nccnc23)c1] | | 20 | 4 |

Scovell, E. G.; Watson, D. J.
EP 63872 A1, 1982.

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 72 | 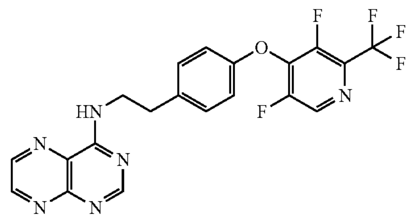 [SMILES: Fc1cnc(C(F)(F)F)c(F)c1Oc1ccc(CCNc2ncnc3nccnc23)cc1] | Scovell, E. G.; Watson, D. J. EP 63872 A1, 1982. | 4 | 4 |
| 73 | 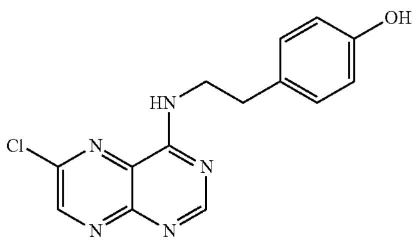 [SMILES: Oc1ccc(CCNc2ncnc3ncc(Cl)nc23)cc1] | Cragoe, E. J., Jr.; Holden, J. H. U.S. Pat. No. 3,299,063, 1967. | | 2 |
| 74 | 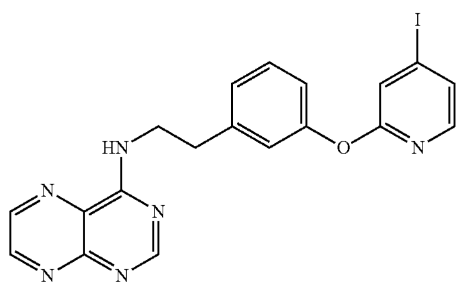 [SMILES: Ic1ccnc(Oc2cccc(CCNc3ncnc4nccnc34)c2)c1] | | 20 | 4 |
| 75 | 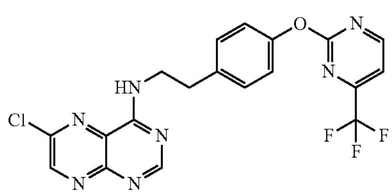 [SMILES: FC(F)(F)c1ccnc(Oc2ccc(CCNc3ncnc4ncc(Cl)nc34)cc2)n1] | | 73 | 3 |
| 76 | 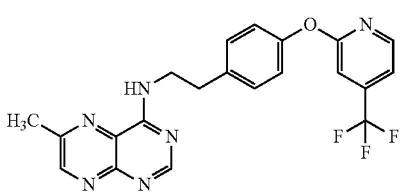 [SMILES: Cc1cnc2ncnc(NCCc3ccc(Oc4cc(C(F)(F)F)ccn4)cc3)c2n1] | Knox, I. L.; Rogers, R. B. U.S. Pat. No. 4,775,762, 1988. | 38 | 3 |
| 77 | 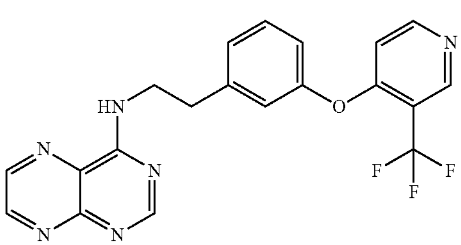 [SMILES: FC(F)(F)c1cnccc1Oc1cccc(CCNc2ncnc3nccnc23)c1] | | 20 | 4 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 78 | (pteridine-S-CH(CH3)-C6H4-CN) | Cl-CH(CH3)-C6H4-CN | pteridine-SH; Brimm, E. O. et al., *J. Chem. Soc.* 1954, 3832-3839. | 3 |
| 79 | (pteridine-S-CH(CH3)-C6H4-CF3) | CF3-C6H4-CH(Br)CH3 | pteridine-SH; Brimm, E. O. et al., *J. Chem. Soc.* 1954, 3832-3839. | 3 |
| 80 | (pteridine-NH-CH2CH2-O-C6H4-OH, para) | pyrazine with CN and N=CH-N(CH3)2; Albert, A.; Ohta, K. *J. Chem. Soc. C* 1971, 3727-3730. | H2N-CH2CH2-O-C6H4-OH (para); Preparation 8 | 2 |
| 81 | (pteridine-NH-CH2CH2-O-C6H4-OH, meta) | pyrazine with CN and N=CH-N(CH3)2; Albert, A.; Ohta, K. *J. Chem. Soc. C* 1971, 3727-3730. | H2N-CH2CH2-O-C6H4-OH (meta); Preparation 8 | 2 |
| 82 | (pteridine-NH-CH(CH3)-C6H4-O-pyridine-CF3) | 2-F-4-CF3-pyridine; Knox, I. L.; Rogers, R. B. U.S. Pat. No. 4,775,762, 1988. | 65 | 3 |
| 83 | (pteridine-NH-CH2CH2-O-C6H4-O-pyridine-CF3) | 2-F-4-CF3-pyridine; Knox, I. L.; Rogers, R. B. U.S. Pat. No. 4,775,762, 1988. | 80 | 3 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 84 | *structure* | 2-chloro-5-(trifluoromethyl)pyridine | 80 | 3 |
| 85 | *structure* | 2-chloro-4-cyanopyridine | 80 | 3 |
| 86 | *structure* | 2-fluoro-4-(trifluoromethyl)pyridine<br>Knox, I. L.; Rogers, R. B. U.S. Pat. No. 4,775,762, 1988 | 81 | 3 |
| 87 | *structure* | 2-chloro-5-(trifluoromethyl)pyridine | 81 | 3 |
| 88 | *structure* | 2-chloro-4-cyanopyridine | 81 | 3 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 89 | 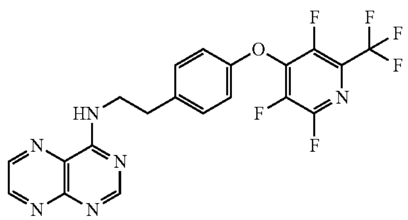 [SMILES: Fc1nc(C(F)(F)F)c(F)c(Oc2ccc(CCNc3ncnc4nccnc34)cc2)c1F] | Weigert, F. J. U.S. Pat. No. 4,910,351, 1990. | 4 | 3 |
| 90 | 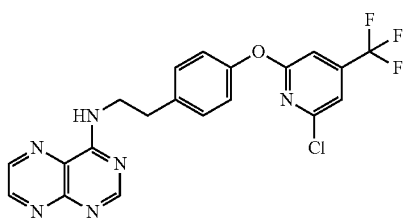 [SMILES: FC(F)(F)c1cc(Cl)nc(Oc2ccc(CCNc3ncnc4nccnc34)cc2)c1] | Fung, A. J. U.S. Pat. No. 4,590,279, 1986. | 4 | 3 |
| 91 | 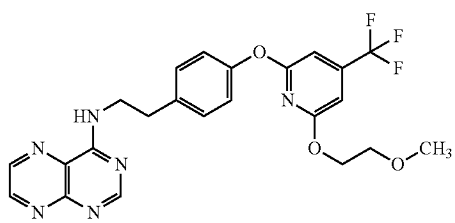 [SMILES: COCCOc1cc(C(F)(F)F)cc(Oc2ccc(CCNc3ncnc4nccnc34)cc2)n1] | 90 | 2-methoxyethanol | 8 |
| 92 | 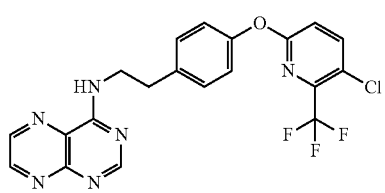 [SMILES: FC(F)(F)c1nc(Oc2ccc(CCNc3ncnc4nccnc34)cc2)ccc1Cl] | JP 58206563 A, 1983. | 4 | 3 |
| 93 | 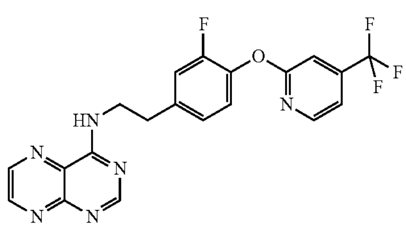 [SMILES: Fc1cc(CCNc2ncnc3nccnc23)ccc1Oc1cc(C(F)(F)F)ccn1] | | 177 | 4 |
| 94 | 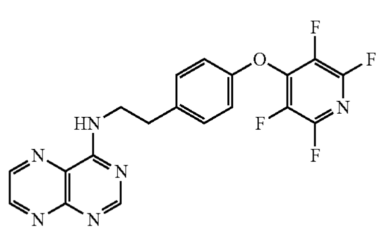 [SMILES: Fc1nc(F)c(F)c(Oc2ccc(CCNc3ncnc4nccnc34)cc2)c1F] | | 4 | 3 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 95 | 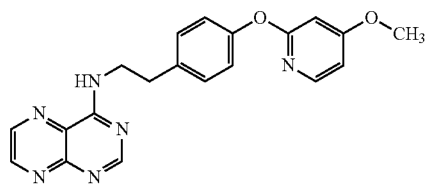 [SMILES: COc1ccnc(Oc2ccc(CCNc3ncnc4nccnc34)cc2)c1] | 36 | methanol | 9 |
| 96 | 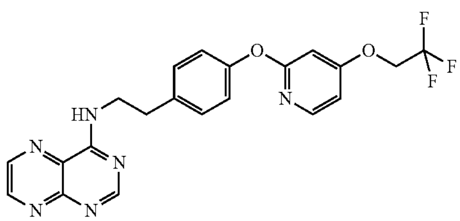 [SMILES: FC(F)(F)COc1ccnc(Oc2ccc(CCNc3ncnc4nccnc34)cc2)c1] | 36 | 2,2,2-trifluoroethanol | 9 |
| 97 | 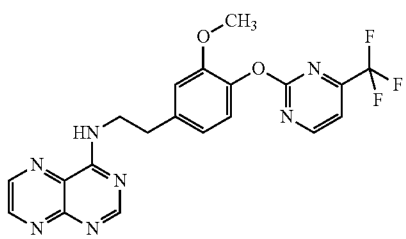 [SMILES: COc1cc(CCNc2ncnc3nccnc23)ccc1Oc1nccc(C(F)(F)F)n1] | | 37 | 3 |
| 98 | 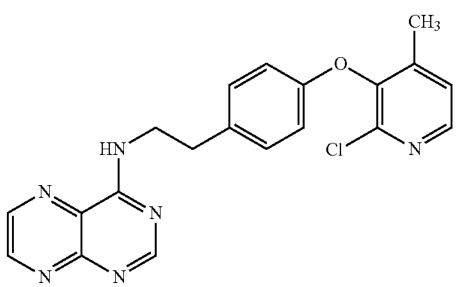 [SMILES: Cc1ccnc(Cl)c1Oc1ccc(CCNc2ncnc3nccnc23)cc1] | | 4 | 4 |
| 99 | 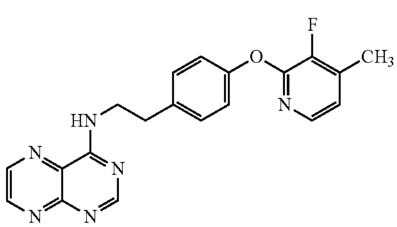 [SMILES: Cc1ccnc(Oc2ccc(CCNc3ncnc4nccnc34)cc2)c1F] | | 4 | 4 |
| 100 | 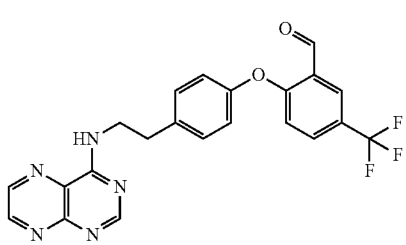 [SMILES: O=Cc1cc(C(F)(F)F)ccc1Oc1ccc(CCNc2ncnc3nccnc23)cc1] | | 4 | 3 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 101 | 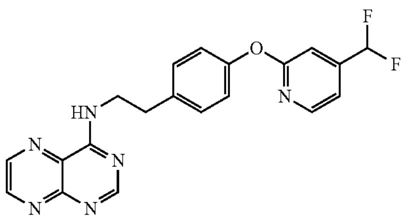 [SMILES: FC(F)c1ccnc(Oc2ccc(CCNc3ncnc4nccnc34)cc2)c1] | Cartwright, D. Brit. GB Pat. Appl. 2002368 | 4 | 4 |
| 102 | 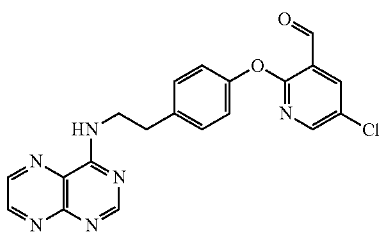 [SMILES: O=Cc1cc(Cl)cnc1Oc1ccc(CCNc2ncnc3nccnc23)cc1] | Bayer A.-G. DE 4429465 A1, 1994. | 4 | 3 |
| 103 | 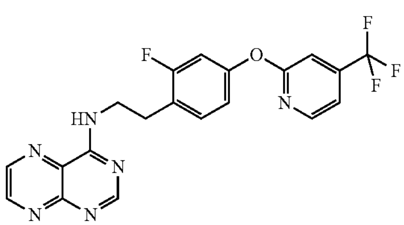 [SMILES: Fc1cc(Oc2cc(C(F)(F)F)ccn2)ccc1CCNc1ncnc2nccnc12] | | 220 | 3 |
| 104 | 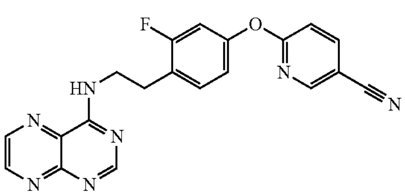 [SMILES: N#Cc1ccc(Oc2ccc(CCNc3ncnc4nccnc34)c(F)c2)nc1] | | 220 | 3 |
| 105 | 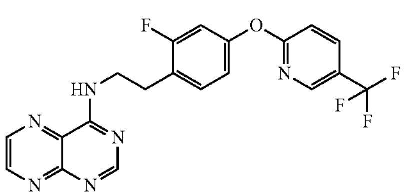 [SMILES: Fc1cc(Oc2ccc(C(F)(F)F)cn2)ccc1CCNc1ncnc2nccnc12] | | 220 | 3 |
| 106 | 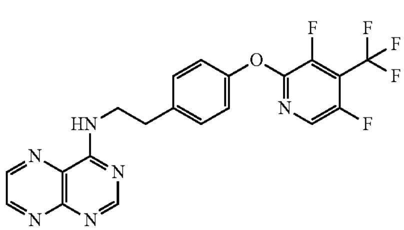 [SMILES: Fc1cnc(Oc2ccc(CCNc3ncnc4nccnc34)cc2)c(F)c1C(F)(F)F] | | 4 | 3 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 107 | 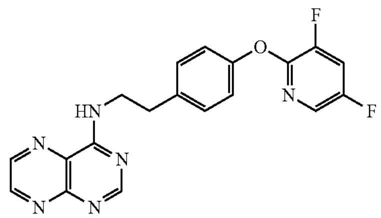 [SMILES: Fc1cnc(Oc2ccc(CCNc3ncnc4nccnc34)cc2)c(F)c1] | | 4 | 3 |
| 108 | 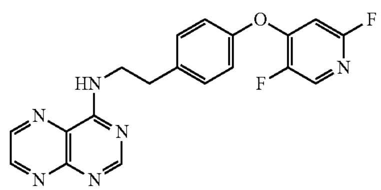 [SMILES: Fc1cc(Oc2ccc(CCNc3ncnc4nccnc34)cc2)c(F)cn1] | | 4 | 3 |
| 109 | 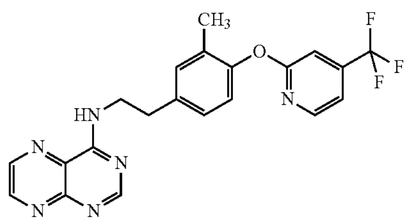 | | 174 | 4 |
| 110 | 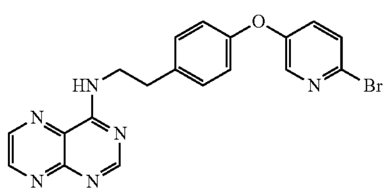 [SMILES: Brc1ccc(Oc2ccc(CCNc3ncnc4nccnc34)cc2)cn1] | | 4 | 3 |
| 111 | 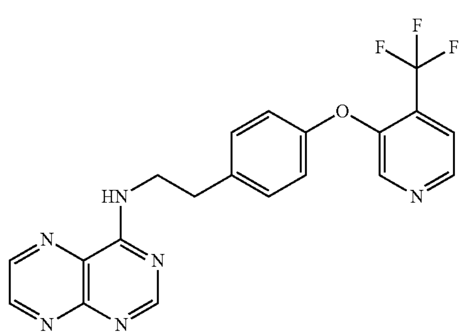 [SMILES: FC(F)(F)c1ccncc1Oc1ccc(CCNc2ncnc3nccnc23)cc1] | | 4 | 3 |
| 112 | 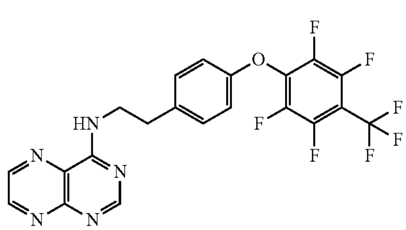 [SMILES: Fc1c(F)c(C(F)(F)F)c(F)c(F)c1Oc1ccc(CCNc2ncnc3nccnc23)cc1] | | 4 | 3 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 113 | 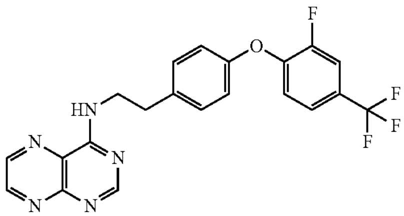 [SMILES: Fc1cc(C(F)(F)F)ccc1Oc1ccc(CCNc2ncnc3nccnc23)cc1] | | 4 | 3 |
| 114 | 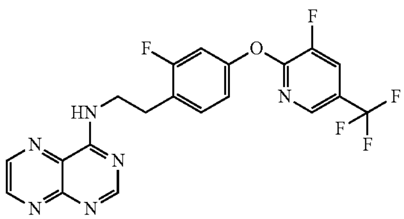 [SMILES: Fc1cc(Oc2ncc(C(F)(F)F)cc2F)ccc1CCNc1ncnc2nccnc12] | | 220 | 3 |
| 115 | 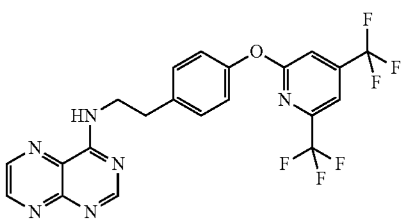 [SMILES: FC(F)(F)c1cc(Oc2ccc(CCNc3ncnc4nccnc34)cc2)nc(C(F)(F)F)c1] | | 4 | 4 |
| 116 | 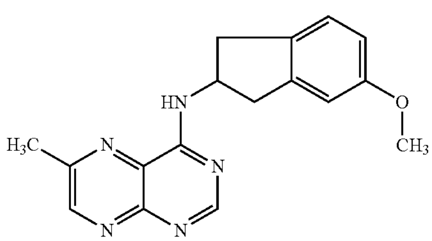 | Taylor, E. C.; LaMattina, J. L. J. Org. Chem. 1977, 42, 1523-1527. | | 2 |
| 117 | 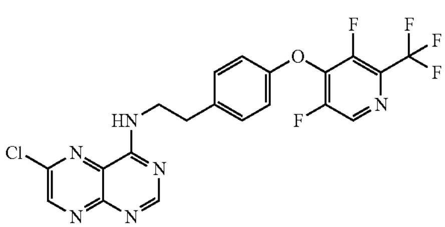 [SMILES: Fc1cnc(C(F)(F)F)c(F)c1Oc1ccc(CCNc2ncnc3ncc(Cl)nc23)cc1] | Scovell, E. G.; Watson, D. J. EP 63872 A1, 1982. | 73 | 3 |
| 118 | 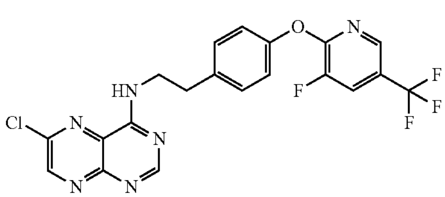 [SMILES: Fc1cc(C(F)(F)F)cnc1Oc1ccc(CCNc2ncnc3ncc(Cl)nc23)cc1] | | 73 | 3 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 119 | 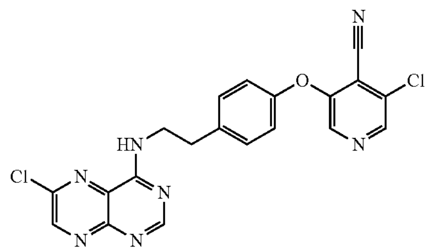 [SMILES: N#Cc1c(Cl)cncc1Oc1ccc(CCNc2ncnc3ncc(Cl)nc23)cc1] | 3,5-dichloro-4-cyanopyridine structure | 73 | 3 |
| 120 | 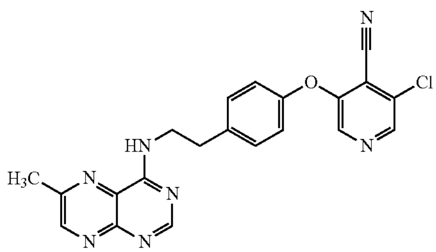 [SMILES: Cc1cnc2ncnc(NCCc3ccc(Oc4cncc(Cl)c4C#N)cc3)c2n1] | 3,5-dichloro-4-cyanopyridine structure | 38 | 3 |
| 121 | 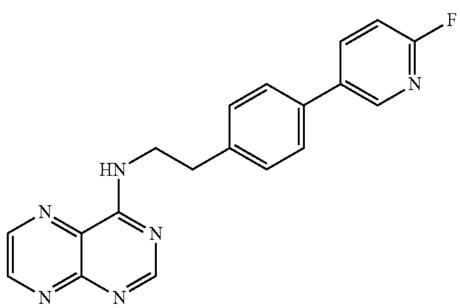 [SMILES: Fc1ccc(-c2ccc(CCNc3ncnc4nccnc34)cc2)cn1] | 222 | 6-fluoropyridine-3-boronic acid | 10 |
| 122 | 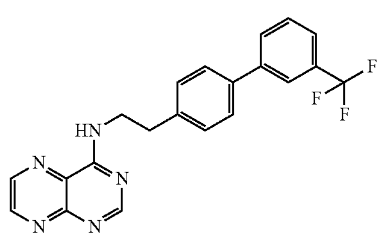 [SMILES: FC(F)(F)c1cccc(-c2ccc(CCNc3ncnc4nccnc34)cc2)c1] | 222 | 3-trifluoromethylbenzene boronic acid | 10 |
| 123 | 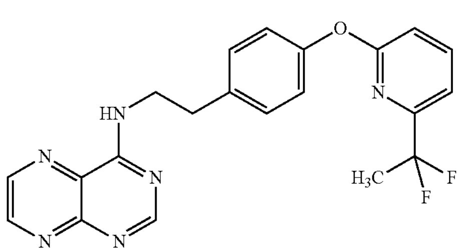 [SMILES: CC(F)(F)c1cccc(Oc2ccc(CCNc3ncnc4nccnc34)cc2)n1] | Preparation 4 | 4 | 4 |
| 124 | 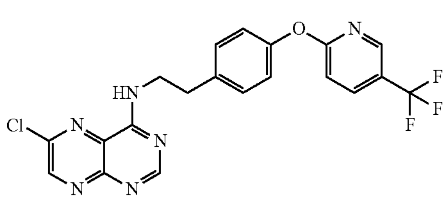 | | 73 | 3 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 125 | 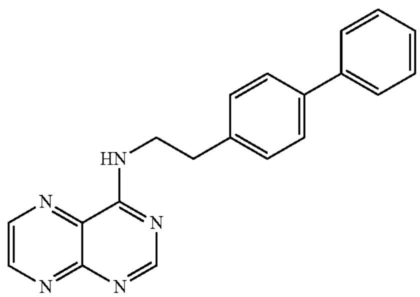 [SMILES: c1ccc(-c2ccc(CCNc3ncnc4nccnc34)cc2)cc1] | 222 | benzene boronic acid | 10 |
| 126 | 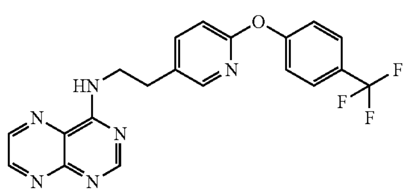 [SMILES: FC(F)(F)c1ccc(Oc2ccc(CCNc3ncnc4nccnc34)cn2)cc1] | | Preparation 9 | 2 |
| | | Albert, A.; Ohta, K. J. Chem. Soc. C 1971, 3727-3730. | | |
| 127 | 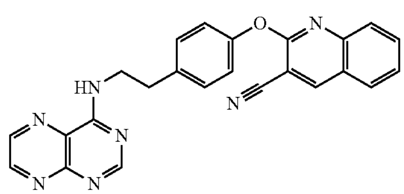 [SMILES: N#Cc1cc2ccccc2nc1Oc1ccc(CCNc2ncnc3nccnc23)cc1] | | 4 | 3 |
| | | Wright, T. L. US 4540786 A, 1985. | | |
| 128 | 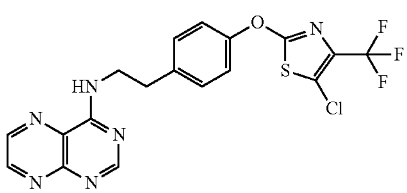 [SMILES: FC(F)(F)c1nc(Oc2ccc(CCNc3ncnc4nccnc34)cc2)sc1Cl] | | 4 | 3 |
| 129 | 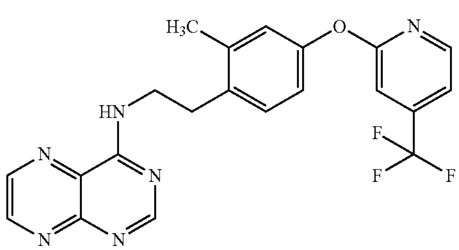 [SMILES: Cc1cc(Oc2cc(C(F)(F)F)ccn2)ccc1CCNc1ncnc2nccnc12] | | 224 | 4 |
| 130 | 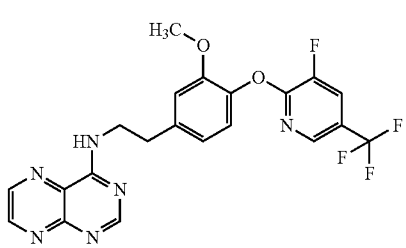 [SMILES: COc1cc(CCNc2ncnc3nccnc23)ccc1Oc1ncc(C(F)(F)F)cc1F] | | 37 | 3 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 131 | 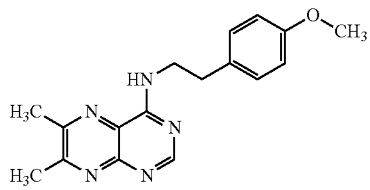 | Preparation 10 | | 1 |
| 132 | 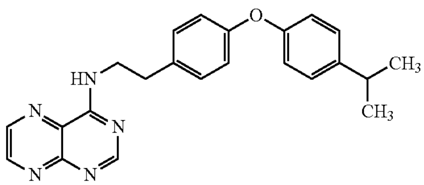 [SMILES: CC(C)c1ccc(Oc2ccc(CCNc3ncnc4nccnc34)cc2)cc1] | | 4 | 11 |
| 133 | 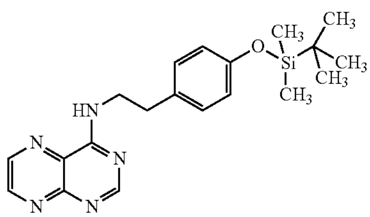 [SMILES: CC(C)(C)[Si](C)(C)Oc1ccc(CCNc2ncnc3nccnc23)cc1] | | 4 | 12 |
| 134 | 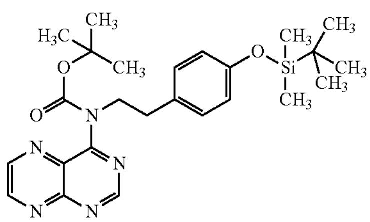 [SMILES: CC(C)(C)OC(=O)N(CCc1ccc(O[Si](C)(C)C(C)(C)C)cc1)c1ncnc2nccnc12] | | 133 | 13 |
| 135 | 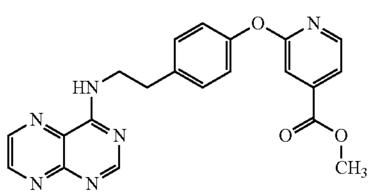 [SMILES: COC(=O)c1ccnc(Oc2ccc(CCNc3ncnc4nccnc34)cc2)c1] | 36 | methanol | 15 |
| 136 | 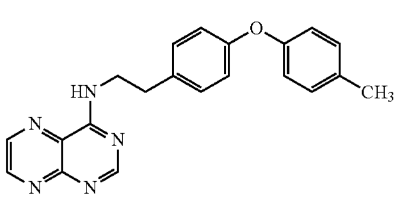 [SMILES: Cc1ccc(Oc2ccc(CCNc3ncnc4nccnc34)cc2)cc1] | Albert, A.; Ohta, K. *J. Chem. Soc. C* 1971, 3727-3730. | | 2 |
| 137 | 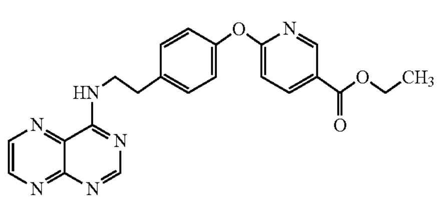 [SMILES: CCOC(=O)c1ccc(Oc2ccc(CCNc3ncnc4nccnc34)cc2)nc1] | | 4 | 3 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 138 | 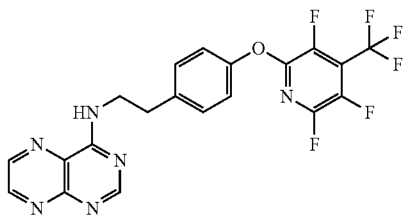 [SMILES: Fc1nc(Oc2ccc(CCNc3ncnc4nccnc34)cc2)c(F)c(C(F)(F)F)c1F] | | 4 | 16 |
| 139 | 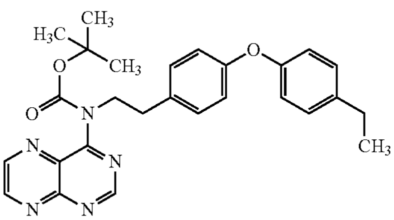 [SMILES: CCc1ccc(Oc2ccc(CCN(C(=O)OC(C)(C)C)c3ncnc4nccnc34)cc2)cc1] | 4-ethylphenylboronic acid | 217 | Example 11 |
| 140 | 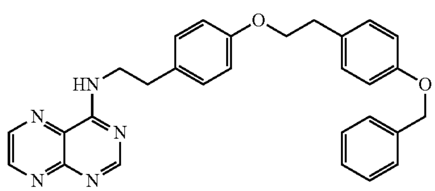 [SMILES: c1ccc(COc2ccc(CCOc3ccc(CCNc4ncnc5nccnc45)cc3)cc2)cc1] | | 4 | 17 |
| 141 | 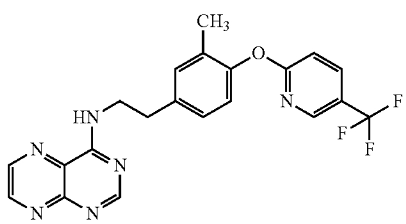 [SMILES: Cc1cc(CCNc2ncnc3nccnc23)ccc1Oc1ccc(C(F)(F)F)cn1] | | 174 | 4 |
| 142 | 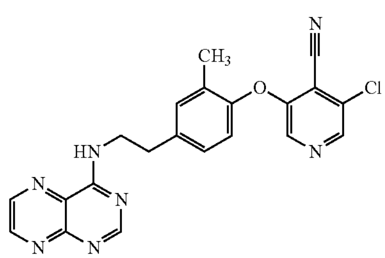 [SMILES: Cc1cc(CCNc2ncnc3nccnc23)ccc1Oc1cncc(Cl)c1C#N] | | 174 | 4 |
| 143 | 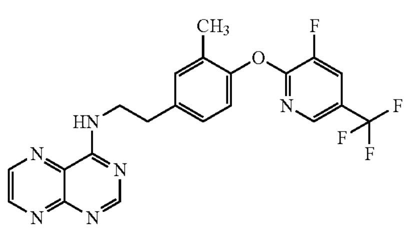 [SMILES: Cc1cc(CCNc2ncnc3nccnc23)ccc1Oc1ncc(C(F)(F)F)cc1F] | | 174 | 4 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 144 | 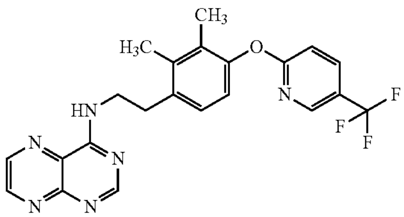 [SMILES: Cc1c(CCNc2ncnc3nccnc23)ccc(Oc2ccc(C(F)(F)F)cn2)c1C] | | 175 | 4 |
| 145 | 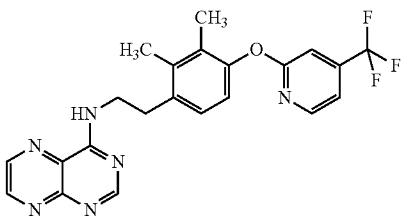 [SMILES: Cc1c(CCNc2ncnc3nccnc23)ccc(Oc2cc(C(F)(F)F)ccn2)c1C] | | 175 | 4 |
| 146 | 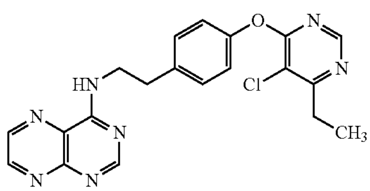 [SMILES: CCc1ncnc(Oc2ccc(CCNc3ncnc4nccnc34)cc2)c1Cl] | Mills, L.; Previdoli, F. EP 370391 A2, 1990. | 4 | 4 |
| 147 | 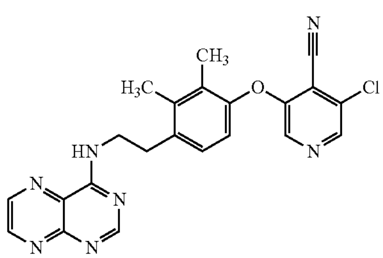 [SMILES: Cc1c(CCNc2ncnc3nccnc23)ccc(Oc2cncc(Cl)c2C#N)c1C] | | 175 | 4 |
| 148 | 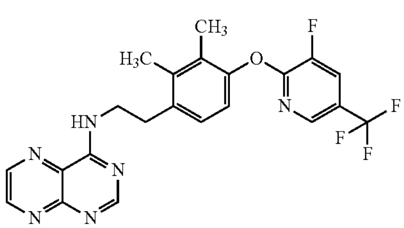 [SMILES: Cc1c(CCNc2ncnc3nccnc23)ccc(Oc2ncc(C(F)(F)F)cc2F)c1C] | | 175 | 4 |
| 149 | 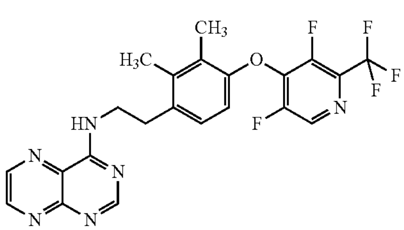 [SMILES: Cc1c(CCNc2ncnc3nccnc23)ccc(Oc2c(F)cnc(C(F)(F)F)c2F)c1C] | Scovell, E. G.; Watson, D. J. EP 63872 A1, 1982. | 175 | 4 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 150 | 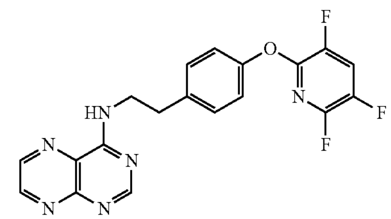 [SMILES: Fc1cc(F)c(Oc2ccc(CCNc3ncnc4nccnc34)cc2)nc1F] | | 4 | 4 |
| 151 | 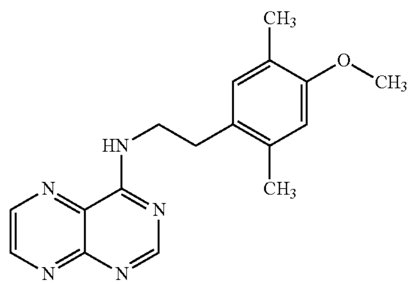 [SMILES: COc1cc(C)c(CCNc2ncnc3nccnc23)cc1C] | Albert, A.; Ohta, K. J. Chem. Soc. C 1971, 3727-3730. | As in Preparation 8, Step 2 | 2 |
| 152 | 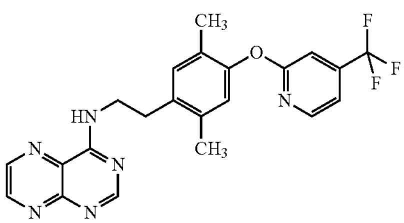 [SMILES: Cc1cc(Oc2cc(C(F)(F)F)ccn2)c(C)cc1CCNc1ncnc2nccnc12] | | 229 | 3 |
| 153 | 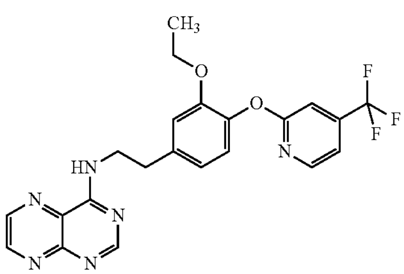 [SMILES: CCOc1cc(CCNc2ncnc3nccnc23)ccc1Oc1cc(C(F)(F)F)ccn1] | | 219 | 3 |
| 154 | 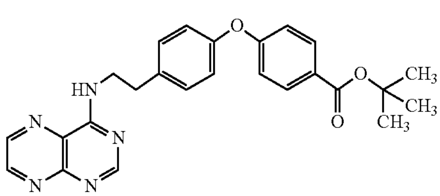 [SMILES: CC(C)(C)OC(=O)c1ccc(Oc2ccc(CCNc3ncnc4nccnc34)cc2)cc1] | | 4 | 4 |
| 155 | 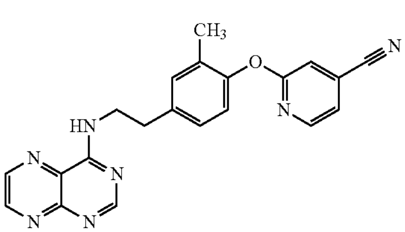 [SMILES: Cc1cc(CCNc2ncnc3nccnc23)ccc1Oc1cc(C#N)ccn1] | | 174 | 4 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 156 | 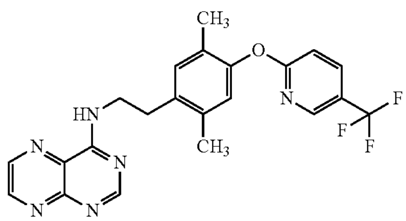 [SMILES: Cc1cc(Oc2ccc(C(F)(F)F)cn2)c(C)cc1CCNc1ncnc2nccnc12] | | 229 | 3 |
| 157 | 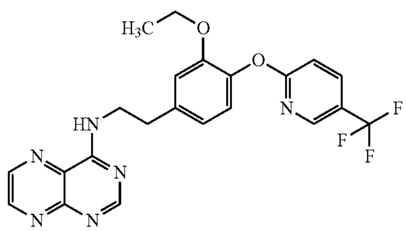 [SMILES: CCOc1cc(CCNc2ncnc3nccnc23)ccc1Oc1ccc(C(F)(F)F)cn1] | | 220 | 3 |
| 158 | 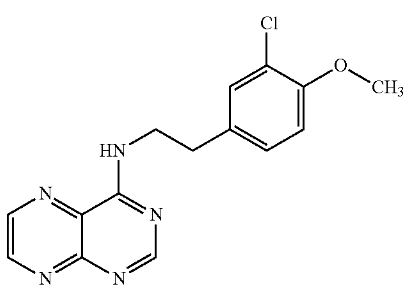 [SMILES: COc1ccc(CCNc2ncnc3nccnc23)cc1Cl] | Albert, A.; Ohta, K. *J. Chem. Soc. C* 1971, 3727-3730. | | 2 |
| 159 | 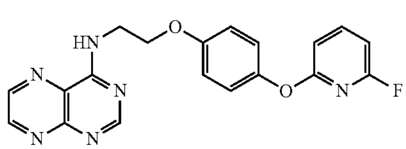 [SMILES: Fc1cccc(Oc2ccc(OCCNc3ncnc4nccnc34)cc2)n1] | | 80 | 4 |
| 160 | 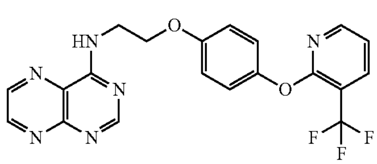 [SMILES: FC(F)(F)c1cccnc1Oc1ccc(OCCNc2ncnc3nccnc23)cc1] | | 80 | 4 |
| 161 | 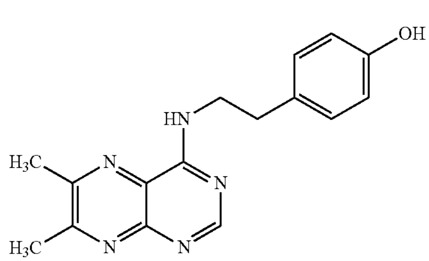 [SMILES: Cc1nc2ncnc(NCCc3ccc(O)cc3)c2nc1C] | | 131 | 18 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 162 | 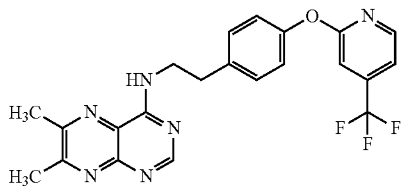 [SMILES: Cc1nc2ncnc(NCCc3ccc(Oc4cc(C(F)(F)F)ccn4)cc3)c2nc1C] | Knox, I. L.; Rogers, R. B. U.S. Pat. No. 4,775,762, 1988. | 161 | 3 |
| 163 | 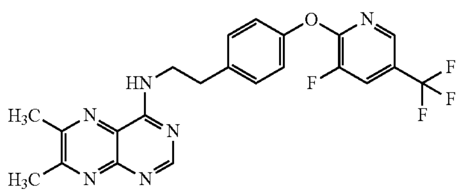 [SMILES: Cc1nc2ncnc(NCCc3ccc(Oc4ncc(C(F)(F)F)cc4F)cc3)c2nc1C] | | 161 | 3 |
| 164 | 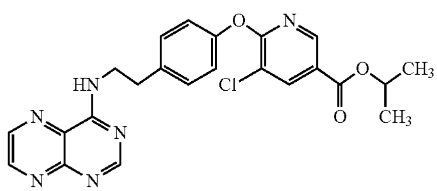 [SMILES: CC(C)OC(=O)c1cnc(Oc2ccc(CCNc3ncnc4nccnc34)cc2)c(Cl)c1] | | 4 | 3 |
| 165 | 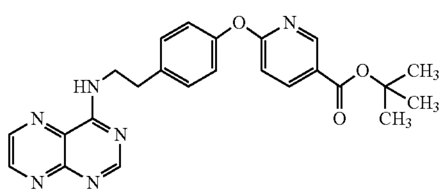 [SMILES: CC(C)(C)OC(=O)c1ccc(Oc2ccc(CCNc3ncnc4nccnc34)cc2)nc1] | | 4 | 3 |
| 166 | 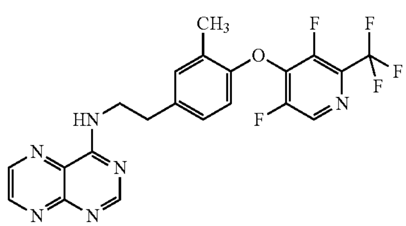 [SMILES: Cc1cc(CCNc2ncnc3nccnc23)ccc1Oc1c(F)cnc(C(F)(F)F)c1F] | Scovell, E. G.; Watson, D. J. EP 63872 A1, 1982. | 174 | 3 |
| 167 | 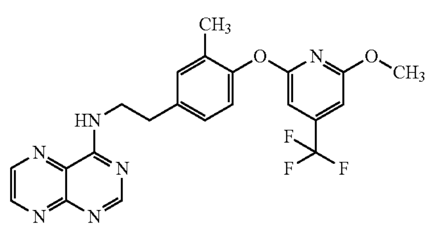 [SMILES: COc1cc(C(F)(F)F)cc(Oc2ccc(CCNc3ncnc4nccnc34)cc2C)n1] | Preparation 11 | 174 | 3 |
| 168 | 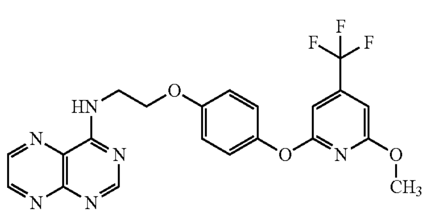 [SMILES: COc1cc(C(F)(F)F)cc(Oc2ccc(OCCNc3ncnc4nccnc34)cc2)n1] | Preparation 11 | 80 | 3 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 169 | 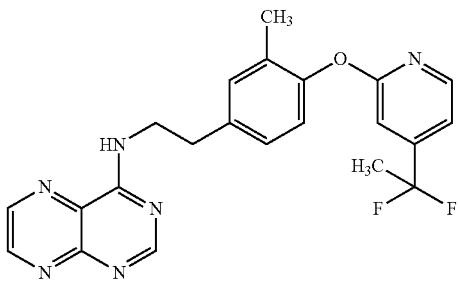 [SMILES: Cc1cc(CCNc2ncnc3nccnc23)ccc1Oc1cc(C(C)(F)F)ccn1] | Preparation 4 | 174 | 3 |
| 170 | 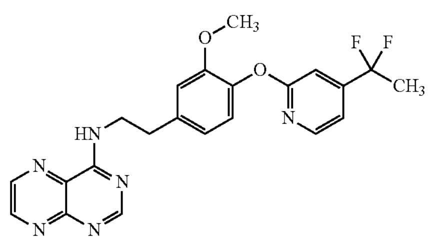 [SMILES: COc1cc(CCNc2ncnc3nccnc23)ccc1Oc1cc(C(C)(F)F)ccn1] | Preparation 4 | 37 | 3 |
| 171 | 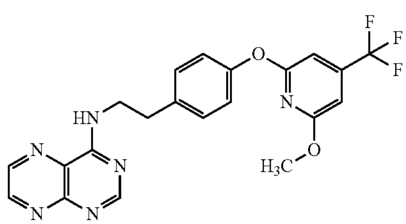 [SMILES: COc1cc(C(F)(F)F)cc(Oc2ccc(CCNc3ncnc4nccnc34)cc2)n1] | Preparation 11 | 4 | 3 |
| 172 | 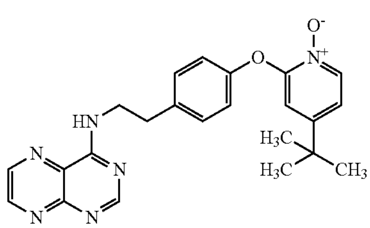 [SMILES: CC(C)(C)c1cc[n+]([O-])c(Oc2ccc(CCNc3ncnc4nccnc34)cc2)c1] | Preparation 12 | 4 | 3 |
| 173 | 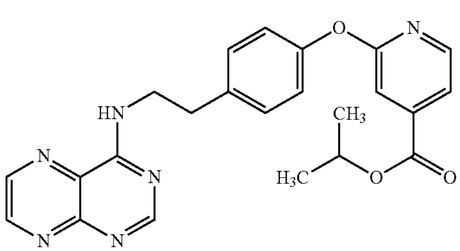 [SMILES: CC(C)OC(=O)c1ccnc(Oc2ccc(CCNc3ncnc4nccnc34)cc2)c1] | 36 | 2-propanol | 15 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 174 | 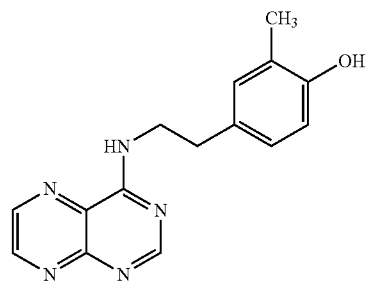 [SMILES: Cc1cc(CCNc2ncnc3nccnc23)ccc1O] | 221 | | 18 |
| 175 | 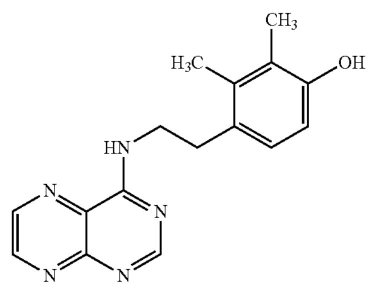 [SMILES: Cc1c(O)ccc(CCNc2ncnc3nccnc23)c1C] | 228 | | 18 |
| 176 | 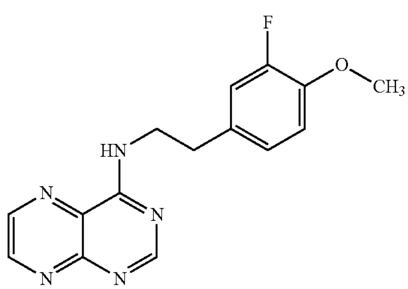 [SMILES: COc1ccc(CCNc2ncnc3nccnc23)cc1F] | Albert, A.; Ohta, K. *J. Chem. Soc. C* 1971, 3727-3730. | As in Preparation 9, Step 5 | 2 |
| 177 | 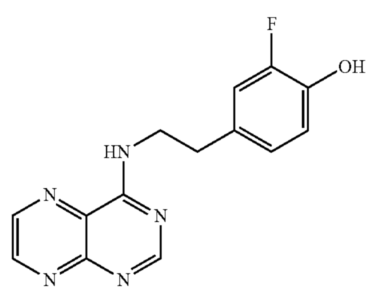 [SMILES: Oc1ccc(CCNc2ncnc3nccnc23)cc1F] | 176 | | 18 |
| 178 | 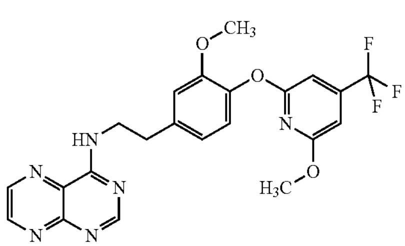 [SMILES: COc1cc(C(F)(F)F)cc(Oc2ccc(CCNc3ncnc4nccnc34)cc2OC)n1] | Preparation 11 | 37 | 3 |

US 8,895,568 B2

123                                    124

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 179 | 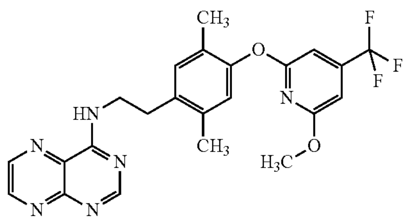 [SMILES: COc1cc(C(F)(F)F)cc(Oc2cc(C)c(CCNc3ncnc4nccnc34)cc2C)n1] | Preparation 11 | 229 | 3 |
| 180 | 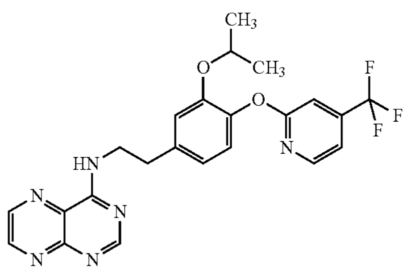 [SMILES: CC(C)Oc1cc(CCNc2ncnc3nccnc23)ccc1Oc1cc(C(F)(F)F)ccn1] | 2-bromopropane | 218 | 19 |
| 181 | 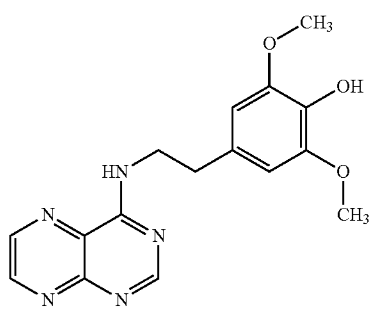 [SMILES: COc1cc(CCNc2ncnc3nccnc23)cc(OC)c1O] | Albert, A.; Ohta, K. *J. Chem. Soc. C* 1971, 3727-3730. | | 2 |
| 182 | 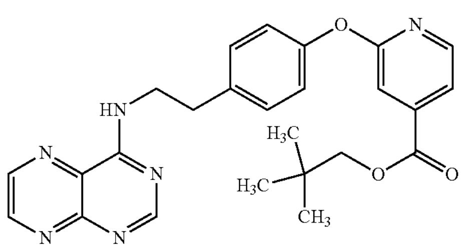 [SMILES: CC(C)(C)COC(=O)c1ccnc(Oc2ccc(CCNc3ncnc4nccnc34)cc2)c1] | Preparation 13 | 4 | 4 |
| 183 | 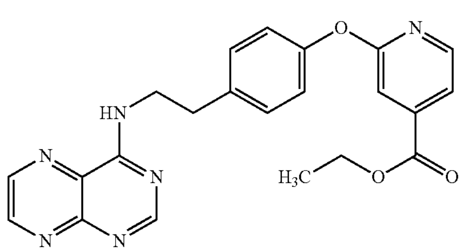 [SMILES: CCOC(=O)c1ccnc(Oc2ccc(CCNc3ncnc4nccnc34)cc2)c1] | | 4 | 4 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 184 | 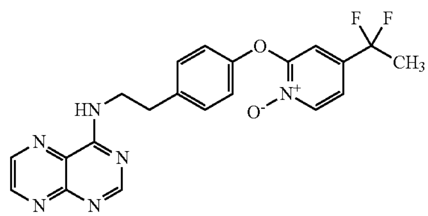 [SMILES: CC(F)(F)c1cc[n+]([O-])c(Oc2ccc(CCNc3ncnc4nccnc34)cc2)c1] | Preparation 14 | 4 | 4 |
| 185 | 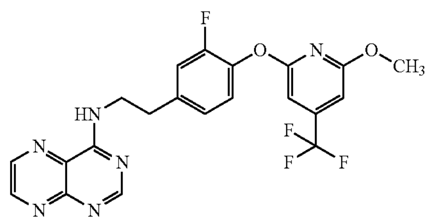 [SMILES: COc1cc(C(F)(F)F)cc(Oc2ccc(CCNc3ncnc4nccnc34)cc2F)n1] | Preparation 11 | 177 | 4 |
| 186 | 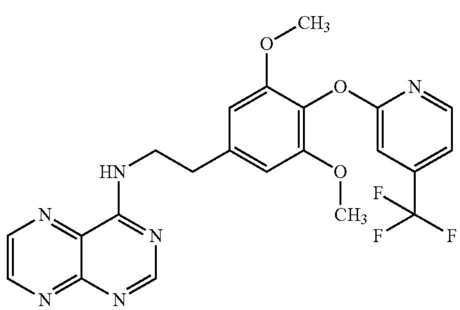 [SMILES: COc1cc(CCNc2ncnc3nccnc23)cc(OC)c1Oc1cc(C(F)(F)F)ccn1] | | 181 | 4 |
| 187 | 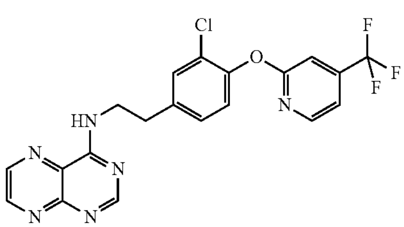 [SMILES: FC(F)(F)c1ccnc(Oc2ccc(CCNc3ncnc4nccnc34)cc2Cl)c1] | | 230 | 3 |
| 188 | 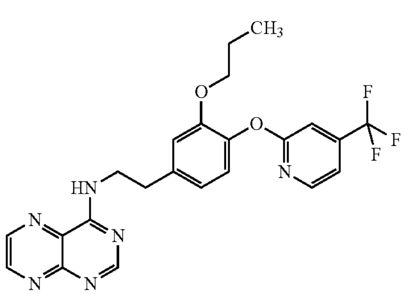 [SMILES: CCCOc1cc(CCNc2ncnc3nccnc23)ccc1Oc1cc(C(F)(F)F)ccn1] | 1-bromopropane | 218 | 19 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 189 | *structure* | *structure* Preparation 4 | 219 | 4 |
| 190 | *structure* | acetic anhydride | 218 | 20 |
| 191 | *structure* | | 184 | 21 |
| 192 | *structure* | *structure* from tert-butanol, as in Preparation 13 | 4 | 4 |
| 193 | *structure* | *structure* Preparation 4 | 177 | 4 |
| 194 | *structure* | *structure* Preparation 15 | 229 | 4 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 195 | 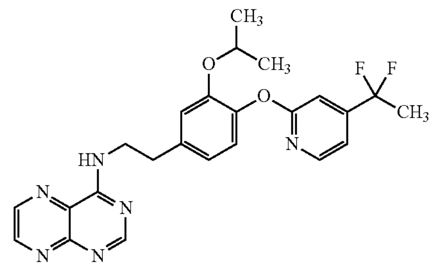 [SMILES: CC(C)Oc1cc(CCNc2ncnc3nccnc23)ccc1Oc1cc(C(C)(F)F)ccn1] | | 197 | 19 |
| 196 | 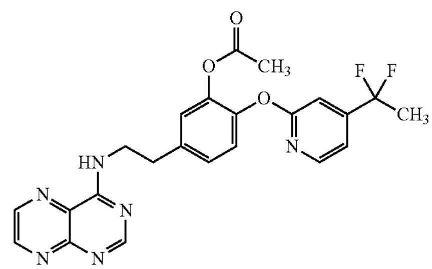 [SMILES: CC(=O)Oc1cc(CCNc2ncnc3nccnc23)ccc1Oc1cc(C(C)(F)F)ccn1] | | 197 | 20 |
| 197 | 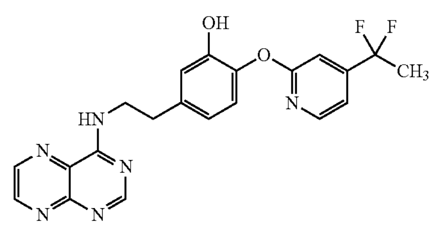 [SMILES: CC(F)(F)c1ccnc(Oc2ccc(CCNc3ncnc4nccnc34)cc2O)c1] | 170 | | 18 |
| 198 | 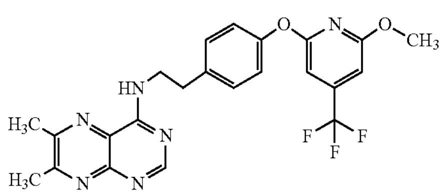 | Preparation 11 | 161 | 3 |
| 199 | 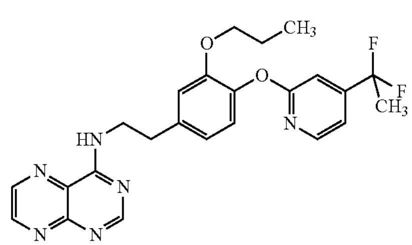 [SMILES: CCCOc1cc(CCNc2ncnc3nccnc23)ccc1Oc1cc(C(C)(F)F)ccn1] | 1-bromopropane | 197 | 19 |
| 200 | 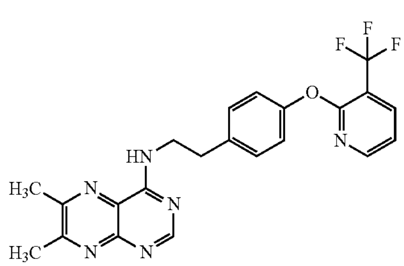 [SMILES: Cc1nc2ncnc(NCCc3ccc(Oc4ncccc4C(F)(F)F)cc3)c2nc1C] | | 161 | 3 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 201 | 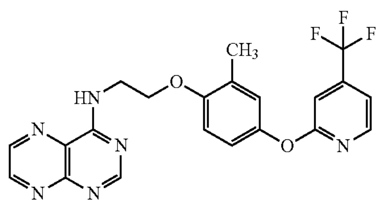 [SMILES: Cc1cc(Oc2cc(C(F)(F)F)ccn2)ccc1OCCNc1ncnc2nccnc12] | Knox, I. L.; Rogers, R. B. U.S. Pat. No. 4,775,762, 1988 | 225 | 4 |
| 202 | 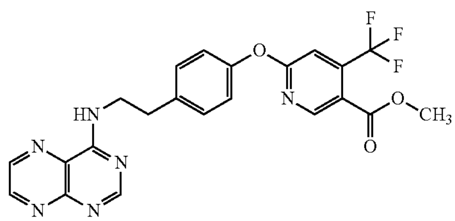 [SMILES: COC(=O)c1cnc(Oc2ccc(CCNc3ncnc4nccnc34)cc2)cc1C(F)(F)F] | | 4 | 4 |
| 203 | 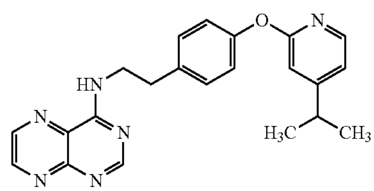 [SMILES: CC(C)c1ccnc(Oc2ccc(CCNc3ncnc4nccnc34)cc2)c1] | | 4 | 4 |
| 204 | 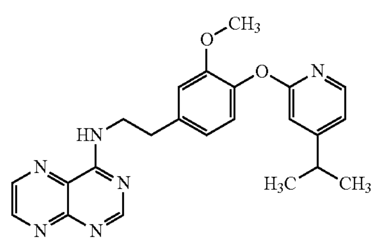 [SMILES: COc1cc(CCNc2ncnc3nccnc23)ccc1Oc1cc(C(C)C)ccn1] | | 37 | 4 |
| 205 | 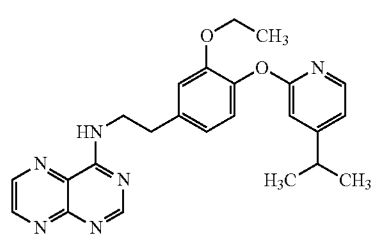 [SMILES: CCOc1cc(CCNc2ncnc3nccnc23)ccc1Oc1cc(C(C)C)ccn1] | | 219 | 4 |
| 206 | 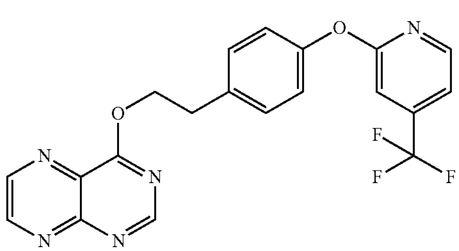 [SMILES: FC(F)(F)c1ccnc(Oc2ccc(CCOc3ncnc4nccnc34)cc2)c1] | Knox, I. L.; Rogers, R. B. U.S. Pat. No. 4,775,762, 1988. | | 22 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 207 | 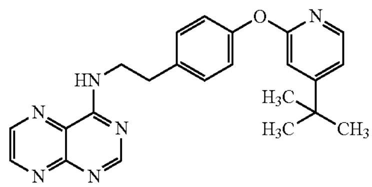 [SMILES: CC(C)(C)c1ccnc(Oc2ccc(CCNc3ncnc4nccnc34)cc2)c1] | | 172 | 23 |
| 208 | 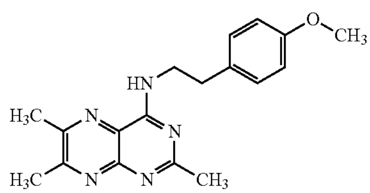 | | | 24 |
| 209 | 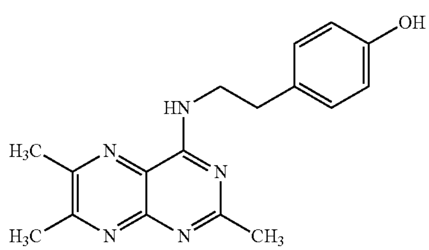 [SMILES: Cc1nc(NCCc2ccc(O)cc2)c2nc(C)c(C)nc2n1] | | 208 | 18 |
| 210 | 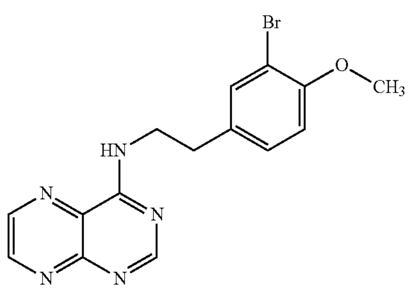 | Albert, A.; Ohta, K. *J. Chem. Soc. C* 1971, 3727-3730. | | 2 |
| 211 | 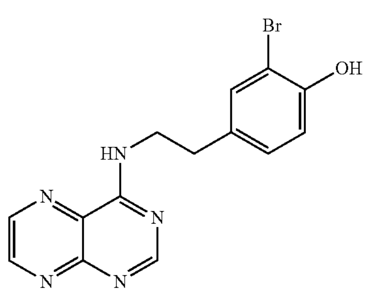 | | 210 | 18 |
| 212 | 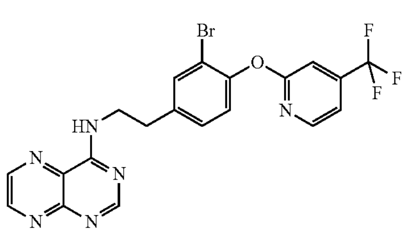 [SMILES: FC(F)(F)c1ccnc(Oc2ccc(CCNc3ncnc4nccnc34)cc2Br)c1] | Knox, I. L.; Rogers, R. B. U.S. Pat. No. 4,775,762, 1988. | 211 | 3 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 213 | 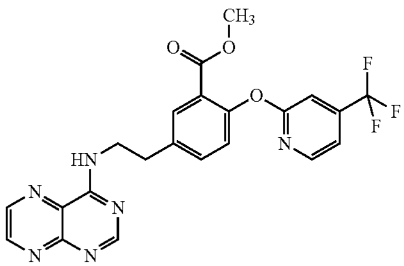 [SMILES: COC(=O)c1cc(CCNc2ncnc3nccnc23)ccc1Oc1cc(C(F)(F)F)ccn1] | 212 | methanol | 15 |
| 214 | 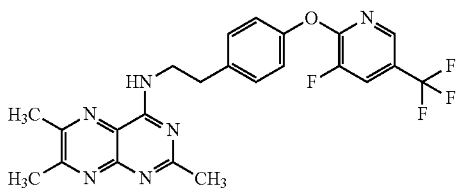 [SMILES: Cc1nc(NCCc2ccc(Oc3ncc(C(F)(F)F)cc3F)cc2)c2nc(C)c(C)nc2n1] | | 209 | 3 |
| 215 | 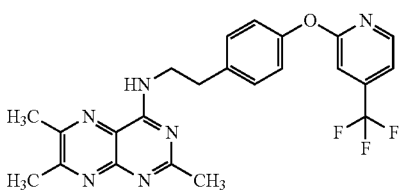 [SMILES: Cc1nc(NCCc2ccc(Oc3cc(C(F)(F)F)ccn3)cc2)c2nc(C)c(C)nc2n1] | Knox, I. L.; Rogers, R. B. U.S. Pat. No. 4,775,762, 1988. | 209 | 3 |
| 216 | 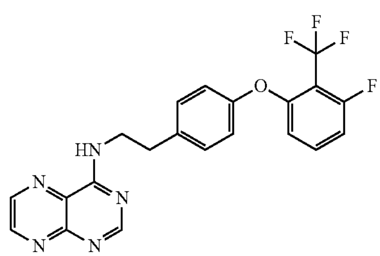 [SMILES: Fc1cccc(Oc2ccc(CCNc3ncnc4nccnc34)cc2)c1C(F)(F)F] | | 4 | 4 |
| 217 | 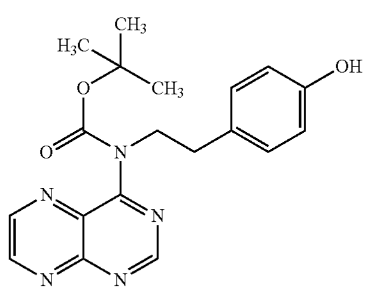 [SMILES: CC(C)(C)OC(=O)N(CCc1ccc(O)cc1)c1ncnc2nccnc12] | | 134 | 14 |
| 218 | 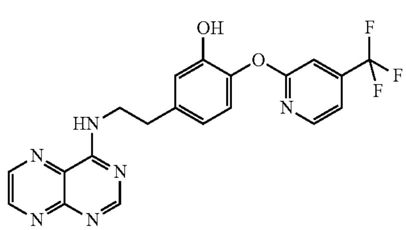 | 51 | | 18 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 219 | (pteridinyl-NH-CH₂CH₂-phenyl with 3-ethoxy, 4-OH) | 3-ethynylpyrazine with N=CH-N(CH₃)₂; Albert, A.; Ohta, K. *J. Chem. Soc. C* 1971, 3727-3730. | H₂N-CH₂CH₂-phenyl with 3-ethoxy, 4-OH | 2 |
| 220 | (pteridinyl-NH-CH₂CH₂-phenyl with 3-F, 4-OH) | 62 | | 18 |
| 221 | (pteridinyl-NH-CH₂CH₂-phenyl with 3-methyl, 4-OMe) | 3-ethynylpyrazine with N=CH-N(CH₃)₂; Albert, A.; Ohta, K. *J. Chem. Soc. C* 1971, 3727-3730. | H₂N-CH₂CH₂-phenyl with 3-methyl, 4-OMe; As in Preparation 9, Step 5 | 2 |
| 222 | (pteridinyl-NH-CH₂CH₂-phenyl with 4-Br) | 3-ethynylpyrazine with N=CH-N(CH₃)₂; Albert, A.; Ohta, K. *J. Chem. Soc. C* 1971, 3727-3730. | H₂N-CH₂CH₂-phenyl with 4-Br | 2 |
| 223 | (pteridinyl-NH-CH₂CH₂-phenyl with 2-methyl, 4-OMe) | 3-ethynylpyrazine with N=CH-N(CH₃)₂; Albert, A.; Ohta, K. *J. Chem. Soc. C* 1971, 3727-3730. | H₂N-CH₂CH₂-phenyl with 2-methyl, 4-OMe; As in Preparation 8, Step 2 | 2 |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 224 | 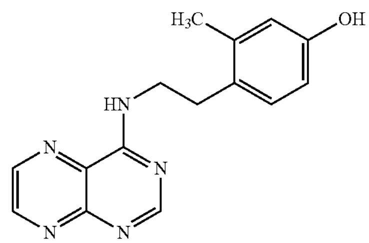 [SMILES: Cc1cc(O)ccc1CCNc1ncnc2nccnc12] | 223 | | 18 |
| 225 | 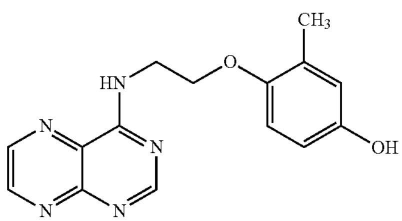 [SMILES: Cc1cc(O)ccc1OCCNc1ncnc2nccnc12] | | | 2 |
| | | Albert, A.; Ohta, K. *J. Chem. Soc. C* 1971, 3727-3730. | Preparation 16 | |
| 226 | 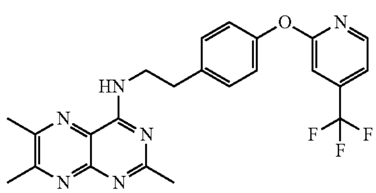 [SMILES: Cc1nc(NCCc2ccc(Oc3cc(C(F)(F)F)ccn3)cc2)c2nc(C)c(C)nc2n1] | | 209 | 3 |
| 227 | 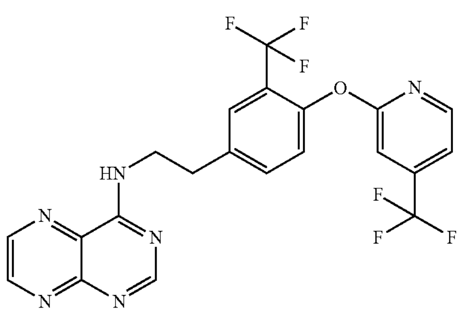 [SMILES: FC(F)(F)c1ccnc(Oc2ccc(CCNc3ncnc4nccnc34)cc2C(F)(F)F)c1] | | | 4[3] |
| 228 | 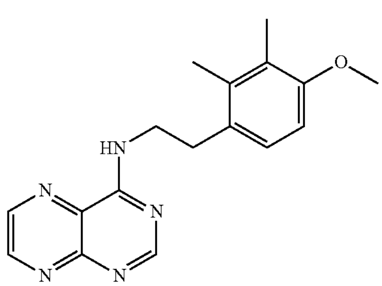 [SMILES: COc1ccc(CCNc2ncnc3nccnc23)c(C)c1C] | | | 2 |
| | | Albert, A.; Ohta, K. *J. Chem. Soc. C* 1971, 3727-3730. | As in Preparation 8, Step 2 | |

TABLE 1-continued

Examples of compounds of formula (I-A) and (I-B) including synthesis parameters.[1,2]

| ID | Structure | Electrophile or Other Reactant (Cmpd Name, Structure or Number) | Amine or Other Reactant (Cmpd Name, Structure or Number) | Preparative Methods (Example Numbers) |
|---|---|---|---|---|
| 229 | 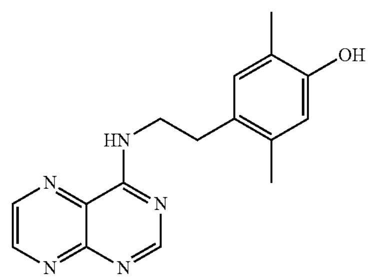 [SMILES: Cc1cc(CCNc2ncnc3nccnc23)c(C)cc1O] | 151 | | 18 |
| 230 | 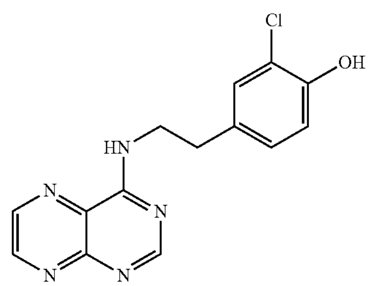 | 158 | | 18 |
| 231 | 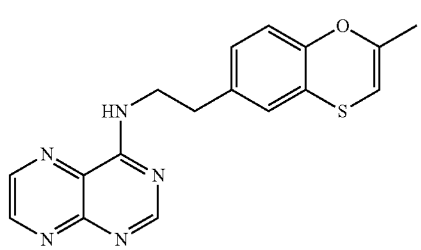 [SMILES: CC1=CSc2cc(CCNc3ncnc4nccnc34)ccc2O1] | | | 4 (by-product from preparation of Compound 59) |
| 232 | 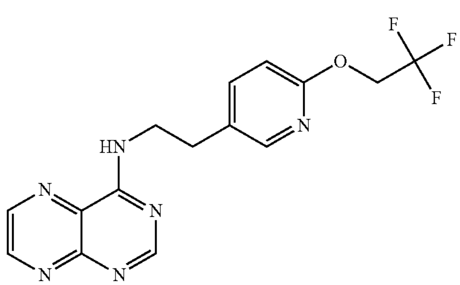 [SMILES: FC(F)(F)COc1ccc(CCNc2ncnc3nccnc23)cn1] | | Dreikorn, B. A. et al., WO 9404527 A1, 1994. | 1 |

Footnotes to Table 1.

[1] All literature references to compounds used in the Preparations and Examples listed in Table 1 are expressly incorporated by reference herein.

[2] All compounds used for chemical synthesis which are depicted in Table 1 and are listed with no specified literature reference or Preparation were purchased from commercial sources.

[3] The synthesis of compound 227 began with transformation of (4-methoxy-3-trifluoromethylphenyl)-methanol to 2-(4-methoxy-3-trifluoromethyl-phenyl)-ethylamine hydrochloride, in the same manner as described in Preparation 9, Steps 4 and 5. 2-(4-Methoxy-3-trifluoromethyl-phenyl)-ethylamine hydrochloride then was sequentially elaborated by the similar chemical transformations as in Examples 2, 18 and 4 (the other reactant was 2-chloro-4-trifluoromethylpyridine) to provide Compound 227.

Biological Testing

The following Table 2 shows characterizing mass spectrometry and biological activity of representative compounds of formula (I-A) and (I-B).

TABLE 2

Examples of compounds of formula (I-A) and (I-B) including mass spectrometry data and biological activity against representative fungal diseases and insects.

| ID | MS [M + H]+ | COCHSA | COLLLA | LEPTNO | PSPECU | PUCCRT | PYRIOR | >80% mortality on any insect species @ 4000 ppm |
|---|---|---|---|---|---|---|---|---|
| 1 | 358 | ** | *** | *** | *** | *** | *** | − |
| 2 | 413 | ** | *** | *** | *** | *** | *** | + |
| 3 | 414 | * | ** | ** | *** | *** | *** | − |
| 4 | 268 | * | * | * | * | * | ** | − |
| 5 | 413 | * | *** | *** | *** | *** | *** | + |
| 6 | 413 | * | * | *** | *** | *** | *** | + |
| 7 | 363 | * | * | * | *** | *** | *** | + |
| 8 | 370 | * | *** | * | *** | *** | *** | + |
| 9 | 252 | * | * | * | *** | *** | *** | − |
| 10 | 375 | * | * | ** | *** | *** | *** | + |
| 11 | 443 | * | * | ** | ** | *** | *** | + |
| 12 | 389 | * | * | *** | *** | *** | *** | + |
| 13 | 370 | * | * | * | *** | *** | *** | + |
| 14 | 370 | * | * | * | *** | *** | ** | + |
| 15 | 346 | * | * | * | *** | *** | *** | + |
| 16 | 376 | * | * | * | *** | *** | *** | − |
| 17 | 282 | * | ** | ** | *** | *** | *** | − |
| 18 | 371 | * | * | * | *** | *** | *** | − |
| 19 | 296 | * | * | * | * | * | *** | − |
| 20 | 268 | * | * | * | * | * | ** | − |
| 21 | 382 | * | ** | ** | ** | *** | *** | − |
| 22 | 428 | * | ** | ** | ** | *** | *** | − |
| 23 | 429 | * | * | * | * | *** | ** | − |
| 24 | 380 | * | ** | * | *** | *** | *** | − |
| 25 | 444 | * | * | *** | *** | *** | *** | + |
| 26 | 408 | * | * | * | *** | *** | *** | − |
| 27 | 458 | * | * | * | * | *** | *** | − |
| 28 | 346 | * | * | * | *** | *** | *** | + |
| 29 | 362 | * | * | * | *** | ** | ** | − |
| 30 | 413 | * | * | *** | ** | *** | *** | + |
| 31 | 385 | NT | NT | * a | NT | ** b | *** b | NT |
| 32 | 470 | NT | NT | * a | NT | ** b | ** b | NT |
| 33 | 430 | * | * | ** | * | *** | ** | − |
| 34 | 414 | * | * | ** | *** | *** | *** | + |
| 35 | 404 | * | * | * | *** | *** | *** | − |
| 36 | 471 | ** | ** | ** | *** | *** | *** | + |
| 37 | —¹ | * | * | * | * | *** | ** | − |
| 38 | 282 | * | * | * | * | * | ** | − |
| 39 | 359 | * | * | *** | *** | *** | *** | + |
| 40 | 359 | * | ** | *** | *** | *** | *** | + |
| 41 | 427 | * | ** | *** | *** | *** | *** | + |
| 42 | 359 | * | *** | *** | *** | *** | *** | + |
| 43 | 359 | * | * | *** | *** | *** | *** | + |
| 44 | 409 | * | ** | *** | *** | *** | *** | + |
| 45 | 282 | NT | NT | * a | NT | ** b | *** b | NT |
| 46 | 413 | * | *** | *** | *** | *** | *** | − |
| 47 | 413 | * | ** | *** | *** | *** | *** | − |
| 48 | 351 | * | * | * | *** | *** | *** | + |
| 49 | 443 | ** | ** | ** | *** | *** | *** | + |
| 50 | 400 | * | * | * | *** | *** | *** | + |
| 51 | 443 | * | ** | ** | *** | *** | *** | + |
| 52 | 384 | * | * | *** | *** | *** | *** | + |
| 53 | 445 | * | *** | *** | *** | *** | *** | + |
| 54 | 431 | * | *** | *** | *** | *** | *** | + |
| 55 | 428 | * | ** | *** | *** | *** | *** | + |
| 56 | 447 | * | * | ** | ** | *** | * | − |
| 57 | —² | * | * | * | *** | *** | *** | − |
| 58 | 427 | * | * | ** | ** | *** | *** | + |
| 59 | 366 | * | * | * | * | *** | ** | + |
| 60 | 413 | * | ** | *** | *** | *** | *** | + |
| 61 | 403 | * | * | ** | *** | *** | *** | − |
| 62 | —³ | * | * | ** | *** | *** | *** | − |
| 63 | 416 | * | * | * | *** | *** | *** | − |
| 64 | 413 | * | * | * | *** | *** | *** | − |

TABLE 2-continued

Examples of compounds of formula (I-A) and (I-B) including mass spectrometry data and biological activity against representative fungal diseases and insects.

| ID | MS [M + H]+ | COCHSA | COLLLA | LEPTNO | PSPECU | PUCCRT | PYRIOR | >80% mortality on any insect species @ 4000 ppm |
|---|---|---|---|---|---|---|---|---|
| 65 | 268 | * | * | ** | ** | ** | * | − |
| 66 | 365 | ** | *** | ** | *** | *** | *** | + |
| 67 | 413 | * | * | *** | *** | *** | *** | + |
| 68 | 414 | * | * | * | *** | *** | *** | + |
| 69 | 427 | * | *** | ** | *** | *** | *** | − |
| 70 | 404 | NT | NT | * a | NT | ** b | ** b | − |
| 71 | 449 | * | * | ** | * | *** | *** | − |
| 72 | 449 | * | ** | ** | *** | *** | *** | − |
| 73 | 302 | * | * | * | * | *** | ** | − |
| 74 | 471 | * | * | ** | *** | *** | *** | − |
| 75 | 448 | * | * | ** | * | *** | *** | + |
| 76 | 427 | * | * | ** | *** | *** | *** | + |
| 77 | 413 | * | * | *** | *** | *** | *** | − |
| 78 | 294 | * | * | ** | * | ** | * | − |
| 79 | 337 | * | * | * | * | ** | * | + |
| 80 | 284 | * | * | * | * | * | * | − |
| 81 | 284 | * | * | * | *** | * | * | − |
| 82 | 413 | * | * | ** | *** | *** | *** | + |
| 83 | 429 | * | *** | *** | *** | *** | *** | − |
| 84 | 429 | * | *** | *** | *** | *** | *** | + |
| 85 | 386 | * | * | * | *** | *** | *** | − |
| 86 | 429 | * | * | * | *** | *** | *** | − |
| 87 | 429 | * | * | ** | *** | *** | *** | − |
| 88 | 386 | * | * | ** | *** | *** | ** | − |
| 89 | 467 | * | * | ** | *** | *** | *** | − |
| 90 | 447 | * | * | *** | *** | *** | *** | + |
| 91 | 487 | * | * | ** | *** | *** | *** | + |
| 92 | 447 | * | * | ** | *** | *** | *** | + |
| 93 | 431 | ** | *** | *** | *** | *** | *** | + |
| 94 | 417 | * | ** | ** | ** | *** | *** | − |
| 95 | 375 | * | *** | *** | *** | *** | *** | + |
| 96 | 443 | * | * | *** | *** | *** | *** | + |
| 97 | 444 | * | * | ** | *** | *** | *** | + |
| 98 | 393 | NT | NT | * a | NT | ** b | ** b | NT |
| 99 | 377 | NT | NT | ** a | NT | *** b | *** b | NT |
| 100 | 440 | * | * | ** | *** | *** | *** | − |
| 101 | 395 | * | *** | *** | *** | *** | *** | + |
| 102 | 407 | * | * | * | *** | *** | *** | − |
| 103 | 431 | * | * | *** | *** | *** | *** | + |
| 104 | 389 | * | * | *** | *** | *** | *** | + |
| 105 | 431 | NT | NT | *** a | NT | *** b | *** b | NT |
| 106 | 449 | * | * | ** | *** | *** | *** | + |
| 107 | 381 | * | * | ** | *** | *** | *** | + |
| 108 | 381 | * | * | ** | *** | *** | *** | + |
| 109 | 427 | * | ** | ** | *** | *** | *** | + |
| 110 | 423 | * | * | *** | *** | *** | *** | + |
| 111 | 413 | * | ** | *** | *** | *** | *** | + |
| 112 | 484 | * | * | *** | *** | *** | *** | + |
| 113 | 430 | * | * | *** | *** | *** | *** | + |
| 114 | 449 | * | * | *** | *** | *** | *** | + |
| 115 | 481 | * | * | * | *** | *** | *** | − |
| 116 | 308 | NT | NT | * a | NT | * b | ** b | + |
| 117 | 483 | NT | NT | ** a | NT | ** b | *** b | + |
| 118 | 465 | * | * | ** | * | *** | ** | + |
| 119 | 439 | * | * | ** | * | ** | ** | − |
| 120 | 418 | * | * | ** | * | *** | ** | + |
| 121 | 347 | * | * | *** | *** | *** | *** | NT |
| 122 | 396 | * | * | ** | ** | *** | *** | + |
| 123 | 409 | NT | NT | NT | NT | NT | NT | NT |
| 124 | 447 | * | * | *** | *** | *** | ** | NT |
| 125 | 328 | * | * | *** | *** | *** | *** | + |
| 126 | 413 | * | *** | *** | *** | *** | *** | + |
| 127 | 420 | * | * | ** | ** | *** | *** | − |
| 128 | 453 | * | * | ** | *** | *** | *** | + |
| 129 | 427 | ** | ** | *** | *** | *** | *** | + |
| 130 | 461 | * | * | ** | *** | *** | *** | + |
| 131 | 310 | * | * | * | *** | *** | *** | + |
| 132 | 386 | * | * | ** | *** | *** | * | + |
| 133 | 382 | * | * | * | *** | *** | * | − |
| 134 | 482 | * | * | * | * | *** | * | − |

TABLE 2-continued

Examples of compounds of formula (I-A) and (I-B) including mass spectrometry data and biological activity against representative fungal diseases and insects.

| ID | MS [M + H]+ | COCHSA | COLLLA | LEPTNO | PSPECU | PUCCRT | PYRIOR | >80% mortality on any insect species @ 4000 ppm |
|---|---|---|---|---|---|---|---|---|
| 135 | 403 | * | * | ** | *** | *** | ** | − |
| 136 | 358 | * | ** | ** | *** | *** | *** | + |
| 137 | 417 | * | * | ** | * | *** | *** | + |
| 138 | 467 | * | *** | ** | *** | *** | *** | + |
| 139 | 472 | * | * | * | * | *** | * | − |
| 140 | 478 | * | ** | * | *** | *** | *** | + |
| 141 | 427 | * | ** | *** | *** | *** | *** | + |
| 142 | 418 | * | * | ** | *** | *** | *** | + |
| 143 | 445 | * | * | *** | *** | *** | *** | + |
| 144 | 441 | * | * | *** | *** | *** | *** | + |
| 145 | 441 | * | ** | *** | *** | *** | *** | + |
| 146 | 408 | * | ** | ** | *** | *** | *** | + |
| 147 | 432 | * | * | ** | *** | *** | *** | − |
| 148 | 459 | * | * | ** | *** | *** | *** | + |
| 149 | 477 | * | * | ** | *** | *** | *** | − |
| 150 | 399 | * | * | *** | *** | *** | *** | + |
| 151 | 310 | * | * | * | *** | *** | *** | − |
| 152 | 441 | * | * | *** | *** | *** | *** | + |
| 153 | 457 | * | * | *** | *** | *** | *** | + |
| 154 | 444 | NT | NT | *** a | NT | *** b | *** b | NT |
| 155 | 384 | * | ** | ** | *** | *** | *** | + |
| 156 | 441 | * | * | *** | *** | *** | *** | + |
| 157 | 457 | * | * | ** | *** | *** | *** | + |
| 158 | 316 | * | * | ** | * | *** | *** | − |
| 159 | 379 | * | * | * | *** | *** | *** | − |
| 160 | 429 | * | * | ** | *** | *** | *** | − |
| 161 | 296 | * | * | * | * | ** | ** | − |
| 162 | 441 | * | * | *** | *** | *** | *** | + |
| 163 | 459 | * | *** | *** | *** | *** | *** | + |
| 164 | 465 | * | * | ** | * | *** | *** | + |
| 165 | 445 | * | * | *** | *** | *** | *** | + |
| 166 | 463 | * | ** | *** | *** | *** | *** | + |
| 167 | 457 | * | * | ** | *** | *** | *** | − |
| 168 | 459 | * | * | ** | * | *** | *** | − |
| 169 | 423 | * | ** | *** | *** | *** | *** | + |
| 170 | 439 | * | * | ** | *** | *** | *** | + |
| 171 | 443 | * | * | ** | *** | *** | *** | − |
| 172 | 417 | * | * | * | *** | *** | *** | − |
| 173 | 431 | * | * | * | *** | *** | *** | − |
| 174 | 282 | * | * | ** | * | ** | *** | − |
| 175 | 296 | * | * | * | * | *** | *** | − |
| 176 | 300 | * | * | * | * | *** | *** | − |
| 177 | 286 | * | * | * | * | * | ** | − |
| 178 | 473 | * | * | ** | * | *** | *** | − |
| 179 | —4 | * | * | * | * | *** | ** | − |
| 180 | —5 | * | ** | ** | *** | *** | *** | − |
| 181 | 328 | * | * | * | * | ** | *** | − |
| 182 | 459 | * | * | * | *** | *** | * | − |
| 183 | 417 | * | * | ** | *** | *** | *** | − |
| 184 | 425 | * | ** | ** | *** | *** | *** | − |
| 185 | 461 | * | * | ** | *** | *** | *** | − |
| 186 | 473 | * | * | ** | *** | *** | *** | − |
| 187 | —6 | * | *** | *** | *** | *** | *** | + |
| 188 | —7 | * | *** | * | *** | *** | *** | + |
| 189 | 451 | * | ** | ** | *** | *** | *** | − |
| 190 | 471 | * | * | * | * | *** | *** | + |
| 191 | 439 | * | ** | ** | *** | *** | *** | − |
| 192 | 445 | * | *** | ** | *** | *** | *** | + |
| 193 | 427 | * | * | ** | *** | *** | *** | − |
| 194 | 437 | * | *** | ** | *** | *** | *** | + |
| 195 | 467 | * | ** | * | *** | *** | *** | − |
| 196 | 467 | * | * | * | *** | *** | ** | − |
| 197 | 425 | * | * | * | *** | *** | *** | − |
| 198 | 471 | * | * | ** | * | *** | *** | + |
| 199 | 467 | * | * | ** | *** | *** | *** | + |
| 200 | 441 | * | * | ** | * | *** | *** | + |
| 201 | 443 | * | * | ** | *** | *** | *** | − |
| 202 | 471 | * | * | *** | *** | *** | *** | + |
| 203 | 387 | * | ** | ** | *** | *** | *** | + |
| 204 | 417 | * | * | * | *** | *** | ** | + |

TABLE 2-continued

Examples of compounds of formula (I-A) and (I-B) including mass spectrometry data and biological activity against representative fungal diseases and insects.

| ID | MS [M + H]+ | COCHSA | COLLLA | LEPTNO | PSPECU | PUCCRT | PYRIOR | >80% mortality on any insect species @ 4000 ppm |
|---|---|---|---|---|---|---|---|---|
| 205 | 431 | * | * | ** | *** | *** | ** | − |
| 206 | 414 | NT | NT | * a | NT | * b | NT | NT |
| 207 | 401 | * | * | * | *** | *** | *** | − |
| 208 | 324 | * | * | * | ** | *** | *** | − |
| 209 | 310 | * | * | ** | * | ** | * | − |
| 210 | 362 | * | * | * | *** | *** | *** | − |
| 211 | 348 | * | * | * | * | ** | ** | − |
| 212 | 493 | ** | *** | ** | *** | *** | *** | + |
| 213 | 471 | * | * | * | *** | *** | *** | + |
| 214 | 473 | * | * | *** | * | ** | ** | + |
| 215 | 455 | * | * | ** | *** | *** | *** | + |
| 216 | 430 | * | * | *** | *** | *** | *** | + |
| 217 | 368 | ** | * | NT | ** | * | * | − |
| 218 | —8 | NT | NT | NT | NT | NT | NT | NT |
| 219 | 312 | NT | NT | NT | NT | NT | NT | NT |
| 220 | 286 | NT | NT | NT | NT | NT | NT | NT |
| 221 | — | NT | NT | NT | NT | NT | NT | NT |
| 222 | — | NT | NT | NT | NT | NT | NT | NT |
| 223 | — | NT | NT | NT | NT | NT | NT | NT |
| 224 | — | NT | NT | NT | NT | NT | NT | NT |
| 225 | — | NT | NT | NT | NT | NT | NT | NT |
| 226 | —9 | NT | NT | * a | NT | * b | * b | + |
| 227 | 481 | NT | NT | *** a | NT | *** b | NT | NT |
| 228 | — | NT | NT | NT | NT | NT | NT | NT |
| 229 | 297 | NT | NT | NT | NT | NT | NT | NT |
| 230 | 303 | NT | NT | NT | NT | NT | NT | NT |
| 231 | 338 | * | * | *** | * | *** | ** | + |
| 232 | 352 | * | ** | * | *** | *** | *** | + |

\* = 0-49 percent control;
\*\* = 50-79 percent control;
\*\*\* = 80-100 percent control
+ = 80% active on at least one insect species
− = Not 80% active on insect species tested
a indicates that compound was tested at 75 ppm
b indicates that compound was tested at 8.3 ppm
NT indicates not tested
Additional footnotes to Table 2. For compounds 37, 57, 62, 179, 180, 187, 188, 218, and 226, the following descriptive data are presented.
[1]Compound 37: mp 131-132° C.; 1H NMR (300 MHz, DMSO-$d_6$) δ 9.06 (d, J = 2.0 Hz, 1H), 8.88 (d, J = 5.9 Hz, 1H), 8.80 (d, J = 1.9 Hz, 1H), 8.71 (s, 1H), 8.62 (s, 1H), 7.31 (s, 0H), 6.79 (d, J = 1.6 Hz, 1H), 3.75 (dd, J = 14.6, 6.4 Hz, 2H), 3.70 (s, 3H), 2.91-2.80 (m, 2H).
[2]Compound 57: mp 215° C.; 1H NMR (300 MHz) δ 9.03 (d, J = 1.9 Hz, 1H), 8.84 (s, 1H), 8.63 (d, J = 1.9 Hz, 1H), 8.29 (dd, J = 5.0, 0.9 Hz, 1H), 7.17 (dd, J = 6.0, 1.0 Hz, 2H), 7.13-7.06 (m, 1H), 6.92 (dt, J = 4.0, 2.0 Hz, 3H), 4.01 (dd, J = 13.3, 6.9 Hz, 3H), 3.08 (t, J = 7.1 Hz, 3H).
[3]Compound 62: 1H NMR (300 MHz, CDCl$_3$) δ 9.02 (d, J = 2.0 Hz, 1H), 8.80 (s, 1H), 8.63 (d, J = 1.9 Hz, 1H), 7.24 (s, 0H), 7.13 (t, J = 8.8 Hz, 1H), 6.63 (ddd, J = 8.5, 6.7, 2.6 Hz, 2H), 3.92 (dd, J = 13.1, 6.8 Hz, 2H), 3.79 (s, 3H), 3.03 (t, J = 6.9 Hz, 2H).
[4]Compound 179: 1H NMR (300 MHz, CDCl$_3$) δ 9.04 (d, J = 2.0 Hz, 1H), 8.84 (s, 1H), 8.63 (d, J = 1.9 Hz, 1H), 7.10 (s, 1H), 6.91 (s, 1H), 6.63 (s, 1H), 6.40 (s, 1H), 3.94 (dd, J = 14.6, 6.3 Hz, 2H), 3.81 (s, 3H), 3.11-2.92 (m, 2H), 2.35 (s, 3H), 2.12 (s, 3H).
[5]Compound 180: 1H NMR (300 MHz, CDCl$_3$) δ 9.04 (d, J = 2.0 Hz, 1H), 8.84 (s, 1H), 8.63 (d, J = 1.9 Hz, 1H), 7.10 (s, 1H), 6.91 (s, 1H), 6.63 (s, 1H), 6.40 (s, 1H), 3.94 (dd, J = 14.6, 6.3 Hz, 3H), 3.81 (s, 3H), 3.11-2.92 (m, 2H), 2.35 (s, 3H), 2.12 (s, 3H).
[6]Compound 187: 1H NMR (300 MHz, DMSO) δ 9.17 (s, 1H), 9.10 (d, J = 1.9 Hz, 1H), 8.86 (d, J = 2.0 Hz, 1H), 8.67 (s, 1H), 8.36 (d, J = 5.1 Hz, 1H), 7.57-7.44 (m, 3H), 7.36-7.21 (m, 2H), 3.88 (dd, J = 13.4, 6.9 Hz, 2H), 3.05 (t, J = 7.2 Hz, 2H).
[7]Compound 188: 1H NMR (300 MHz, CDCl$_3$) δ 9.02 (dd, J = 4.8, 1.9 Hz, 1H), 8.82 (d, J = 6.4 Hz, 1H), 8.61 (dd, J = 6.5, 1.9 Hz, 1H), 8.28 (d, J = 5.4 Hz, 1H), 8.28 (d, J = 5.4 Hz, 1H), 7.13 (dd, J = 12.9, 5.7 Hz, 4H), 6.99-6.82 (m, 2H), 4.07-3.91 (m, 2H), 3.84 (dd, J = 12.0, 5.7 Hz, 2H), 3.05 (dd, J = 11.8, 4.7 Hz, 2H), 1.52 (dd, J = 13.8, 6.4 Hz, 2H), 1.52 (dd, J = 13.8, 6.4 Hz, 2H), 0.68 (td, J = 7.4, 1.8 Hz, 3H).
[8]Compound 218: 1H NMR (300 MHz, DMSO) δ 9.21 (d, J = 2.2 Hz, 1H), 9.11 (d, J = 2.1 Hz, 1H), 9.03 (s, 1H), 8.35 (d, J = 5.2 Hz, 1H), 7.42 (d, J = 5.3 Hz, 1H), 7.33 (s, 1H), 7.02 (d, J = 8.1 Hz, 1H), 6.91 (d, J = 2.0 Hz, 1H), 6.75 (dd, J = 8.1, 2.0 Hz, 1H), 4.13-3.84 (m, 2H), 2.97 (t, J = 7.4 Hz, 2H).
[9]Compound 226: 1H NMR (300 MHz, CDCl$_3$) δ 8.30 (dd, J = 4.7, 1.5 Hz, 1H), 7.99 (dd, J = 7.6, 1.8 Hz, 1H), 7.37-7.29 (m, 2H), 7.17-7.11 (m, 2H), 7.09 (dd, J = 7.5, 4.9 Hz, 1H), 7.01 (t, J = 5.9 Hz, 1H), 3.93 (dd, J = 13.4, 6.9 Hz, 2H), 3.05 (t, J = 7.1 Hz, 2H), 2.69 (s, 3H), 2.68 (s, 3H), 2.62 (s, 3H).

Fungicidal Activity

The compounds of the present invention have been found to have significant fungicidal effect, particularly for agricultural use. Many of the compounds are particularly effective for use with agricultural crops and horticultural plants. In particular, the compounds effectively control a variety of undesirable fungi that infect useful plant crops. Activity has been demonstrated for a variety of fungi, including for example the following representative fungi species: Anthracnose of Cucumber (*Collatotrichum lagenarium*—COLLLA); Spot Blotch of Wheat (*Cochliobolus sativus*—COCHSA), Downy Mildew of Cucumber (*Pseudoperonospora cubensis*—PSPECU), Rice Blast (*Magnaporthe grisea*—PYRIOR), Brown Rust of Wheat (*Puccinia recondite tritici*—PUCCRT), and Glume Blotch of Wheat (*Leptosphaeria nodorum*—LEPTNO).

It will be understood by those in the art that the efficacy of the compounds against the foregoing fungi establishes the general utility of the compounds as fungicides. The activity of the compounds as effective fungicides was determined by applying the compounds to plants and observing control of fungal disease. The compounds were formulated at 200 ppm in 10 vol. % acetone plus 90 vol. % Triton X water (deionized water 99.99 wt %+0.01 wt % Triton X100), giving a "formulated test compound." In a few cases, compounds were formulated at 75 or 8.3 ppm rather than 200 ppm in 10 vol. % acetone plus 90 vol. % Triton X water (deionized water 99.99 wt. %+0.01 wt. % Triton X100), giving a "formulated test compound." Formulated test compounds were applied to plants using a turn table sprayer fitted with two opposing air atomization nozzles which delivered approximately 1500 L/ha of spray volume.

All plants were inoculated with spores of the fungus the day after treatment, then incubated in an environment conducive to disease development. Disease severity was evaluated 4 to 15 days later, depending on the disease and the speed of disease development. The following experiments were performed in the laboratory to determine the fungicidal efficacy of the compounds of the invention.

Leaf Rust of Wheat (causal agent *Puccinia recondita tritici=Puccinia triticina*; Bayer code PUCCRT): Wheat plants (variety Yuma) were grown from seed in a soil-less peat-based potting mixture (Metromix) until the seedlings had a fully expanded first leaf. Each pot contained 3-8 seedlings. These plants were sprayed until wet with the formulated test compounds. On the following day, the leaves were inoculated with an aqueous spore suspension of *Puccinia recondita tritici* and the plants were kept in high humidity overnight to permit spores to germinate and infect the leaf. The plants were then transferred to a greenhouse until disease developed on untreated control plants.

Cucumber Anthracnose (causal agent *Colletotricum lagenarium*; Bayer code COLLLA): Cucumber plants (variety Bush Champion) were grown from seed in a soil-less peat-based potting mixture (Metromix) until the first true leaf was 20-80% expanded. Each pot contained 1 seedling. These plants were sprayed until wet with the formulated test compound. On the following day, the leaves were inoculated with an aqueous spore suspension of *Colletotricum lagenarium* and the plants were kept in high humidity for one day to permit spores to germinate and infect the leaf. The plants were then transferred to a growth chamber until disease developed on untreated control plants.

Cucumber Downy Mildew (causal agent *Pseudoperonospora cubensis*; Bayer code PSPECU): Cucumber plants (variety Bush Champion) were grown from seed in a soil-less peat-based potting mixture (Metromix) until the first true leaf was 20-80% expanded. Each pot contained 1 seedling. These plants were sprayed until wet with the formulated test compound. On the following day, the leaves were inoculated with an aqueous suspension of downy mildew sporangia and the plants were kept in high humidity for one day to permit sporangia to germinate and infect the leaf. The plants were then incubated in a growth chamber until disease developed on untreated control plants.

Glume Blotch of Wheat (causal agent *Leptosphaeria nodorum=Stagnospora nodorum*; Bayer code LEPTNO): Wheat plants (variety Yuma) were grown from seed in a 50% pasteurized soil/50% soil-less mix until the seedlings had a fully expanded first leaf. Each pot contained 3-20 seedlings. These plants were sprayed until wet with the formulated test compound. On the following day, the leaves were inoculated with an aqueous spore suspension of *Leptosphaeria nodorum* and the plants were kept in high humidity (one day in a dark dew chamber followed by four days in a lighted dew chamber) to permit spores to germinate and infect the leaf. The plants were then transferred to a greenhouse until disease developed on untreated control plants.

Rice Blast (causal agent *Magnaporthe grisea=Pyricularia oryzae*; Bayer code PYRIOR): Rice plants (variety M202) were grown from seed in a soil-less peat-based potting mixture (Metromix) until the seedlings had a partly to fully expanded second leaf. Each pot contained 5-20 seedlings. These plants were sprayed until wet with the formulated test compound. On the following day, the leaves were inoculated with an aqueous spore suspension of *Pyricularia oryzae* and the plants were kept in high humidity overnight to permit spores to germinate and infect the leaf. The plants were then transferred to a growth chamber until disease developed on untreated control plants.

Table 2 presents the activity of typical compounds of the present invention when evaluated in these experiments. The effectiveness of the test compounds at controlling disease when sprayed on leaves was determined by assessing the severity of disease on treated plants, then converting the severity to percent control based on the level of disease on untreated, inoculated plants. Data are the level (in percent) at which the given disease was controlled when the given compound was applied to the foliage of the plants at 200 ppm. In a few cases (noted in the table) the compound was applied to the plants at 75 ppm or 8.3 ppm.

Insecticidal Activity

The compounds of the present invention have been found to have insecticidal activity. Activity may be demonstrated for a variety of insects, including for example the following representative insect species: Beet Armyworm (*Spodoptera exigua*—LAPHEG) or Tobacco Budworm (*Heliothus virescens*—HELIVI); Mosquito (*Aedes aegypti*—AEDSAE), Fruit Fly (*Drosophila melanogaster*—DROSME). It will be understood by those skilled in the art that the efficacy of the compounds against the foregoing insects establishes the general utility of the compounds as insecticides.

The activity of the compounds as effective insecticides was determined by applying the compounds to diet or water, placing insects in the water or on the diet, and observing mortality after an appropriate incubation time. The compounds were formulated at 4000 ppm or 400 ppm in dimethyl sulfoxide (DMSO) giving a "formulated test compound." Formulated test compounds were diluted in 96-well plates with acetone:water solutions and applied to species-specific diet or water. The plates were infested and evaluated as described below. Results were averaged over 2-6 replications.

DROSME: Formulated test compounds were applied to microtiter plates containing fruit fly agar (10% sugar-water) to give a dose of 80 µg test compound per well. Plates were infested by placing at least three flies in each well and sealing the plate. Mortality was evaluated after incubation for two days at room temperature.

AEDSAE: Plates containing formulated test compounds at 6 µg per well were diluted with water containing mosquito larvae. Each well contained at least two larvae. Mortality was evaluated after incubation for three days at room temperature.

LAPHEG or HELIVI: Formulated test compounds were applied to 96-well plates containing Lepidoptera diet at 12 µg per well (one-tenth the rate was used for HELIVI). Plates were infested by placing at least four fresh armyworm or budworm eggs in each well and sealing the plate with cotton batting and plastic. Mortality was evaluated after incubation for seven days at 28° C.

Table 2 presents the activity of typical compounds of the present invention when evaluated in these experiments. The effectiveness of the test compounds at controlling insects was determined by assessing the mortality in treated test plates, then converting the average mortality to percent control. Each compound was tested on at least two species. If any of the species DROSME, AEDSAE, LAPHEG, or HELIVI was controlled at 80% or more, the compound was considered active (shown as "+" in Table 2). If no species was controlled at 80% or more, the compound was considered inactive (shown as "-" in Table 2).

Animal Health Activity

The compounds of the present invention have been found to have significant potential as anti-parasitics for animal health. Table 3, shown below, presents the activity of typical compounds of the present invention when evaluated in these experiments. Activity has been demonstrated by four out of five compounds screened against *Caenorhabditis elegans*, a free-living nematode that is an indicator species for animal parasites. It will be understood by those in the art that the efficacy of four compounds against *Caenorhabditis elegans*, which at 10 μg/mL was equivalent to the commercial anti-parasttic product ivermectin, establishes the potential utility of these compounds to control parasites that attack animals.

The activity of the compounds against *Caenorhabditis elegans* was determined by dissolving compounds in DMSO, then applying them to petri dishes containing Nematode Growth Medium agar to a final concentration of 10 μg compound per milliliter agar. *Escherichia coli* bacteria were grown on the plates to provide a food source for the larvae of *Caenorhabditis elegans*. The bacteria were heat-killed at 65° C. before compounds were added to the plates.

The plates with compound and heat-killed bacteria were infested with 10 microliter drops containing eggs from wild-type *Caenorhabditis elegans* worms. Adult worms were dissolved in KOH and bleach and washed in Ringers solution to generate the egg suspension. Each compound was screened with approximately 400 eggs, divided between two petri dishes. Egg hatching was evaluated after 24 h at 20° C. Mortality was averaged over the two plates.

TABLE 3

Activity of compounds of the formula (I-A) against *Caenorhabditis elegans*. Application rate is 10 micrograms per milliliter agar.

| Compound | Percent Mortality |
|---|---|
| 2 | 100 |
| 101 | 100 |
| 126 | 100 |
| 137 | 1 |
| 159 | 97 |
| Ivermectin | 95 |

The invention claimed is:

1. A composition comprising a compound of Formula I-A:

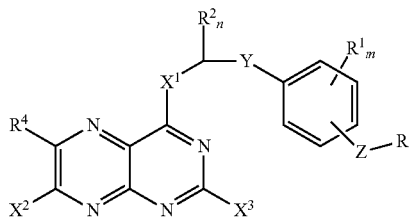

I-A wherein:
R is a monocyclic 5- or 6-membered heterocyclic ring or a fused bicyclic heterocyclic ring comprising at least one 5- or 6-membered heterocyclic ring, wherein the monocyclic or fused bicyclic ring is optionally substituted with H, halo, lower alkyl, lower alkoxy, benzyloxy, lower alkenyl, lower alkynyl, haloalkyl, haloalkoxy, $NO_2$, CN, lower alkoxycarbonyl, lower alkylcarbonyl, lower alkyl-$SO_q$, aldoxime, and lower alkyloxime, optionally substituted on oxygen by lower alkyl;

Z is a C—C single bond, $CH_2$, NH, O, S, $CH_2O$, $OCH_2$, $CH_2CH_2O$, or $OCH_2CH_2$;

m is 4;

q is 0, 1, or 2;

each $R^1$ is independently H, halo, lower alkyl, lower alkenyl, lower alkynyl, hydroxy, lower alkoxy, haloalkyl, haloalkoxy, $NO_2$, CN, lower alkylcarbonyl, lower alkoxycarbonyl, mercapto, lower alkylthio, aldoxime, and lower alkyloxime, optionally substituted on oxygen by lower alkyl;

Y is a C—C single bond, $C(R^5)_nO$, or $C(R^5)_n$;

n is 2;

alternatively $(R^1)_m$, Z, and R may be taken together to form a fused 5 or 6 membered heterocycle optionally substituted with H, halo, lower alkyl, lower alkoxy, benzyloxy, lower alkenyl, lower alkynyl, haloalkyl, haloalkoxy, $NO_2$, CN, lower alkylcarbonyl, lower alkoxycarbonyl and lower alkyl-$SO_q$;

$R^2$ is independently H or lower alkyl;

$R^4$ is H, halogen, lower alkyl, lower alkoxy or lower haloalkyl;

$R^5$ is independently H or lower alkyl;

$X^1$ is $NR^3$, O, or S, where $R^3$ is selected from H, lower alkyl, lower alkylcarbonyl, lower alkoxycarbonyl, hydroxy, lower alkoxy, lower alkyl-$SO_q$, or phenyl-$SO_q$ optionally substituted with H, halo, lower alkyl, lower alkoxy, benzyloxy, lower alkenyl, lower alkynyl, haloalkyl, haloalkoxy, $NO_2$, CN, lower alkoxycarbonyl, lower alkylcarbonyl, lower alkyl-$SO_q$, aldoxime, and lower alkyloxime, optionally substituted on oxygen by lower alkyl;

$X^2$ is H, halogen or lower alkyl; and $X^3$ is H, halogen or lower alkyl;

with the proviso that when Y is $C(R^5)_n$, $(R^2)_n$ and $(R^1)_m$ may be taken together to form

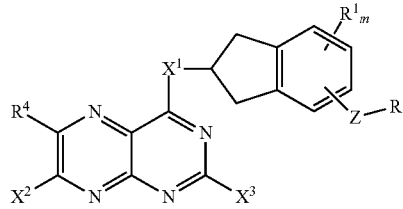

and at least one additional agriculturally active compound selected from the group consisting of fungicides, insecticides, nematicides, miticides, arthropodicides, bactericides, plant growth stimulators or regulators, nitrification inhibitors, and nutrients.

2. The composition according to claim 1, wherein:
Z is $CH_2$, NH, O, S, $CH_2O$, $OCH_2$, $CH_2CH_2O$, or $OCH_2CH_2$.

3. The composition according to claim 2, wherein Z is O.

4. The composition according to claim 2, wherein the compound of Formula I-A is:

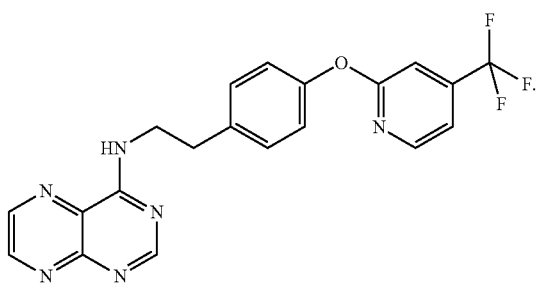 [SMILES: FC(F)(F)c1ccnc(Oc2ccc(CCNc3ncnc4nccnc34)cc2)c1]

5. A composition comprising a compound of Formula I-B:

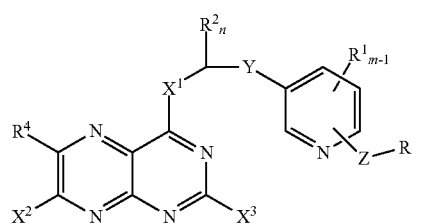

I-B wherein:
- R is haloalkyl, phenyl, or a monocyclic 5- or 6-membered heterocyclic ring or a fused bicyclic heterocyclic ring comprising at least one 5- or 6-membered heterocyclic ring, wherein the monocyclic or fused bicyclic ring is optionally substituted with H, halo, lower alkyl, lower alkoxy, benzyloxy, lower alkenyl, lower alkynyl, haloalkyl, haloalkoxy, $NO_2$, CN, lower alkoxycarbonyl, lower alkylcarbonyl, lower alkyl-$SO_q$, aldoxime, and lower alkyloxime, optionally substituted on oxygen by lower alkyl;
- Z is a C—C single bond, $CH_2$, NH, O, S, $CH_2O$, $OCH_2$, $CH_2CH_2O$, or $OCH_2CH_2$;
- m is 4;
- q is 0, 1, or 2;
- each $R^1$ is independently H, halo, lower alkyl, lower alkenyl, lower alkynyl, hydroxy, lower alkoxy, haloalkyl, haloalkoxy, $NO_2$, CN, lower alkylcarbonyl, lower alkoxycarbonyl, mercapto, lower alkylthio, aldoxime, and lower alkyloxime, optionally substituted on oxygen by lower alkyl;
- Y is a C—C single bond, $C(R^5)_nO$, or $C(R^5)_n$;
- n is 2;
- alternatively $R^1_{m-1}$, Z, and R may be taken together to form a fused 5 or 6 membered heterocycle optionally substituted with H, halo, lower alkyl, lower alkoxy, benzyloxy, lower alkenyl, lower alkynyl, haloalkyl, haloalkoxy, $NO_2$, CN, lower alkylcarbonyl, lower alkoxycarbonyl and lower alkyl-$SO_q$;
- $R^2$ is independently H or lower alkyl;
- $R^4$ is H, halogen, lower alkyl, lower alkoxy or lower haloalkyl;
- $R^5$ is independently H or lower alkyl;
- $X^1$ is $NR^3$, O, or S, where $R^3$ is selected from H, lower alkyl, lower alkylcarbonyl, lower alkoxycarbonyl, hydroxy, lower alkoxy, lower alkyl-$SO_q$, or phenyl-SOq optionally substituted with H, halo, lower alkyl, lower alkoxy, benzyloxy, lower alkenyl, lower alkynyl, haloalkyl, haloalkoxy, $NO_2$, CN, lower alkoxycarbonyl, lower alkylcarbonyl, lower alkyl-$SO_q$, aldoxime, and lower alkyloxime, optionally substituted on oxygen by lower alkyl;
- $X^2$ is H, halogen or lower alkyl;
- $X^3$ is H, halogen or lower alkyl; and
- at least one additional agriculturally active compound selected from the group consisting of fungicides, insecticides, nematicides, miticides, arthropodicides, bactericides, plant growth stimulators or regulators, nitrification inhibitors, and nutrients.

* * * * *

UNITED STATES PATENT AND TRADEMARK OFFICE
CERTIFICATE OF CORRECTION

PATENT NO. : 8,895,568 B2  
APPLICATION NO. : 13/898372  
DATED : November 25, 2014  
INVENTOR(S) : William K. Brewster Page 1 of 1

It is certified that error appears in the above-identified patent and that said Letters Patent is hereby corrected as shown below:

Title page, item [57] Abstract, the end of the 2<sup>nd</sup> line should read (4_(het- In the Claims In Claim 1, Column 154, Line 50 the formula should read

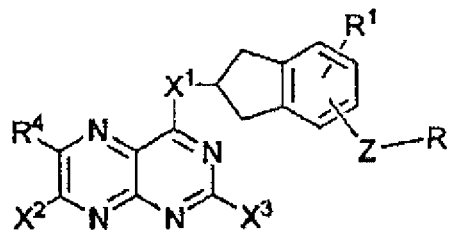

Signed and Sealed this  
Fourteenth Day of April, 2015

Michelle K. Lee  
*Director of the United States Patent and Trademark Office*